US012203933B2

(12) United States Patent
Charlesworth et al.

(10) Patent No.: US 12,203,933 B2
(45) Date of Patent: Jan. 21, 2025

(54) METHODS AND MATERIALS FOR IDENTIFYING AND TREATING MEMBRANOUS NEPHROPATHY

(71) Applicant: Mayo Foundation for Medical Education and Research, Rochester, MN (US)

(72) Inventors: M. Cristine Charlesworth, Rochester, MN (US); Sanjeev Sethi, Rochester, MN (US); Fernando C. Fervenza, Rochester, MN (US); Benjamin J. Madden, Stewartville, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 875 days.

(21) Appl. No.: 17/254,086

(22) PCT Filed: Aug. 15, 2019

(86) PCT No.: PCT/US2019/046676
§ 371 (c)(1),
(2) Date: Dec. 18, 2020

(87) PCT Pub. No.: WO2020/037135
PCT Pub. Date: Feb. 20, 2020

(65) Prior Publication Data
US 2021/0270832 A1    Sep. 2, 2021

Related U.S. Application Data

(60) Provisional application No. 62/764,681, filed on Aug. 15, 2018.

(51) Int. Cl.
*G01N 33/564* (2006.01)

(52) U.S. Cl.
CPC ..... *G01N 33/564* (2013.01); *G01N 2333/705* (2013.01); *G01N 2333/91102* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 8,361,721 | B2 | 1/2013 | Copland et al. |
| 2006/0040293 | A1 | 2/2006 | Salonen et al. |
| 2007/0210253 | A1 | 9/2007 | Behar et al. |
| 2010/0167285 | A1 | 7/2010 | Schreiber et al. |
| 2010/0196426 | A1 | 8/2010 | Skog et al. |
| 2013/0280738 | A1 | 10/2013 | Salant et al. |
| 2013/0303395 | A1 | 11/2013 | Lueking et al. |
| 2017/0216244 | A1 | 8/2017 | Tufro |
| 2017/0219580 | A1 | 8/2017 | Lambeau et al. |
| 2018/0203020 | A1 | 7/2018 | Esnault et al. |
| 2019/0183969 | A1 | 6/2019 | Zhu |
| 2020/0088734 | A1 | 3/2020 | Lotvall et al. |
| 2022/0389108 | A1 | 12/2022 | Sethi et al. |
| 2023/0314425 | A1 | 10/2023 | Sethi et al. |
| 2023/0348610 | A1 | 11/2023 | Sethi et al. |

FOREIGN PATENT DOCUMENTS

| | | |
|---|---|---|
| EP | 2977758 | 1/2016 |
| WO | WO 2008/118969 | 10/2008 |
| WO | WO 2016/012542 | 1/2016 |
| WO | WO 2017/009245 | 1/2017 |
| WO | WO 2018/031947 | 2/2018 |
| WO | WO 2019/030461 | 2/2019 |
| WO | WO 2020/037135 | 2/2020 |
| WO | WO 2021/178863 | 9/2021 |
| WO | WO 2022/103598 | 5/2022 |
| WO | WO 2023/172847 | 9/2023 |

OTHER PUBLICATIONS

Karp et al., Genetics of Childhood Steroid Sensitive Nephrotic Syndrome (SSNS), Pediatr. Nephrol., 32(9), (2017), p. 1481-1488 (Year: 2017).*
MedlinePlus. "EXT1 gene". https://medlineplus.gov/genetics/gene/ext1/. (2017). Accessed: May 17, 2024 (Year: 2017).*
Cooper GM. The Cell: A Molecular Approach. 2nd edition. Sunderland (MA): Sinauer Associates; 2000. Detection of Nucleic Acids and Proteins. Available from: https://www.ncbi.nlm.nih.gov/books/NBK9916/ (Year: 2000).*
Bech et al., "Association of Anti-PLA2R Antibodies with Outcomes after Immunosuppressive Therapy in Idiopathic Membranous Nephropathy," Clin. J. Am. Soc. Nephrology, Aug. 7, 2014, 9(8):1386-1392.
EP Extended Search Report in European Appln. No. 19850371.6, dated Feb. 2, 2022, 11 pages.
Iwakura et al., "Primary Membranous Nephropathy with Enhanced Staining of Exostosin 1/Exostosin 2 in the Glomeruli: A Report of 2 Cases," Kidney Medicine, May 31, 2021, 3(4):669-673.
Bobart et al., "A Target Antigen-Based Approach to the Classification of Membranous Nephropathy," Mayo Clin. Proceedings, Mar. 2021, 96(3):577-591.
Du et al., "Elevated semaphorin5A in systemie lupus erythematosus is in association with disease activity and lupus nephritis," Clin. Exp. Immunology, Feb. 17, 2017, 188(2):234-242.
Ahn et al., "Cloning of the putative tumour suppressor gene for hereditary multiple exostoses (EXT1)," Nat. Genetics, Oct. 1, 1995, 11(2):137-143.

(Continued)

*Primary Examiner* — Ellen J Marcsisin
(74) *Attorney, Agent, or Firm* — Fish & Richardson P.C.

(57) ABSTRACT

This document provides methods and materials involved in identifying and treating mammals (e.g., humans) having membranous nephropathy. For example, methods and materials for detecting the presence of autoantibodies specific for an EXT1 and/or EXT2 polypeptide as well as methods and materials for detecting the presence of kidney tissue having an elevated level of an EXT1 and/or EXT2 polypeptide are provided. In addition, methods and materials for treating membranous nephropathy by administering an immunosuppressant are provided.

17 Claims, 20 Drawing Sheets

Specification includes a Sequence Listing.

(56) References Cited

OTHER PUBLICATIONS

Alarcón, "Multiethnic lupus cohorts: what have they taught US?," Reumatol. Clinica, Dec. 23, 2010, 7(1):3-6.
Almaani et al., "Update on Lupus Nephritis," Clin. J. Am. Soc. Nephrology, Nov. 7, 2016, 12(5):825-835.
Alto et al., "Semaphorins and their Signaling Mechanisms," Methods Mol. Biology, Oct. 28, 2016, 1493:1-25.
Altschul et al., "Gapped BLAST and PSI-BLAST: a new generation of protein database search. programs," Nucleic Acids Research, Sep. 1, 1997, 25(17):3389-3402.
Anders, "Nephropathic autoantigens in the spectrum of lupus nephritis," Nat. Rev. Nephrology, Jun. 13, 2019, 15(10):595-596.
Aoki et al., "The reduction of heparan sulphate in the glomerular basement membrane does not augment urinary albumin excretion," Nephrol. Dial. Transplantation, Jan. 1, 2018, 33(1):26-33.
Bajema et al., "Revision of the International Society of Nephrology/Renal Pathology Society classification for lupus nephritis: clarification of definitions, and modified National Institutes of Health activity and chronicity indices," Kidney International, Apr. 1, 2018, 93(4):789-796.
Beck Jr. et al., "Membranous nephropathy: from models to man," J. Clin. Investigation, Jun. 2, 2014, 124(6):2307-2314.
Beck Jr. et al., "M-type phospholipase A2 receptor as target antigen in idiopathic membranous nephropathy," N. Engl. J. Medicine, Jul. 2, 2009, 361(1):11-21.
Beck Jr. et al., "Rituximab-Induced Depletion of Anti-PLA2R Autoantibodies Predicts Response in Membranous Nephropathy," J. Am. Soc. Nephrology, Jul. 22, 2011, 22(8):1543-1550.
Bertelli et al., "Molecular and Cellular Mechanisms for Proteinuria in Minimal Change Disease," Front. Medicine, Jun. 11, 2018, 5:170, 13 pages.
Borza, "Glomerular basement membrane heparan sulfate in health and disease: A regulator of local complement activation," Matrix Biology, Sep. 6, 2016, 57-58:299-310.
Brasch et al., "Thinking outside the cell: how cadherins drive adhesion," Trends Cell Biology, May 1, 2012, 22(6):299-310.
Busse et al., "Contribution of EXT1, EXT2, and EXTL3 to Heparan Sulfate Chain Elongation," J. Biol, Chemistry, Nov. 9, 2007, 282(45):32802-32810.
Busse et al., "In Vitro Polymerization of Heparan Sulfate Backbone by the EXT Proteins," J. Biol. Chemistry, Oct. 17, 2003, 278(42):41333-41337.
Busse-Wicher et al., "The extostosin family: Proteins with many functions," Matrix Biology, Apr. 2014, 35:25-33.
Chen et al., "Glomerular basement membrane and related glomerular disease," Transl. Research, Oct. 2012, 160(4):291-297.
Chen et al., "Loss of heparan sulfate glycosaminoglycan assembly in podocytes does not lead to proteinuria," Kidney International, Aug. 2008, 74(3):289-299.
Chen et al., "Podocytes require the engagement of cell surface heparan sulfate proteoglycans for adhesion to extracellular matrices," Kidney International, Dec. 1, 2010, 78(11):1088-1099.
Cook et al., "Genetic Heterogeneity in Families with Hereditary Multiple Exostoses," Am. J. Hum. Genetics, Jul. 1993, 53(1):71-79.
Couser, "Primary Membranous Nephropathy," Clin. J. Am. Soc. Nephrology, May 26, 2017, 12(6):983-997.
De Vriese et al., "A Proposal for a Serology-Based Approach to Membranous Nephropathy," J. Am. Soc. Nephrology, Oct. 24, 2016, 28(2):421-430.
Duncan et al., "The link between heparan sulfate and hereditary bone disease: finding a function for the EXT family of putative tumor suppressor proteins," J. Clin. Investigation, Aug. 2001, 108(4):511-516.
Fervenza et al., "Rituximab or Cyclosporine in the Treatment of Membranous Nephropathy." N. Engl. J. Medicine, Jul. 4, 2019, 381(1):36-46.
Frank et al., "Protocadherins," Curr. Opin, Cell Biology, Oct. 2002, 14(5):557-562.

Guan et al., "Autocrine class 3 semaphorin system regulates slit diaphragm proteins and podocyte survival," Kidney International, May 2006, 69(9):1564-1569.
Halbleib et al., "Cadherins in development: cell adhesion, sorting, and tissue morphogenesis," Genes Development, Dec. 1, 2006, 20(23):3199-3214.
Hanset et al., "Podocyte Antigen Staining to Identify Distinct Phenotypes and Outcomes in Membranous Nephropathy: A Retrospective Multicenter Cohort Study," Am. J. Kidney Diseases, Jul. 12, 2020, 76(5):624-635.
Hasebe et al., "Efficient Production and Characterization of Recombinant Human NELL1 Protein in Human Embryonic Kidney 293-F Cells," Mol. Biotechnology, Aug. 5, 2011, 51(1):58-66.
Hasebe et al., "The C-terminal region of NELL1 mediates osteoblastic cell adhesion through integrin $\alpha 3\beta 1$," FEBS Letters, Jun. 20, 2012, 586(16):2500-2506.
Herwig et al., "Thrombospondin Type I Domain-Containing 7A Localizes to the Slit Diaphragm and Stabilizes Membrane Dynamics of Fully Differentiated Podocytes," J. Am. Soc. Nephrology, Apr. 10, 2019, 30(5):824-839.
Hihara et al., "Anti-Phospholipase A2 Receptor (PLA2R) Antibody and Glomerular PLA2R Expression in Japanese Patients with Membranous Nephropathy," PLoS One, Jun. 29, 2016, 11(6):e0158154, 12 pages.
Huong et al., "Renal involvement in systemic lupus erythematosus. A study of 180 patients from a single center," Medicine (Baltimore), May 1999, 78(3):148-166.
Itakura et al., "Heparan sulfate is a clearance receptor for aberrant extracellular proteins," J. Cell Biology, Mar. 2, 2020, 19(3):e201911126.
Kanwar et al., "Contribution of Proteoglycans Towards the Integrated Functions of Renal Glomerular Capillaries: A Historical Perspective," Am. J. Pathology, Jul. 2007, 171(1):9-13.
Kuroda et al., "Biochemical Characterization and Expression Analysis of Neural Thrombospondin-1-like Proteins NELL1 and NELL2," Biochem. Biophys. Res. Communications, Nov. 1999, 265(1):79-86.
Lee et al., "Overall and cause-specific mortality in systemic lupus erythematosus: an updated meta-analysis," Lupus, Jan. 24, 2016, 25(7):727-734.
Luce et al., "The neuronal EGF-related genes NELL1 and NELL2 are expressed in hemopoietic cells and developmentally regulated in the B lineage," Gene, Apr. 29, 1999, 231(1-2):121-126.
Makker et al., "Idiopathic membranous nephropathy: an autoimmune disease," Semin. Nephrology, Jul. 2011, 31(4):333-340.
Matshuhashi et al., "New gene, nel, encoding a M(r) 93 K protein with EGF-like repeats is strongly expressed in neural tissues of early stage chick embryos," Dev. Dynamics, Jun. 1995, 203(2):212-222.
McCarthy et al., "The Glomerular Basement Membrane as a Model System to Study the Bioactivity of Heparan Sulfate Glycosaminoglycans," Microsc. Microanalysis, Feb. 2012, 18(1):3-21.
McCormick et al., "The putative tumor suppressors EXT1 and EXT2 form a stable complex that accumulates in the Golgi apparatus and catalyzes the synthesis of heparan sulfate," Proc. Natl. Acad. Sci. USA, Jan. 18, 2000, 97(2):668-673.
Miner, "Glomerular basement membrane composition and the filtration barrier," Pediatr. Nephrology, Feb. 15, 2011, 26(9):1413-1417.
Miner, "Glomerular filtration: the charge debate charges ahead," Kidney International, Aug. 2008, 74(3):259-261.
Miner, "The glomerular basement membrane," Exp. Cell Research, Mar. 5, 2012, 318(9):973-978.
Morishita et al., "Protocadherin family: diversity, structure, and function," Curr. Opin. Cell Biology, Oct. 23, 2007, 19(5):584-592.
Nakamura et al., "Expression and regulatory effects on cancer cell behavior of NELL1 and NELL2 in human renal cell carcinoma," Cancer Science, Mar. 26, 2015, 106(5):656-664.
Nesvizhskii et al., "A Statistical Model for Identifying Proteins by Tandem Mass Spectrometry," Anal. Chemistry, Jul. 15, 2003, 75(17):4646-4658.
Neufeld et al., "The semaphorins and their receptors as modulators of tumor progression," Drug Resist. Updates, Aug. 28, 2016, 29:1-12.

(56) References Cited

OTHER PUBLICATIONS

Paulson et al., "Glycosyltransferases: Structure, localization, and control of cell type-specific glycosylation," J. Biol. Chemistry, Oct. 15, 1989, 264(3):17615-17618.

PCT International Preliminary Report on Patentability in International Appln. No. PCT/US2019/046676, dated Feb. 16, 2021, 7 pages.

PCT International Search Report and Written Opinion in International Appln. No. PCT/US2019/046676, dated Oct. 24, 2019, 11 pages.

Pourcine et al., "Prognostic value of PLA2R autoimmunity detected by measurement of anti-PLA2R antibodies combined with detection of PLA2R antigen in membranous nephropathy: A single-centre study over 14 years," PLoS One, Mar. 3, 2017, 12(3):e0173201, 18 pages.

Pozdzik et al., "Membranous Nephropathy and Anti-Podocytes Antibodies: Implications for the Diagnostic Workup and Disease Management," BioMed Res. International, Jan. 8, 2018, 2018:6281054, 19 pages.

ProteinAtlas.org [online], "NELL1 - Kidney," available on or before Feb. 9, 2021 via Internet Archive: Wayback Machine URL<https://web.archive.org/web/20210209071800/https://www.proteinatlas.org/ENSG00000165973-NELL1/tissue/kidney>, retrieved on Jun. 4, 2021, retrieved from URL<https://www.proteinatlas.org/ENSG00000165973-NELL1/tissue/kidney>, 3 pages.

ProteinAtlas.org [online], "PCDH7—Kidney," available on or before Jun. 26, 2015 via Internet Archive: Wayback Machine URL<https://web.archive.org/web/20150626215650/https://www.proteinatlas.org/ENSG00000169851-PCDH7/tissue/kidney>, retrieved on Jun. 11, 2021, retrieved from URL<https://www.proteinatlas.org/ENSG00000169851-PCDH7/tissue/kidney>, 3 pages.

Raats et al., "Glomerular heparan sulfate alterations: Mechanisms and relevance for proteinuria," Kidney International, Feb. 2000, 57(2):385-400.

Ravindran et al., "In Patients with Membranous Lupus Nephritis, Exostosin-Positivity and Exostosin-Negativity Represent Two Different Phenotypes," J. Am. Soc. Nephrology, Jan. 21, 2021, 32(3):695-706.

Ravindran et al., "Proteomic Analysis of Complement Proteins in Membranous Nephropathy," Kidney Int. Reports, Jan. 30, 2020, 5(5):618-626.

Roberts et al., "Familial Nephropathy and Multiple Exostoses With Exostosin-1 (EXT1) Gene Mutation," J. Am. Soc. Nephrology, Mar. 2008, 19(3):450-453.

Ronco et al., "Pathogenesis of membranous nephropathy: recent advances and future challenges," Nat. Rev. Nephrology, Feb. 28, 2012, 8(4):203-213.

Ronco et al., "Pathophysiological advances in membranous nephropathy: time for a shift in patient's care," Lancet, May 16, 2015, 385(9981):1983-1992.

Rops et al., "Modulation of heparan sulfate in the glomerular endothelial glycocalyx decreases leukocyte influx during experimental glomerulonephritis," Kidney International, Apr. 23, 2014, 86(5):932-942.

Rosini et al., "Thrombospondin-1 promotes matrix homeostasis by interacting with collagen and lysyl oxidase precursors and collagen cross-linking sites," Sci. Signaling, May 29, 2018, 11(532):eaar2566, 16 pages.

Sano et al., "Protocadherins: a large family of cadherin-related molecules in central nervous system," EMBO Journal, Jun. 1993, 12(6):2249-2256.

Sethi et al., "Exostosin I/Exostosin 2-Associated Membranous Nephropathy," J. Am. Soc. Nephrology, May 6, 2019, 30(6):1123-1136.

Sethi et al., "Mass Spectrometry Based Proteomic Diagnosis of Renal Immunoglobulin Heavy Chain Amyloidosis," Clin. J. Am. Soc. Nephrology, Sep. 28, 2010, 5(12):2180-2187.

Sethi et al., "Mass spectrometry based proteomics in the diagnosis of kidney disease," Curr. Opin. Nephrol. Hypertension, May 2013, 22(3):273-280.

Sethi et al., "Neural epidermal growth factor-like 1 protein (NELL-1) associated membranous nephropathy," Kidney International, Oct. 10, 2019, 97(1):163-174.

Sethi et al., "Protocadherin 7-Associated Membranous Nephropathy," J. Am. Soc. Nephrology, Apr. 8, 2021, 32(5):1249-1261.

Sethi et al., "Semaphorin 3B-associated membranous nephropathy is a distinct type of disease predominantly present in pediatric patients," Kidney International, Nov. 1, 2020, 98(5):1253-1264.

Stoddard et al., "Structure and function insights garnered from in silico modeling of the thrombospondin type-1 domain-containing 7A antigen," Proteins, Dec. 21, 2018; 87(2):136-145.

Stojan et al., "Epidemiology of systemic lupus erythematosus: an update," Curr. Opin. Rheumatology, Mar. 2018, 30(2):144-150.

Sugar et al., "N-sulfation of heparan sulfate is critical for syndecan-4-mediated podocyte cell-matrix. interactions," Am. J. Physiol. Renal Physiology, Mar. 2, 2016, 310(1):F1123-F1135.

Sugar et al., "Podocyte-specific deletion of NDST1, a key enzyme in the sulfation of heparan sulfate glycosaminoglycans, leads to abnormalities in podocyte organization in vivo," Kidney International, Aug. 7, 2013, 85(2):307-318.

Takamatsu et al., "Diverse roles for semaphorin-plexin signaling in the immune system," Trends Immunology, Feb. 9, 2012, 33(3):127-135.

Tapia et al., "Semaphorin3a disrupts podocyte foot processes causing acute proteinuria," Kidney International, Dec. 12, 2007, 73(6):733-740.

Ting et al., "Human NELL-1 Expressed in Unilateral Coronal Synostosis," J. Bone Miner. Research, Jan. 1999, 14(1): 80-89.

Tomas et al., "Autoantibodies against thrombospondin type 1 domain-containing 7A induce membranous nephropathy," J. Clin. Investigation, May 23, 2016, 126(7):2519-2532.

Tomas et al., "Thrombospondin Type-1 Domain-Containing 7A in Idiopathic Membranous Nephropathy," N. Engl. J. Medicine, Nov. 13, 2014, 371(24):2277-2287.

UniProt Accession No. O60245, "Protocadherin-7," dated Jun. 7, 2017, 5 pages.

van den Born et al., "Distribution of GBM heparan sulfate proteoglycan core protein and side chains in human glomerular diseases," Kidney International, Feb. 1993, 43(2):454-463.

Vrana et al., "Classification of amyloidosis by laser microdissection and mass spectrometry based proteomic analysis in clinical biopsy specimens," Blood, Oct. 1, 2009, 114(24):4957-4959.

Watanabe et al., "Cloning and Characterization of Two Novel Human cDNAs (NELL1 and NELL2) Encoding Proteins with Six EGF-like Repeats," Genomics, Dec. 15, 1996, 38(3):273-276.

Yazdani et al., "The semaphorins," Genome Biology, Mar. 30, 2006, 7(3):211, 14 pages.

Zaghrini et al., "Novel ELISA for thrombospondin type 1 domain-containing 7A autoantibodies in membranous nephropathy," Kidney International, Mar. 2019, 95(3):666-679.

Zhang et al., "Craniosynostosis in transgenic mice overexpressing Nell-1," J. Clin. Investigation, Sep. 2002, 110(6):861-870.

Zhang et al., "Overexpression of Nell-1, a Craniosynostosis-Associated Gene, Induces Apoptosis in Osteoblasts During Craniofacial Development," J. Bone Miner. Research, Dec. 2003, 18(12):2126-2134.

Zhang et al., "The Role of NELL-1, a Growth Factor Associated with Craniosynostosis, in Promoting Bone Regeneration," J. Dent. Research, Jul. 20, 2010, 89(9):865-878.

Prunotto et al., "Autoimmunity in membranous nephropathy targets aldose reductase and SOD2," J. Am. Soc. Nephrology, Mar. 2010, 21(3):507-519.

U.S. Appl. No. 17/642,773, filed Mar. 14, 2022, Sanjeev Sethi, Pending.

U.S. Appl. No. 17/758,361, filed Jul. 5, 2022, Sanjeev Sethi, Pending.

U.S. Appl. No. 18/021,641, filed Feb. 16, 2023, Sanjeev Sethi, Published as U.S. Patent Application Publication No. 2023/0314425.

U.S. Appl. No. 18/033,903, filed Apr. 26, 2023, Fernando C. Fervenza, Pending.

(56) References Cited

OTHER PUBLICATIONS

Bobart et al., "Noninvasive diagnosis of primary membranous nephropathy using phospholipase A2 receptor antibodies," Kidney Int., Feb. 2019, 95(2):429-438.

Caza et al., "Neural cell adhesion molecule 1 is a novel autoantigen in membranous lupus nephritis," Kidney Int., Jul. 2021, 100(1):171-181.

Chang et al., "Spectrum of renal pathology in hematopoietic cell transplantation: a series of 20 patients and review of the literature," Clin. J. Am. Soc. Nephrol., Sep. 2007, 2(5):1014-1023.

Ciani et al., "Mice Lacking the Giant Protocadherin mFAT1 Exhibit Renal Slit Junction Abnormalities and a Partially Penetrant Cyclopia and Anophthalmia Phenotype," Mol. Cell Biol., May 2003, 23(10):3575-3582.

Fabretti et al., "Expanding the Spectrum of FAT1 Nephropathies by Novel Mutations That Affect Hippo Signaling, " Kidney Int. Rep., May 2021, 6(5):1368-1378.

Feltkamp et al., "Elution of antibodies from biopsy tissue," J. Clin. Pathol., Oct. 1970, 23(7):629-631.

Garred et al., "The IgG subclass pattern of complement activation depends on epitope density and antibody and complement concentration," Scand. J. Immunol., Sep. 1989, 30(3):379-382.

Gee et al., "FAT1 mutations cause a glomerulotubular nephropathy," Nat. Commun., Feb. 2016, 7:10822.

Hiesse et al., "Membranous nephropathy in a bone marrow transplant recipient," Am. J. Kidney Dis., Feb. 1988, 11(2):188-191.

Hu, "The role of graft-versus-host disease in haematopoietic cell transplantation-associated glomerular disease," Nephrol. Dial. Transplant., Jun. 2011, 26(6):2025-2031.

Inoue et al., "FAT is a component of glomerular slit diaphragms," Kidney Int., Mar. 2001, 59(3):1003-1012.

Kudose et al., "NELL1-Associated Membranous Glomerulopathy After Hematopoietic Stem Cell Transplantation," Kidney Int. Rep., Jul. 2021, 6(7):1992-1995.

Mahoney et al., "The fat tumor suppressor gene in Drosophila encodes a novel member of the cadherin gene superfamily," Cell, Nov. 1991, 67(5):853-868.

Michaelsen et al., "Human IgG subclass pattern of inducing complement-mediated cytolysis depends on antigen concentration and to a lesser extent on epitope patchiness, antibody affinity and complement concentration," Eur. J. Immunol., Jan. 1991, 21(1):11-16.

Mustjoki et al., "Somatic Mutations in 'Benign' Disease," N. Engl. J. Med., May 2021, 384:2039-2052.

Na et al., "Dissecting the relationships of IgG subclasses and complements in membranous lupus nephritis and idiopathic membranous nephropathy," PLoS One, Mar. 2017, 12(3):e0174501.

Nasr et al., "Membranous Nephropathy With Extensive Tubular Basement Membrane Deposits Following Allogeneic Hematopoietic Cell Transplant: A Report of 5 Cases," Am. J. Kidney Dis., Jun. 2022, 79(6):904-908.

Nergizoglu et al., "Chronic graft-versus-host disease complicated by membranous glomerulonephritis," Nephrol. Dial. Transplant., Oct. 1999, 14(10):2461-2463.

Pronina et al., "Altered expression of the SEMA3B gene in epithelial tumors," Cell Mol. Biol., Jun. 2009, 43(3):403-409.

Ronco et al., "Membranous nephropathy," Nat. Rev. Dis. Primers, Sep. 2021, 7(1):69.

Sadeqzadeh et al., "Sleeping giants: emerging roles for the fat cadherins in health and disease," Med. Res. Rev., Jan. 2014, 34(1):190-221.

Sato et al., "Nephrotic syndrome in a bone marrow transplant recipient with chronic graft-versus-host disease," Bone Marrow Transplant., Aug. 1995, 16(2):303-305.

Sethi et al., "A proposal for standardized grading of chronic changes in native kidney biopsy specimens," Kidney Int., Apr. 2017, 91(4):787-789.

Sethi et al., "Abstract: PO1467: Hematopoietic Stem Cell Transplant Membranous Nephropathy Is Associated with Protocadherin FAT1," Presented at the American Society of Nephrology Annual Meeting, Nov. 4, 2021, 2 pages.

Sethi et al., "Hematopoietic Stem Cell Transplant-Membranous Nephropathy Is Associated with Protocadherin FAT1," J. Am. Soc. Nephrol., May 2022, 33(5):1033-1044.

Sethi, "Membranous nephropathy: a single disease or a pattern of injury resulting from different diseases," Clin. Kidney J., Mar. 2021, 14(10):2166-2169.

Sethi, "New 'Antigens' in Membranous Nephropathy," J. Am. Soc. Nephrol., Feb. 2021, 32(2):268-278.

Srinivasan et al., "Nephrotic syndrome: an under-recognised immune-mediated complication of non-myeloablative allogeneic haematopoietic cell transplantation," Br. J. Haematol., Oct. 2005, 131(1):74-79.

Steen et al., "The ABC's (and XYZ's) of peptide sequencing," Nat. Rev. Mol. Cell Biol., Sep. 2004, 5(9):699-711.

Suzuki, "Protocadherins and diversity of the cadherin superfamily," J. Cell Sci., Nov. 1996, 109(Pt. 11):2609-2611.

Troxell et al., "Renal pathology associated with hematopoietic stem cell transplantation," Adv. Anat. Pathol., Sep. 2014, 21(5):330-340.

UniProt Accession No. Q14517, "FAT1_HUMAN," Jul. 5, 2017, 9 pages.

Wojtalwicz et al., "A soluble form of the giant cadherin Fat1 is released from pancreatic cancer cells by ADAM10 mediated ectodomain shedding, " PLoS One, Mar. 2014, 9(3): e90461.

Yaoita et al., "Role of Fat1 in cell-cell contact formation of podocytes in puromycin aminonucleoside nephrosis and neonatal kidney," Kidney Int., Aug. 2005, 68(2):542-551.

Yorioka et al., "Membranous nephropathy with chronic graft-versus-host disease in a bone marrow transplant recipient," Nephron., Nov. 1998, 80(3):371-372.

U.S. Appl. No. 18/843,878, filed Sep. 4, 2024, Sanjeev Sethi, Pending.

* cited by examiner

```
   1 ggcgaccgaa cgcggcggtc ggcagcgttc gcgcggggc  ctgcgaagcg ctgctcgggg
  61 ccggcactgc ccgcggggag gacgcgccgc cgccgccacc cagcgccgcc gccgccgccg
 121 cctccagccg ggccgccgcg cgtcccgggg gccggccccg cgagcgcagg agtaaacacc
 181 gccggagtct tggagccgct gcagaaggga ataaagagag atgcagggat ttgtgaggtt
 241 acggcgcccc agctgcaaga tgcactagcc ggctgaaccc gggatcggct gacttgttgg
 301 aaccggagtg ctctgcacgg agagtggtgg atgagttgaa gttgccttcc cggggctcat
 361 tttccacgct gccgagagga atccgagagg caaggcaatc acttcgtctt gccattgatt
 421 gggtatcggg agctttttt  ttctcccctc tctctttctt ttcctccgtc ttgttgcatg
 481 caagaaaatt acagtccgct gctcgcccgc cctgggtgcg agatattcag ccccgctctc
 541 tcccgtgcat tgtgcaaccc aaagatgaaa gaccgaaggg gagaaagtta agaaatcgc
 601 ccacatgcgc tggatcagtc cacggcttgg ggaaaggcat ccagagaagg tgggagcgga
 661 gagtttgaag tctttacagg cgggaagatg gcggactgga gctgaaagtg ttgattggga
 721 aacttgggtg attcttgtgt ttatttacaa tcctcttgac ccaggcagga cacatgcagg
 781 ccaaaaaacg ctatttcatc ctgctctcag ctggctcttg tctcgccctt ttgttttatt
 841 tcggaggctt gcagtttagg gcatcgagga gccacagccg gagagaagaa cacagcggta
 901 ggaatggctt gcaccacccc agtccggatc atttctggcc ccgcttccg  gacgctctgc
 961 gccccttcgt tccttgggat caattggaaa acgaggattc cagcgtgcac atttccccc
1021 ggcagaagcg agatgccaac tccagcatct acaaaggcaa gaagtgccgc atggagtcct
1081 gcttcgattt caccctttgc aagaaaaacg gcttcaaagt ctacgtatac ccacagcaaa
1141 aaggggagaa aatcgccgaa agttaccaaa acattctagc ggccatcgag ggctccaggt
1201 tctacacctc ggaccccagc caggcgtgcc tctttgtcct gagtctggat actttagaca
1261 gagaccagtt gtcacctcag tatgtgcaca atttgagatc caaagtgcag agtctccact
1321 tgtggaacaa tggtaggaat catttaattt ttaatttata ttccggcact tggcctgact
1381 acaccgagga cgtggggttt gacatcggcc aggcgatgct ggccaaagcc agcatcagta
1441 ctgaaaactt ccgacccaac tttgatgttt ctattcccct cttttctaag gatcatccca
1501 ggacaggagg ggagaggggg ttttgaagt  tcaacaccat ccctcctctc aggaagtaca
1561 tgctggtatt caaggggaag aggtacctga cagggatagg atcagacacc aggaatgcct
1621 tatatcacgt ccataacggg gaggacgttg tgctcctcac cacctgcaag catggcaaag
1681 actggcaaaa gcacaaggat tctcgctgtg acagagacaa caccgagtat gagaagtatg
1741 attatcggga aatgctgcac aatgccactt tctgtctggt tcctcgtggt cgcaggcttg
1801 ggtccttcag attcctggag gctttgcagg ctgcctgcgt cctgtgatg  ctcagcaatg
1861 gatgggagtt gccattctct gaagtgatta attggaacca agctgccgtc ataggcgatg
1921 agagattgtt attacagatt ccttctacaa tcaggtctat tcatcaggat aaaatcctag
1981 cacttagaca gcagacacaa ttcttgtggg aggcttattt ttcttcagtt gagaagattg
2041 tattaactac actagagatt attcaggaca gaatattcaa gcacatatca cgtaacagtt
2101 taatatggaa caaacatcct ggaggattgt tcgtactacc acagtattca tcttatctgg
2161 gagattttcc ttactactat gctaatttag gtttaaagcc cccctccaaa ttcactgcag
2221 tcatccatgc ggtgaccccc ctggtctctc agtcccagcc agtgttgaag cttctcgtgg
2281 ctgcagccaa gtcccagtac tgtgcccaga tcatagttct atggaattgt gacaagcccc
2341 taccagccaa acaccgctgg cctgccactg ctgtgcctgt cgtcgtcatt gaaggagaga
2401 gcaaggttat gagcagccgt tttctgccct acgacaacat catcacagac gccgtgctca
2461 gccttgacga ggacacggtg ctttcaacaa cagaggtgga tttcgccttc acagtgtggc
2521 agagcttccc tgagaggatt gtggggtacc ccgcgcgcag ccacttctgg gataactcta
2581 aggagcggtg gggatacaca tcaaagtgga cgaacgacta ctccatggtg ttgacaggag
2641 ctgctattta ccacaaatat tatcactacc tatactccca ttacctgcca gccagcctga
2701 agaacatggt ggaccaattg ccaattgtg  aggacattct catgaacttc ctggtgtctg
2761 ctgtgacaaa attgcctcca atcaaagtga cccagaagaa gcagtataag gagacaatga
2821 tgggacagac ttctcgggct tcccgttggg ctgaccctga ccactttgcc cagcgacaga
2881 gctgcatgaa tacgtttgcc agctggtttg gctacatgcc gctgatccac tctcagatga
2941 ggctcgaccc cgtcctcttt aaagaccagg tctctatttt gaggaagaaa taccgagaca
3001 ttgagcgact ttgaggaatc cggctgagtg ggggagggga agcaagaagg gatggggtc
3061 aagctgctct ctcttcccag tgcagatcca ctcatcagca gagccagatt gtgccaacta
3121 tccaaaaact tagatgagca gaatgacaaa aaaaaaaagg ccaatgagaa ctcaactcct
3181 ggctcctggg actgcaccag actgctccaa actcacctca ctggcttctg tgtcccaaga
```

FIG. 1

```
3241 ctaggttgtg tacagtttaa ttatggaaca ttaaataatt attttgaaa  tgattgctat
3301 gcaggtttaa acttttttaa tgatcaaaaac tattaaaaaac cagagttctt tgtttaatca
3361 aaaaaaaaaa aaaaaa (SEQ ID NO:1)

1 mqakkryfil isagsclall fyfgglqfra srshsrreeh sgrnglhhps pdhfwprfpd
 61 airpfvpwdq lenedssvhi sprqkrdans siykgkkcrm escfdftick kngfkvyvyp
121 qqkgekiaes yqnilaaieg srfytsdpsq aclfvisldt ldrdqlspqy vhnirskvqs
181 lhiwnngrnh lifnlysgtw pdytedvgfd iggamlakas istenfrpnf dvsiplfskd
241 hprtggergf ikfntipplr kymlvfkgkr yltgigsdtr nalyhvhnge dvvilttckh
301 gkdwqkhkds rcdrdnteye kydyremlhn atfclvprgr rlgsfrflea lqaacvpvml
361 snqwelpfse vinwnqaavi gderillqip stirsihqdk ilalrqgtqf lweayfssve
421 kivlttieii qdrifkhisr nsliwnkhpg qlfvlpqyss ylgdfpyyya nigikppskf
481 tavihavtpl vsqsqpvlkl ivaaaksqyc aqiivlwncd kpipakhrwp atavpvvvie
541 geskvmssrf lpydniitda vlsldedtvl sttevdfaft vwqsfperiv gyparshfwd
601 nskerwgyts kwtndysmvl tgaaiyhkyy hylyshylpa slknmvdqia ncedilmnfl
661 vsavtkippi kvtqkkqyke tmmgqtsras rwadpdhfaq rqscmntfas wfgymplihs
721 qmrldpvlfk dqvsilrkky rdierl (SEQ ID NO:2)
```

FIG. 1 (cont)

```
   1 ctgtctgagc atttcactgc ggagcctgag cgcgcctgcc tgggaaaaca ctgcagcggt
  61 gctcggactc ctcctgtcca gcaggaggcg cggcccggca gctcccgcat gcgcagtgcg
 121 ctcggtgtca gacggcccgg atcccggtta ccggcccctc gctcgctgct cgccagccca
 181 gactcggccc tggcagtggc ggctggcgat tcggaccgat ccgacctggg cggaggtggc
 241 ccgcgccccg cggcatgagc cggtgaccaa gctcggggcc gagcgggagg cagccgtggc
 301 cgaggagtgt gaggaagagg ctgtctgtgt cattatgtgt gcgtcggtca agtataatat
 361 ccggggtcct gccctcatcc caagaatgaa gaccaagcac cgaatctact atatcaccct
 421 cttctccatt gtcctcctgg gcctcattgc cactggcatg tttcagtttt ggccccattc
 481 tatcgagtcc tcaaatgact ggaatgtaga gaagcgcagc atccgtgatg tgccggttgt
 541 taggctgcca gccgacagtc ccatcccaga gcgggggat ctcagttgca gaatgcacac
 601 gtgttttgat gtctatcgct gtggcttcaa cccaaagaac aaaatcaagg tgtatatcta
 661 tgctctgaaa agtacgtgg atgactttgg cgtctctgtc agcaacacca tctcccggga
 721 gtataatgaa ctgctcatgg ccatctcaga cagtgactac tacactgatg acatcaaccg
 781 ggcctgtctg tttgttccct ccatcgatgt gcttaaccag aacacactgc gcatcaagga
 841 gacagcacaa gcgatggccc agctctctag gtgggatcga ggtacgaatc acctgttgtt
 901 caacatgttg cctggaggtc ccccagatta taacacagcc tggatgtcc ccagagacag
 961 ggccctgttg gctggtggcg cttttctac gtggacttac ggcaaggct acgatgtcag
1021 cattcctgtc tatagtccac tgtcagctga ggtggatctt ccagagaaag gaccaggtcc
1081 acggcaatac ttcctcctgt catctcaggt gggtctccat cctgagtaca gagaggacct
1141 agaagccctc aggtcaaaac atggagagtc agtgttagta ctcgataaat gcaccaacct
1201 ctcagagggt gtcctttctg tccgtaagcg ctgccacaag caccaggtct tcgattaccc
1261 acaggtgcta caggaggcta ctttctgtgt ggttcttcgt ggagctcggc tgggccaggc
1321 agtattgagc gatgtgttac aagctggctg tgtcccggtt gtcattgcag actcctatat
1381 tttgcctttc tctgaagttc ttgactggaa gagagcatct gtggttgtac cagaagaaaa
1441 gatgtcagat gtgtacagta ttttgcagag catcccccaa agacagattg aagaaatgca
1501 gagacaggcc cggtggttct gggaagcgta cttccagtca attaaagcca ttgccctggc
1561 caccctgcag attatcaatg accggatcta tccatatgct gccatctcct atgaagaatg
1621 gaatgaccct cctgctgtga agtggggcag cgtgagcaat ccactcttcc tcccgctgat
1681 cccaccacag tctcaaggt tcaccgccat agtcctcacc tacgaccgag tagagagcct
1741 cttccgggtc atcactgaag tgtccaaggt gcccagtcta tccaaactac ttgtcgtctg
1801 gaataatcag aataaaaacc ctccagaaga ttctctctgg cccaaaatcc gggttccatt
1861 aaaagttgtg aggactgctg aaaacaagtt aagtaaccgt ttcttccctt atgatgaaat
1921 cgagacagaa gctgttctgg ccattgatga tgatatcatt atgctgacct ctgacgagct
1981 gcaatttggt tatgaggtct ggcgggaatt tcctgaccgg ttggtgggtt acccgggtcg
2041 tctgcatctc tgggaccatg agatgaataa gtggaagtat gagtctgagt ggacgaatga
2101 agtgtccatg gtgctcactg ggcagctttt tatcacaag tattttaatt acctgtatac
2161 ctacaaaatg cctggggata tcaagaactg ggtagatgct catatgaact gtgaagatat
2221 tgccatgaac ttcctggtgg ccaacgtcac gggaaaagca gttatcaagg taaccccacg
2281 aaagaaattc aagtgtcctg agtgcacagc catagatggg ctttcactag accaaacaca
2341 catggtggag aggtcagagt gcatcaacaa gtttgcttca gtcttcggga ccatgcctct
2401 caaggtggtg aacaccgag ctgaccctgt cctgtacaaa gatgactttc ctgagaagct
2461 gaagagcttc ccaacattg gcagcttatg aaacgtgtca ttggtggagg tctgaatgtg
2521 aggctggac agagggagag aacaaggcct cccagcactc tgatgtcaga gtagtaggtt
2581 aagggtggaa ggttgaccta cttggatctt ggcatgcacc acctaaccc actttctcaa
2641 gaacaagaac ctagaatgaa atccaagca cctcgagcta tgcaacctct gttcttgtat
2701 ttcttatgat ctctgatggg ttcttctcga aaatgccaag tggaagactt tgtggcatgc
2761 tccagattta aatccagctg aggctcccct tgttttcagt tccatgtaac aatctggaag
2821 gaaacttcac ggacaggaag actgctggag aagagaagcg tgttagccca tttgaggtct
2881 ggggaatcat gtaaagggta cccagacctc acttttagtt atttacatca atgagttctt
2941 tcagggaacc aaacccagaa ttcggtgcaa aagccaaaca tcttggtggg atttgataaa
```

FIG. 2

```
3001 tgccttggga cctggagtgc tgggcttgtg cacaggaaga gcaccagccg ctgagtcagg
3061 atcctgtcag ttccatgagc tattcctctt tggtttggct ttttgatatg attaaaatta
3121 tttttattc cttttaaaaa aaaaaaaaaa aaaaaaatt cgtcgtgctt aaaca (SEQ
     ID NO:3)

1 mcasvkynir gpaliprmkt khriyyitlf sivllgliat gmfqfwphsi essndwnvek
 61 rsirdvpvvr lpadspiper gdlscrmhtc fdvyrcgfnp knkikvyiya lkkyvddfgv
121 svsntisrey nellmaisds dyytddinra clfvpsidvl nqntlriket aqamaqlsrw
181 drgtnhllfn mlpggppdyn taldvprdra llagggfstw tyrqgydvsi pvysplsaev
241 dlpekgpgpr qyfllssqvg lhpeyredle alqvkhgesv lvldkctnls egvlsvrkrc
301 hkhqvfdypq vlqeatfcvv lrgarlgqav lsdvlqagcv pvviadsyil pfsevldwkr
361 asvvvpeekm sdvysilqsi pqrqieemqr qarwfweayf qsikaialat lqiindriyp
421 yaaisyeewn dppavkwgsv snplflplip pqsqgftaiv ltydrveslf rvitevskvp
481 slskllvvwn nqnknppeds lwpkirvplk vvrtaenkls nrffpydeie teavlaiddd
541 iimltsdelq fgyevwrefp drlvgypgrl hlwdhemnkw kyesewtnev smvltgaafy
601 hkyfnylyty kmpgdiknwv dahmncedia mnflvanvtg kavikvtprk kfkcpectai
661 dglsldqthm versecinkf asvfgtmplk vvehradpvl ykddfpeklk sfpnigsl
     (SEQ ID NO:4)
```

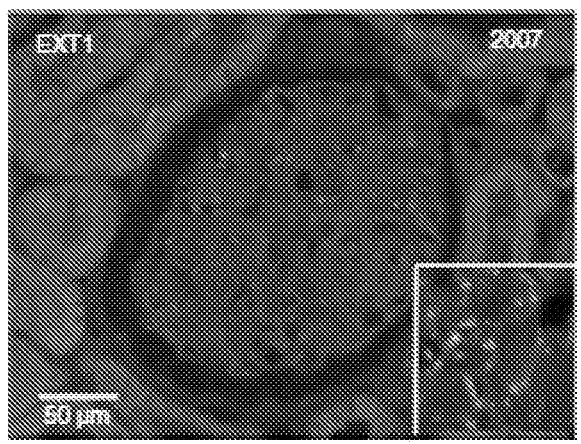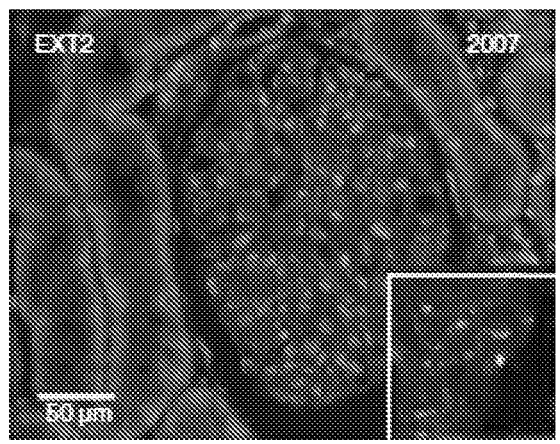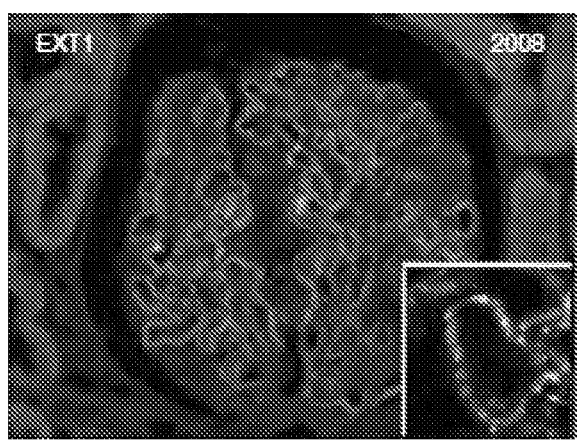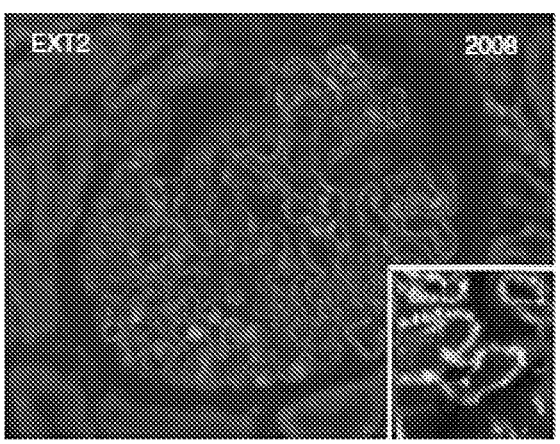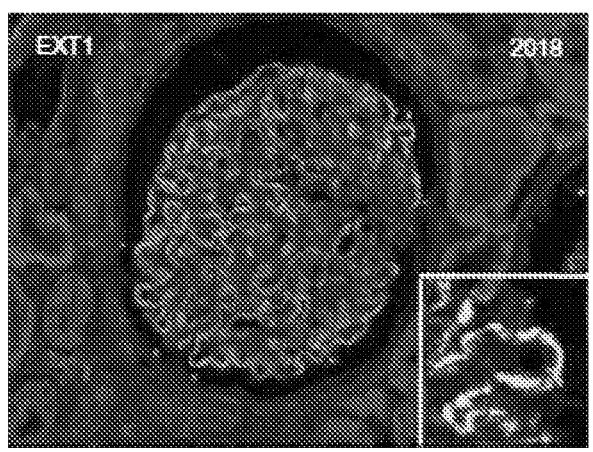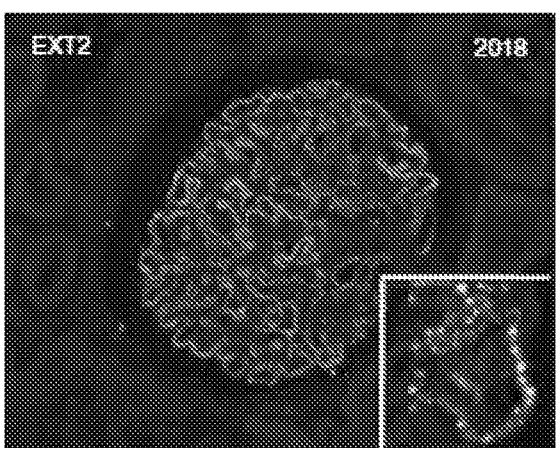
FIG. 6

FIG. 14

Bio View:
2323 Proteins in 2107 Clusters
With 2321 Filtered Out

Probability Legend:
- over 95%
- 80% to 94%
- 50% to 79%
- 20% to 49%
- 0% to 19%

| Identified Proteins | Accession Number | Molecular Weight | Protein Grouping Ambiguity | Diabetes Case 1 | Diabetes Case 2 | IgA Case 1 | IgA Case 2 | Primary FSGS Case 1 | Primary FSGS Case 2 | MCD Case 1 | MCD Case 2 | PLA2R negative Case 1 | PLA2R negative Case 2 |
|---|---|---|---|---|---|---|---|---|---|---|---|---|---|
| Exostosin-2 OS=Homo sapiens GN=EXT2 PE=1 SV=1 | sp\|Q93063\| | 82 kDa | | (0) | (0) | (0) | (0) | (0) | (0) | (0) | (0) | (0) | (0) |
| Exostosin-1 OS=Homo sapiens GN=EXT1 PE=1 SV=2 | sp\|Q16394\| | 86 kDa | ☆ | (0) | (0) | (0) | (0) | (0) | (0) | (0) | (0) | (0) | (0) |
| Secretory phospholipase A2 receptor OS=Homo sapiens GN=PLA2R1 PE=1 S... | sp\|Q13018\|P... | 169 kDa | ☆ | 5 | 3 | 2 | 4 | 3 | 3 | 0 | (0) | 3 | 4 |
| Laminin subunit beta-2 OS=Homo sapiens GN=LAMB2 PE=1 SV=2 | sp\|P55268\|L... | 196 kDa | ☆ | 161 | 166 | 230 | 176 | 154 | 239 | 224 | 188 | 205 | 128 |
| Nestin OS=Homo sapiens GN=NES PE=1 SV=2 | sp\|P48681\| | 177 kDa | ☆ | 81 | 74 | 93 | 97 | 100 | 133 | 163 | 177 | 90 | 102 |
| Nidogen-1 OS=Homo sapiens GN=NID1 PE=1 SV=3 | sp\|P14543\| | 136 kDa | ☆ | 78 | 90 | 113 | 86 | 96 | 101 | 98 | 87 | 146 | 90 |
| Vinculin OS=Homo sapiens GN=VCL PE=1 SV=4 | sp\|P18206\| | 124 kDa | ☆ | 75 | 77 | 91 | 89 | 106 | 103 | 119 | 129 | 147 | 78 |
| Heat shock protein HSP 90-alpha OS=Homo sapiens GN=HSP90AA1 PE=1... | sp\|P07900\|H... | 85 kDa | ☆ | 35 | 31 | 29 | 30 | 32 | 47 | 36 | 26 | 19 | 32 |
| Heat shock protein HSP 90-beta OS=Homo sapiens GN=HSP90AB1 PE=1 S... | sp\|P08238\|H... | 83 kDa | ☆ | 31 | 31 | 28 | 29 | 37 | 33 | 38 | 35 | 21 | 30 |
| Glyceraldehyde-3-phosphate dehydrogenase OS=Homo sapiens GN=GAP... | sp\|P04406\| | 36 kDa | ☆ | 35 | 41 | 44 | 37 | 35 | 47 | 67 | 65 | 35 | 40 |

SEQUENCE LISTING

<160> NUMBER OF SEQ ID NOS: 5

<210> SEQ ID NO 1
<211> LENGTH: 3376
<212> TYPE: DNA
<213> ORGANISM: human

<400> SEQUENCE: 1

```
ggcgaccgaa cgcggcggtc ggcagcgttc gcgcggggggc ctgcgaagcg ctgctcgggg      60
ccggcactgc ccgcggggag gacgcgccgc cgccgccacc cagcgccgcc gccgccgccg     120
cctccagccg ggccgccgcg cgtcccgggg gccggccccg cgagcgcagg agtaaacacc     180
gccggagtct tggagccgct gcagaaggga ataaagagag atgcagggat ttgtgaggtt     240
acggcgcccc agctgcaaga tgcactagcc ggctgaaccc gggatcggct gacttgttgg     300
aaccggagtg ctctgcacgg agagtggtgg atgagttgaa gttgccttcc cgggggctcat    360 tttccacgct gccgagagga atccgagagg caaggcaatc acttcgtctt gccattgatt     420
gggtatcggg agctttttttt ttctcccctc tctctttctt ttcctccgtc ttgttgcatg    480
caagaaaatt acagtccgct gctcgcccgc cctgggtgcg agatattcag ccccgctctc     540
tcccgtgcat tgtgcaaccc aaagatgaaa gaccgaaggg gagaaagtta agaaaatcgc     600
ccacatgcgc tggatcagtc cacggcttgg ggaaaggcat ccagagaagg tgggagcgga     660
gagtttgaag tcttttacagg cgggaagatg gcggactgga gctgaaagtg ttgattggga    720
aacttgggtg attcttgtgt ttatttacaa tcctcttgac ccaggcagga cacatgcagg     780
ccaaaaaacg ctatttcatc ctgctctcag ctggctcttg tctcgcccctt ttgttttatt    840 tcggaggctt gcagtttagg gcatcgagga gccacagccg gagagaagaa cacagcggta     900
ggaatggctt gcaccacccc agtccggatc atttctggcc ccgcttcccg gacgctctgc     960
gccccttcgt tccttgggat caattggaaa acgaggattc cagcgtgcac atttcccccc    1020
ggcagaagcg agatgccaac tccagcatct acaaaggcaa gaagtgccgc atggagtcct    1080
gcttcgattt cacccctttgc aagaaaaacg gcttcaaagt ctacgtatac ccacagcaaa    1140 aagggggagaa atcgccgaaa agttaccaaa acattctagc ggccatcgag ggctccaggt    1200
tctacacctc ggaccccagc caggcgtgcc tctttgtcct gagtctggat actttagaca    1260
gagaccagtt gtcacctcag tatgtgcaca atttgagatc caaagtgcag agtctccact    1320
tgtggaacaa tggtaggaat catttaattt ttaatttata ttccggcact tggcctgact    1380
acaccgagga cgtggggttt gacatcggcc aggcgatgct ggccaaagcc agcatcagta    1440
ctgaaaactt ccgacccaac tttgatgttt ctattcccct cttttctaag gatcatccca    1500
ggacaggagg ggagaggggg ttttgaagt tcaacaccat ccctcctctc aggaagtaca     1560
tgctggtatt caaggggaag aggtacctga cagggatagg atcagacacc aggaatgcct    1620
tatatcacgt ccataacggg gaggacgttg tgctcctcac cacctgcaag catggcaaag    1680
actggcaaaa gcacaaggat tctcgctgtg acagagacaa caccgagtat gagaagtatg    1740
attatcggga aatgctgcac aatgccactt tctgtctggt tcctcgtggt cgcaggcttg    1800
ggtccttcag attcctggag gctttgcagg ctgcctgcgt ccctgtgatg ctcagcaatg    1860
```

-continued

```
gatgggagtt gccattctct gaagtgatta attggaacca agctgccgtc ataggcgatg    1920
agagattgtt attacagatt ccttctacaa tcaggtctat tcatcaggat aaaatcctag    1980
cacttagaca gcagacacaa ttcttgtggg aggcttattt ttcttcagtt gagaagattg    2040
tattaactac actagagatt attcaggaca gaatattcaa gcacatatca cgtaacagtt    2100
taatatggaa caaacatcct ggaggattgt tcgtactacc acagtattca tcttatctgg    2160
gagattttcc ttactactat gctaatttag gtttaaagcc cccctccaaa ttcactgcag    2220
tcatccatgc ggtgaccccc ctggtctctc agtcccagcc agtgttgaag cttctcgtgg    2280
ctgcagccaa gtcccagtac tgtgcccaga tcatagttct atggaattgt gacaagcccc    2340
taccagccaa acaccgctgg cctgccactg ctgtgcctgt cgtcgtcatt gaaggagaga    2400
gcaaggttat gagcagccgt tttctgccct acgacaacat catcacagac gccgtgctca    2460
gccttgacga ggacacggtg ctttcaacaa cagaggtgga tttcgccttc acagtgtggc    2520
agagcttccc tgagaggatt gtggggtacc ccgcgcgcag ccacttctgg gataactcta    2580
aggagcggtg gggatacaca tcaaagtgga cgaacgacta ctccatggtg ttgacaggag    2640
ctgctattta ccacaaatat tatcactacc tatactccca ttacctgcca gccagcctga    2700
agaacatggt ggaccaattg gccaattgtg aggacattct catgaacttc ctggtgtctg    2760
ctgtgacaaa attgcctcca atcaaagtga cccagaagaa gcagtataag gagacaatga    2820
tgggacagac ttctcgggct tcccgttggg ctgaccctga ccactttgcc cagcgacaga    2880
gctgcatgaa tacgtttgcc agctggtttg gctacatgcc gctgatccac tctcagatga    2940
ggctcgaccc cgtcctcttt aaagaccagg tctctatttt gaggaagaaa taccgagaca    3000
ttgagcgact ttgaggaatc cggctgagtg ggggagggga agcaagaagg gatggggtc     3060 aagctgctct ctcttcccag tgcagatcca ctcatcagca gagccagatt gtgccaacta    3120
tccaaaaact tagatgagca gaatgacaaa aaaaaaaagg ccaatgagaa ctcaactcct    3180
ggctcctggg actgcaccag actgctccaa actcacctca ctggcttctg tgtcccaaga    3240
ctaggttgtg tacagtttaa ttatggaaca ttaaataatt attttttgaaa tgattgctat    3300 gcaggtttaa acttttttaa tgatcaaaac tattaaaaac cagagttctt tgtttaatca    3360
aaaaaaaaaa aaaaaa                                                    3376
```

<210> SEQ ID NO 2
<211> LENGTH: 746
<212> TYPE: PRT
<213> ORGANISM: human

<400> SEQUENCE: 2

```
Met Gln Ala Lys Lys Arg Tyr Phe Ile Leu Leu Ser Ala Gly Ser Cys
1               5                   10                  15

Leu Ala Leu Leu Phe Tyr Phe Gly Gly Leu Gln Phe Arg Ala Ser Arg
            20                  25                  30

Ser His Ser Arg Arg Glu Glu His Ser Gly Arg Asn Gly Leu His His
        35                  40                  45

Pro Ser Pro Asp His Phe Trp Pro Arg Phe Pro Asp Ala Leu Arg Pro
    50                  55                  60

Phe Val Pro Trp Asp Gln Leu Glu Asn Glu Asp Ser Ser Val His Ile
65                  70                  75                  80

Ser Pro Arg Gln Lys Arg Asp Ala Asn Ser Ser Ile Tyr Lys Gly Lys
                85                  90                  95

Lys Cys Arg Met Glu Ser Cys Phe Asp Phe Thr Leu Cys Lys Lys Asn
```

```
                100                 105                 110
Gly Phe Lys Val Tyr Val Tyr Pro Gln Gln Lys Gly Glu Lys Ile Ala
            115                 120                 125

Glu Ser Tyr Gln Asn Ile Leu Ala Ala Ile Glu Gly Ser Arg Phe Tyr
        130                 135                 140

Thr Ser Asp Pro Ser Gln Ala Cys Leu Phe Val Leu Ser Leu Asp Thr
145                 150                 155                 160

Leu Asp Arg Asp Gln Leu Ser Pro Gln Tyr Val His Asn Leu Arg Ser
                165                 170                 175

Lys Val Gln Ser Leu His Leu Trp Asn Asn Gly Arg Asn His Leu Ile
            180                 185                 190

Phe Asn Leu Tyr Ser Gly Thr Trp Pro Asp Tyr Thr Glu Asp Val Gly
        195                 200                 205

Phe Asp Ile Gly Gln Ala Met Leu Ala Lys Ala Ser Ile Ser Thr Glu
    210                 215                 220

Asn Phe Arg Pro Asn Phe Asp Val Ser Ile Pro Leu Phe Ser Lys Asp
225                 230                 235                 240

His Pro Arg Thr Gly Gly Glu Arg Gly Phe Leu Lys Phe Asn Thr Ile
                245                 250                 255

Pro Pro Leu Arg Lys Tyr Met Leu Val Phe Lys Gly Lys Arg Tyr Leu
            260                 265                 270

Thr Gly Ile Gly Ser Asp Thr Arg Asn Ala Leu Tyr His Val His Asn
        275                 280                 285

Gly Glu Asp Val Val Leu Leu Thr Thr Cys Lys His Gly Lys Asp Trp
    290                 295                 300

Gln Lys His Lys Asp Ser Arg Cys Asp Arg Asp Asn Thr Glu Tyr Glu
305                 310                 315                 320

Lys Tyr Asp Tyr Arg Glu Met Leu His Asn Ala Thr Phe Cys Leu Val
                325                 330                 335

Pro Arg Gly Arg Arg Leu Gly Ser Phe Arg Phe Leu Glu Ala Leu Gln
            340                 345                 350

Ala Ala Cys Val Pro Val Met Leu Ser Asn Gly Trp Glu Leu Pro Phe
        355                 360                 365

Ser Glu Val Ile Asn Trp Asn Gln Ala Ala Val Ile Gly Asp Glu Arg
    370                 375                 380

Leu Leu Leu Gln Ile Pro Ser Thr Ile Arg Ser Ile His Gln Asp Lys
385                 390                 395                 400

Ile Leu Ala Leu Arg Gln Gln Thr Gln Phe Leu Trp Glu Ala Tyr Phe
                405                 410                 415

Ser Ser Val Glu Lys Ile Val Leu Thr Thr Leu Glu Ile Ile Gln Asp
            420                 425                 430

Arg Ile Phe Lys His Ile Ser Arg Asn Ser Leu Ile Trp Asn Lys His
        435                 440                 445

Pro Gly Gly Leu Phe Val Leu Pro Gln Tyr Ser Ser Tyr Leu Gly Asp
    450                 455                 460

Phe Pro Tyr Tyr Tyr Ala Asn Leu Gly Leu Lys Pro Pro Ser Lys Phe
465                 470                 475                 480

Thr Ala Val Ile His Ala Val Thr Pro Leu Val Ser Gln Ser Gln Pro
                485                 490                 495

Val Leu Lys Leu Leu Val Ala Ala Lys Ser Gln Tyr Cys Ala Gln
            500                 505                 510

Ile Ile Val Leu Trp Asn Cys Asp Lys Pro Leu Pro Ala Lys His Arg
        515                 520                 525
```

Trp Pro Ala Thr Ala Val Pro Val Val Ile Glu Gly Glu Ser Lys
            530                 535                 540

Val Met Ser Ser Arg Phe Leu Pro Tyr Asp Asn Ile Ile Thr Asp Ala
545                 550                 555                 560

Val Leu Ser Leu Asp Glu Asp Thr Val Leu Ser Thr Thr Glu Val Asp
                565                 570                 575

Phe Ala Phe Thr Val Trp Gln Ser Phe Pro Glu Arg Ile Val Gly Tyr
            580                 585                 590

Pro Ala Arg Ser His Phe Trp Asp Asn Ser Lys Glu Arg Trp Gly Tyr
            595                 600                 605

Thr Ser Lys Trp Thr Asn Asp Tyr Ser Met Val Leu Thr Gly Ala Ala
            610                 615                 620

Ile Tyr His Lys Tyr Tyr His Tyr Leu Tyr Ser His Tyr Leu Pro Ala
625                 630                 635                 640

Ser Leu Lys Asn Met Val Asp Gln Leu Ala Asn Cys Glu Asp Ile Leu
            645                 650                 655

Met Asn Phe Leu Val Ser Ala Val Thr Lys Leu Pro Pro Ile Lys Val
            660                 665                 670

Thr Gln Lys Lys Gln Tyr Lys Glu Thr Met Met Gly Gln Thr Ser Arg
            675                 680                 685

Ala Ser Arg Trp Ala Asp Pro Asp His Phe Ala Gln Arg Gln Ser Cys
690                 695                 700

Met Asn Thr Phe Ala Ser Trp Phe Gly Tyr Met Pro Leu Ile His Ser
705                 710                 715                 720

Gln Met Arg Leu Asp Pro Val Leu Phe Lys Asp Gln Val Ser Ile Leu
            725                 730                 735

Arg Lys Lys Tyr Arg Asp Ile Glu Arg Leu
            740                 745

<210> SEQ ID NO 3
<211> LENGTH: 3175
<212> TYPE: DNA
<213> ORGANISM: human

<400> SEQUENCE: 3
ctgtctgagc atttcactgc ggagcctgag cgcgcctgcc tgggaaaaca ctgcagcggt      60
gctcggactc tcctgtcca gcaggaggcg cggcccggca gctcccgcat gcgcagtgcg     120
ctcggtgtca gacggcccgg atccggtta ccggcccctc gctcgctgct cgccagccca     180
gactcggccc tggcagtggc ggctggcgat tcgaccgat ccgacctggg cggaggtggc     240
ccgcgccccg cggcatgagc cggtgaccaa gctcggggcc gagcgggagg cagccgtggc     300
cgaggagtgt gaggaagagg ctgtctgtgt cattatgtgt gcgtcggtca agtataaatat    360
ccggggtcct gccctcatcc aagaatgaa gaccaagcac cgaatctact atatcaccct     420
cttctccatt gtcctcctgg gcctcattgc cactggcatg tttcagttttt ggccccattc     480
tatcgagtcc tcaaatgact ggaatgtaga gaagcgcagc atccgtgatg tgccggttgt     540
taggctgcca gccgacagtc ccatcccaga gcgggggggat ctcagttgca gaatgcacac     600
gtgttttgat gtctatcgct gtggcttcaa cccaaagaac aaaatcaagg tgtatatcta     660
tgctctgaaa aagtacgtgg atgactttgg cgtctctgtc agcaacacca tctcccggga     720
gtataatgaa ctgctcatgg ccatctcaga cagtgactac tacactgatg acatcaaccg     780
ggcctgtctg tttgttccct ccatcgatgt gcttaaccag aacacactgc gcatcaagga     840

-continued

```
gacagcacaa gcgatggccc agctctctag gtgggatcga ggtacgaatc acctgttgtt      900
caacatgttg cctggaggtc ccccagatta taacacagcc ctggatgtcc ccagagacag      960
ggccctgttg gctggtggcg gcttttctac gtggacttac cggcaaggct acgatgtcag     1020
cattcctgtc tatagtccac tgtcagctga ggtggatctt ccagagaaag gaccaggtcc     1080
acggcaatac ttcctcctgt catctcaggt gggtctccat cctgagtaca gagaggacct     1140
agaagccctc caggtcaaac atggagagtc agtgttagta ctcgataaat gcaccaacct     1200
ctcagagggt gtcctttctg tccgtaagcg ctgccacaag caccaggtct tcgattaccc     1260
acaggtgcta caggaggcta ctttctgtgt ggttcttcgt ggagctcggc tgggccaggc     1320
agtattgagc gatgtgttac aagctggctg tgtcccggtt gtcattgcag actcctatat     1380
tttgcctttc tctgaagttc ttgactggaa gagagcatct gtggttgtac cagaagaaaa     1440
gatgtcagat gtgtacagta ttttgcagag catcccccaa agacagattg aagaaatgca     1500
gagacaggcc cggtggttct gggaagcgta cttccagtca attaaagcca ttgccctggc     1560
caccctgcag attatcaatg accggatcta tccatatgct gccatctcct atgaagaatg     1620
gaatgaccct cctgctgtga agtggggcag cgtgagcaat ccactcttcc tcccgctgat     1680
cccaccacag tctcaagggt tcaccgccat agtcctcacc tacgaccgag tagagagcct     1740
cttccgggtc atcactgaag tgtccaaggt gcccagtcta tccaaactac ttgtcgtctg     1800
gaataatcag aataaaaacc ctccagaaga ttctctctgg cccaaaatcc gggttccatt     1860
aaaagttgtg aggactgctg aaaacaagtt aagtaaccgt ttcttccctt atgatgaaat     1920
cgagacagaa gctgttctgg ccattgatga tgatatcatt atgctgacct ctgacgagct     1980
gcaatttggt tatgaggtct ggcgggaatt tcctgaccgg ttggtgggtt acccgggtcg     2040
tctgcatctc tgggaccatg agatgaataa gtggaagtat gagtctgagt ggacgaatga     2100
agtgtccatg gtgctcactg gggcagcttt ttatcacaag tattttaatt acctgtatac     2160
ctacaaaatg cctgggggata tcaagaactg ggtagatgct catatgaact gtgaagatat     2220
tgccatgaac ttcctggtgg ccaacgtcac gggaaaagca gttatcaagg taaccccacg     2280
aaagaaattc aagtgtcctg agtgcacagc catagatggg cttttcactag accaaacaca     2340
catggtggag aggtcagagt gcatcaacaa gtttgcttca gtcttcggga ccatgcctct     2400
caaggtggtg gaacaccgag ctgaccctgt cctgtacaaa gatgactttc ctgagaagct     2460
gaagagcttc cccaacattg gcagcttatg aaacgtgtca ttggtggagg tctgaatgtg     2520
aggctgggac agagggagag aacaaggcct cccagcactc tgatgtcaga gtagtaggtt     2580
aagggtggaa ggttgaccta cttggatctt ggcatgcacc cacctaaccc actttctcaa     2640
gaacaagaac ctagaatgaa tatccaagca cctcgagcta tgcaacctct gttcttgtat     2700
ttcttatgat ctctgatggg ttcttctcga aaatgccaag tggaagactt tgtggcatgc     2760
tccagattta aatccagctg aggctcccctt tgttttcagt tccatgtaac aatctggaag     2820
gaaacttcac ggacaggaag actgctggag aagagaagcg tgttagccca tttgaggtct     2880
ggggaatcat gtaaagggta cccagacctc actttttagtt atttacatca atgagttctt     2940
tcagggaacc aaacccagaa ttcggtgcaa aagccaaaca tcttggtggg atttgataaa     3000
tgccttggga cctggagtgc tgggcttgtg cacaggaaga gcaccagccg ctgagtcagg     3060
atcctgtcag ttccatgagc tattcctctt tggtttggct ttttgatatg attaaaatta     3120
tttttttattc cttttaaaaa aaaaaaaaa aaaaaaaatt cgtcgtgctt aaaca         3175
```

```
<210> SEQ ID NO 4
<211> LENGTH: 718
<212> TYPE: PRT
<213> ORGANISM: human

<400> SEQUENCE: 4
```

| | | | | | | | | | | | | | | |
|---|---|---|---|---|---|---|---|---|---|---|---|---|---|---|
| Met | Cys | Ala | Ser | Val | Lys | Tyr | Asn | Ile | Arg | Gly | Pro | Ala | Leu | Ile | Pro |
| 1 | | | | 5 | | | | | 10 | | | | | 15 | |
| Arg | Met | Lys | Thr | Lys | His | Arg | Ile | Tyr | Tyr | Ile | Thr | Leu | Phe | Ser | Ile |
| | | | 20 | | | | | 25 | | | | | 30 | | |
| Val | Leu | Leu | Gly | Leu | Ile | Ala | Thr | Gly | Met | Phe | Gln | Phe | Trp | Pro | His |
| | | 35 | | | | | 40 | | | | | 45 | | | |
| Ser | Ile | Glu | Ser | Ser | Asn | Asp | Trp | Asn | Val | Glu | Lys | Arg | Ser | Ile | Arg |
| | 50 | | | | | 55 | | | | | 60 | | | | |
| Asp | Val | Pro | Val | Val | Arg | Leu | Pro | Ala | Asp | Ser | Pro | Ile | Pro | Glu | Arg |
| 65 | | | | | 70 | | | | | 75 | | | | | 80 |
| Gly | Asp | Leu | Ser | Cys | Arg | Met | His | Thr | Cys | Phe | Asp | Val | Tyr | Arg | Cys |
| | | | | 85 | | | | | 90 | | | | | 95 | |
| Gly | Phe | Asn | Pro | Lys | Asn | Lys | Ile | Lys | Val | Tyr | Ile | Tyr | Ala | Leu | Lys |
| | | | 100 | | | | | 105 | | | | | 110 | | |
| Lys | Tyr | Val | Asp | Asp | Phe | Gly | Val | Ser | Val | Ser | Asn | Thr | Ile | Ser | Arg |
| | | | 115 | | | | | 120 | | | | | 125 | | |
| Glu | Tyr | Asn | Glu | Leu | Leu | Met | Ala | Ile | Ser | Asp | Ser | Asp | Tyr | Tyr | Thr |
| | 130 | | | | | 135 | | | | | 140 | | | | |
| Asp | Asp | Ile | Asn | Arg | Ala | Cys | Leu | Phe | Val | Pro | Ser | Ile | Asp | Val | Leu |
| 145 | | | | | 150 | | | | | 155 | | | | | 160 |
| Asn | Gln | Asn | Thr | Leu | Arg | Ile | Lys | Glu | Thr | Ala | Gln | Ala | Met | Ala | Gln |
| | | | | 165 | | | | | 170 | | | | | 175 | |
| Leu | Ser | Arg | Trp | Asp | Arg | Gly | Thr | Asn | His | Leu | Leu | Phe | Asn | Met | Leu |
| | | | 180 | | | | | 185 | | | | | 190 | | |
| Pro | Gly | Gly | Pro | Pro | Asp | Tyr | Asn | Thr | Ala | Leu | Asp | Val | Pro | Arg | Asp |
| | | | 195 | | | | | 200 | | | | | 205 | | |
| Arg | Ala | Leu | Leu | Ala | Gly | Gly | Phe | Ser | Thr | Trp | Thr | Tyr | Arg | Gln |
| | 210 | | | | | 215 | | | | | 220 | | | | |
| Gly | Tyr | Asp | Val | Ser | Ile | Pro | Val | Tyr | Ser | Pro | Leu | Ser | Ala | Glu | Val |
| 225 | | | | | 230 | | | | | 235 | | | | | 240 |
| Asp | Leu | Pro | Glu | Lys | Gly | Pro | Gly | Pro | Arg | Gln | Tyr | Phe | Leu | Leu | Ser |
| | | | | 245 | | | | | 250 | | | | | 255 | |
| Ser | Gln | Val | Gly | Leu | His | Pro | Glu | Tyr | Arg | Glu | Asp | Leu | Glu | Ala | Leu |
| | | | 260 | | | | | 265 | | | | | 270 | | |
| Gln | Val | Lys | His | Gly | Glu | Ser | Val | Leu | Val | Leu | Asp | Lys | Cys | Thr | Asn |
| | | | 275 | | | | | 280 | | | | | 285 | | |
| Leu | Ser | Glu | Gly | Val | Leu | Ser | Val | Arg | Lys | Arg | Cys | His | Lys | His | Gln |
| | 290 | | | | | 295 | | | | | 300 | | | | |
| Val | Phe | Asp | Tyr | Pro | Gln | Val | Leu | Gln | Glu | Ala | Thr | Phe | Cys | Val | Val |
| 305 | | | | | 310 | | | | | 315 | | | | | 320 |
| Leu | Arg | Gly | Ala | Arg | Leu | Gly | Gln | Ala | Val | Leu | Ser | Asp | Val | Leu | Gln |
| | | | | 325 | | | | | 330 | | | | | 335 | |
| Ala | Gly | Cys | Val | Pro | Val | Val | Ile | Ala | Asp | Ser | Tyr | Ile | Leu | Pro | Phe |
| | | | 340 | | | | | 345 | | | | | 350 | | |
| Ser | Glu | Val | Leu | Asp | Trp | Lys | Arg | Ala | Ser | Val | Val | Pro | Glu | Glu |
| | | | 355 | | | | | 360 | | | | | 365 | | |
| Lys | Met | Ser | Asp | Val | Tyr | Ser | Ile | Leu | Gln | Ser | Ile | Pro | Gln | Arg | Gln |
| | 370 | | | | | 375 | | | | | 380 | | | | |

-continued

```
Ile Glu Glu Met Gln Arg Gln Ala Arg Trp Phe Trp Glu Ala Tyr Phe
385                 390                 395                 400

Gln Ser Ile Lys Ala Ile Ala Leu Ala Thr Leu Gln Ile Ile Asn Asp
            405                 410                 415

Arg Ile Tyr Pro Tyr Ala Ala Ile Ser Tyr Glu Glu Trp Asn Asp Pro
        420                 425                 430

Pro Ala Val Lys Trp Gly Ser Val Ser Asn Pro Leu Phe Leu Pro Leu
    435                 440                 445

Ile Pro Pro Gln Ser Gln Gly Phe Thr Ala Ile Val Leu Thr Tyr Asp
450                 455                 460

Arg Val Glu Ser Leu Phe Arg Val Ile Thr Glu Val Ser Lys Val Pro
465                 470                 475                 480

Ser Leu Ser Lys Leu Leu Val Val Trp Asn Asn Gln Asn Lys Asn Pro
                485                 490                 495

Pro Glu Asp Ser Leu Trp Pro Lys Ile Arg Val Pro Leu Lys Val Val
            500                 505                 510

Arg Thr Ala Glu Asn Lys Leu Ser Asn Arg Phe Phe Pro Tyr Asp Glu
        515                 520                 525

Ile Glu Thr Glu Ala Val Leu Ala Ile Asp Asp Ile Ile Met Leu
    530                 535                 540

Thr Ser Asp Glu Leu Gln Phe Gly Tyr Glu Val Trp Arg Glu Phe Pro
545                 550                 555                 560

Asp Arg Leu Val Gly Tyr Pro Gly Arg Leu His Leu Trp Asp His Glu
                565                 570                 575

Met Asn Lys Trp Lys Tyr Glu Ser Glu Trp Thr Asn Glu Val Ser Met
            580                 585                 590

Val Leu Thr Gly Ala Ala Phe Tyr His Lys Tyr Phe Asn Tyr Leu Tyr
        595                 600                 605

Thr Tyr Lys Met Pro Gly Asp Ile Lys Asn Trp Val Asp Ala His Met
    610                 615                 620

Asn Cys Glu Asp Ile Ala Met Asn Phe Leu Val Ala Asn Val Thr Gly
625                 630                 635                 640

Lys Ala Val Ile Lys Val Thr Pro Arg Lys Phe Lys Cys Pro Glu
                645                 650                 655

Cys Thr Ala Ile Asp Gly Leu Ser Leu Asp Gln Thr His Met Val Glu
            660                 665                 670

Arg Ser Glu Cys Ile Asn Lys Phe Ala Ser Val Phe Gly Thr Met Pro
        675                 680                 685

Leu Lys Val Val Glu His Arg Ala Asp Pro Val Leu Tyr Lys Asp Asp
    690                 695                 700

Phe Pro Glu Lys Leu Lys Ser Phe Pro Asn Ile Gly Ser Leu
705                 710                 715
```

<210> SEQ ID NO 5
<211> LENGTH: 1463
<212> TYPE: PRT
<213> ORGANISM: human

<400> SEQUENCE: 5

```
Met Leu Leu Ser Pro Ser Leu Leu Leu Leu Leu Leu Gly Ala Pro
1               5                   10                  15

Arg Gly Cys Ala Glu Gly Val Ala Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45
```

```
Lys Lys Cys Ile Gln Ala Gly Lys Ser Val Leu Thr Leu Glu Asn Cys
 50                  55                  60

Lys Gln Ala Asn Lys His Met Leu Trp Lys Trp Val Ser Asn His Gly
 65                  70                  75                  80

Leu Phe Asn Ile Gly Gly Ser Gly Cys Leu Gly Leu Asn Phe Ser Ala
                 85                  90                  95

Pro Glu Gln Pro Leu Ser Leu Tyr Glu Cys Asp Ser Thr Leu Val Ser
                100                 105                 110

Leu Arg Trp Arg Cys Asn Arg Lys Met Ile Thr Gly Pro Leu Gln Tyr
                115                 120                 125

Ser Val Gln Val Ala His Asp Asn Thr Val Val Ala Ser Arg Lys Tyr
                130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
                180                 185                 190

Thr Arg Glu Gly Arg Glu Asp Asp Leu Leu Trp Cys Ala Thr Thr Ser
                195                 200                 205

Arg Tyr Glu Arg Asp Glu Lys Trp Gly Phe Cys Pro Asp Pro Thr Ser
210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
                260                 265                 270

Glu Thr Glu Glu Asn Phe Ile Arg Glu His Met Ser Ser Lys Thr Val
                275                 280                 285

Glu Val Trp Met Gly Leu Asn Gln Leu Asp Glu His Ala Gly Trp Gln
                290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

Met Pro Ser Ala Trp Arg Ser Arg Asp Cys Glu Ser Thr Leu Pro Tyr
                340                 345                 350

Ile Cys Lys Lys Tyr Leu Asn His Ile Asp His Glu Ile Val Glu Lys
                355                 360                 365

Asp Ala Trp Lys Tyr Tyr Ala Thr His Cys Glu Pro Gly Trp Asn Pro
370                 375                 380

Tyr Asn Arg Asn Cys Tyr Lys Leu Gln Lys Glu Glu Lys Thr Trp His
385                 390                 395                 400

Glu Ala Leu Arg Ser Cys Gln Ala Asp Asn Ser Ala Leu Ile Asp Ile
                405                 410                 415

Thr Ser Leu Ala Glu Val Glu Phe Leu Val Thr Leu Leu Gly Asp Glu
                420                 425                 430

Asn Ala Ser Glu Thr Trp Ile Gly Leu Ser Ser Asn Lys Ile Pro Val
                435                 440                 445

Ser Phe Glu Trp Ser Asn Asp Ser Ser Val Ile Phe Thr Asn Trp His
                450                 455                 460
```

-continued

```
Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Arg
            485                 490                 495

Leu Phe Tyr Ile Cys Lys Lys Ala Gly His Val Leu Ser Asp Ala Glu
            500                 505                 510

Ser Gly Cys Gln Glu Gly Trp Glu Arg His Gly Gly Phe Cys Tyr Lys
            515                 520                 525

Ile Asp Thr Val Leu Arg Ser Phe Asp Gln Ala Ser Ser Gly Tyr Tyr
    530                 535                 540

Cys Pro Pro Ala Leu Val Thr Ile Thr Asn Arg Phe Glu Gln Ala Phe
545                 550                 555                 560

Ile Thr Ser Leu Ile Ser Ser Val Val Lys Met Lys Asp Ser Tyr Phe
                565                 570                 575

Trp Ile Ala Leu Gln Asp Gln Asn Asp Thr Gly Glu Tyr Thr Trp Lys
                580                 585                 590

Pro Val Gly Gln Lys Pro Glu Pro Val Gln Tyr Thr His Trp Asn Thr
            595                 600                 605

His Gln Pro Arg Tyr Ser Gly Gly Cys Val Ala Met Arg Gly Arg His
    610                 615                 620

Pro Leu Gly Arg Trp Glu Val Lys His Cys Arg His Phe Lys Ala Met
625                 630                 635                 640

Ser Leu Cys Lys Gln Pro Val Glu Asn Gln Glu Lys Ala Glu Tyr Glu
                645                 650                 655

Glu Arg Trp Pro Phe His Pro Cys Tyr Leu Asp Trp Glu Ser Glu Pro
            660                 665                 670

Gly Leu Ala Ser Cys Phe Lys Val Phe His Ser Glu Lys Val Leu Met
        675                 680                 685

Lys Arg Thr Trp Arg Glu Ala Glu Ala Phe Cys Glu Glu Phe Gly Ala
        690                 695                 700

His Leu Ala Ser Phe Ala His Ile Glu Glu Asn Phe Val Asn Glu
705                 710                 715                 720

Leu Leu His Ser Lys Phe Asn Trp Thr Glu Glu Arg Gln Phe Trp Ile
                725                 730                 735

Gly Phe Asn Lys Arg Asn Pro Leu Asn Ala Gly Ser Trp Glu Trp Ser
                740                 745                 750

Asp Arg Thr Pro Val Val Ser Ser Phe Leu Asp Asn Thr Tyr Phe Gly
        755                 760                 765

Glu Asp Ala Arg Asn Cys Ala Val Tyr Lys Ala Asn Lys Thr Leu Leu
        770                 775                 780

Pro Leu His Cys Gly Ser Lys Arg Glu Trp Ile Cys Lys Ile Pro Arg
785                 790                 795                 800

Asp Val Lys Pro Lys Ile Pro Phe Trp Tyr Gln Tyr Asp Val Pro Trp
                805                 810                 815

Leu Phe Tyr Gln Asp Ala Glu Tyr Leu Phe His Thr Phe Ala Ser Glu
                820                 825                 830

Trp Leu Asn Phe Glu Phe Val Cys Ser Trp Leu His Ser Asp Leu Leu
        835                 840                 845

Thr Ile His Ser Ala His Glu Gln Phe Ile His Ser Lys Ile Lys
        850                 855                 860

Ala Leu Ser Lys Tyr Gly Ala Ser Trp Trp Ile Gly Leu Gln Glu Glu
865                 870                 875                 880

Arg Ala Asn Asp Glu Phe Arg Trp Arg Asp Gly Thr Pro Val Ile Tyr
```

-continued

```
                885                 890                 895
Gln Asn Trp Asp Thr Gly Arg Glu Arg Thr Val Asn Asn Ser Gln
                900                 905                 910
Arg Cys Gly Phe Ile Ser Ser Ile Thr Gly Leu Trp Gly Ser Glu
                915                 920                 925
Cys Ser Val Ser Met Pro Ser Ile Cys Lys Arg Lys Val Trp Leu
                930                 935                 940
Ile Glu Lys Lys Lys Asp Thr Pro Lys Gln His Gly Thr Cys Pro Lys
945                 950                 955                 960
Gly Trp Leu Tyr Phe Asn Tyr Lys Cys Leu Leu Leu Asn Ile Pro Lys
                965                 970                 975
Asp Pro Ser Ser Trp Lys Asn Trp Thr His Ala Gln His Phe Cys Ala
                980                 985                 990
Glu Glu Gly Gly Thr Leu Val Ala Ile Glu Ser Glu Val Glu Gln Ala
                995                 1000                1005
Phe Ile Thr Met Asn Leu Phe Gly Gln Thr Thr Ser Val Trp Ile
1010                1015                1020
Gly Leu Gln Asn Asp Asp Tyr Glu Thr Trp Leu Asn Gly Lys Pro
1025                1030                1035
Val Val Tyr Ser Asn Trp Ser Pro Phe Asp Ile Ile Asn Ile Pro
1040                1045                1050
Ser His Asn Thr Thr Glu Val Gln Lys His Ile Pro Leu Cys Ala
1055                1060                1065
Leu Leu Ser Ser Asn Pro Asn Phe His Phe Thr Gly Lys Trp Tyr
1070                1075                1080
Phe Glu Asp Cys Gly Lys Glu Gly Tyr Gly Phe Val Cys Glu Lys
1085                1090                1095
Met Gln Asp Thr Ser Gly His Gly Val Asn Thr Ser Asp Met Tyr
1100                1105                1110
Pro Met Pro Asn Thr Leu Glu Tyr Gly Asn Arg Thr Tyr Lys Ile
1115                1120                1125
Ile Asn Ala Asn Met Thr Trp Tyr Ala Ala Ile Lys Thr Cys Leu
1130                1135                1140
Met His Lys Ala Gln Leu Val Ser Ile Thr Asp Gln Tyr His Gln
1145                1150                1155
Ser Phe Leu Thr Val Val Leu Asn Arg Leu Gly Tyr Ala His Trp
1160                1165                1170
Ile Gly Leu Phe Thr Thr Asp Asn Gly Leu Asn Phe Asp Trp Ser
1175                1180                1185
Asp Gly Thr Lys Ser Ser Phe Thr Phe Trp Lys Asp Glu Glu Ser
1190                1195                1200
Ser Leu Leu Gly Asp Cys Val Phe Ala Asp Ser Asn Gly Arg Trp
1205                1210                1215
His Ser Thr Ala Cys Glu Ser Phe Leu Gln Gly Ala Ile Cys His
1220                1225                1230
Val Pro Pro Glu Thr Arg Gln Ser Glu His Pro Glu Leu Cys Ser
1235                1240                1245
Glu Thr Ser Ile Pro Trp Ile Lys Phe Lys Ser Asn Cys Tyr Ser
1250                1255                1260
Phe Ser Thr Val Leu Asp Ser Met Ser Phe Glu Ala Ala His Glu
1265                1270                1275
Phe Cys Lys Lys Glu Gly Ser Asn Leu Leu Thr Ile Lys Asp Glu
1280                1285                1290
```

```
Ala Glu Asn Ala Phe Leu Leu Glu Glu Leu Phe Ala Phe Gly Ser
    1295            1300                1305

Ser Val Gln Met Val Trp Leu Asn Ala Gln Phe Asp Gly Asn Asn
    1310            1315                1320

Glu Thr Ile Lys Trp Phe Asp Gly Thr Pro Thr Asp Gln Ser Asn
    1325            1330                1335

Trp Gly Ile Arg Lys Pro Asp Thr Asp Tyr Phe Lys Pro His His
    1340            1345                1350

Cys Val Ala Leu Arg Ile Pro Glu Gly Leu Trp Gln Leu Ser Pro
    1355            1360                1365

Cys Gln Glu Lys Lys Gly Phe Ile Cys Lys Met Glu Ala Asp Ile
    1370            1375                1380

His Thr Ala Glu Ala Leu Pro Glu Lys Gly Pro Ser His Ser Ile
    1385            1390                1395

Ile Pro Leu Ala Val Val Leu Thr Leu Ile Val Ile Val Ala Ile
    1400            1405                1410

Cys Thr Leu Ser Phe Cys Ile Tyr Lys His Asn Gly Gly Phe Phe
    1415            1420                1425

Arg Arg Leu Ala Gly Phe Arg Asn Pro Tyr Tyr Pro Ala Thr Asn
    1430            1435                1440

Phe Ser Thr Val Tyr Leu Glu Glu Asn Ile Leu Ile Ser Asp Leu
    1445            1450                1455

Glu Lys Ser Asp Gln
    1460
```

METHODS AND MATERIALS FOR IDENTIFYING AND TREATING MEMBRANOUS NEPHROPATHY

CROSS-REFERENCE TO RELATED APPLICATIONS

This application is a National Stage application under 35 U.S.C. § 371 of International Application No. PCT/US2019/046676, having an International Filing Date of Aug. 15, 2019, which claims priority to U.S. Application Ser. No. 62/764,681, filed on Aug. 15, 2018. The disclosure of the prior application is considered part of the disclosure of this application, and is incorporated in its entirety 10 into this application.

SEQUENCE LISTING

This application contains a Sequence Listing that has been submitted electronically as an ASCII text file named "07039-1218US1_subSL.txt." The ASCII text file, created on Sep. 13, 2024, is 34,388 bytes in size. The material in the ASCII text file is hereby incorporated by reference in its entirety.

BACKGROUND

1. Technical Field

This document relates to methods and materials involved in identifying and/or treating mammals having membranous nephropathy (e.g., membranous nephropathy with an elevated level of an exostosin 1 (EXT1) and/or exostosin 2 (EXT2) polypeptide in the glomerular basement membrane (GBM)). For example, this document provides methods and materials for administering one or more immunosuppressive agents (e.g., corticosteroids, cyclosporine, or a B-cell reduction or depletion agent such as Rituximab) to treat a mammal (e.g., a human) having membranous nephropathy.

2. Background Information

Membranous nephropathy is the most common cause of nephrotic syndrome in Caucasian adults. It is classified into primary and secondary membranous nephropathy. Primary membranous nephropathy accounts for 70-75% cases and secondary for 25-30% cases. Membranous nephropathy results from an autoimmune response to accumulation of a target antigen in the GBM. The GBM is the integral part of the glomerular capillaries forming the filtering unit of the kidney. It is reported that in about 70 percent of primary cases, membranous nephropathy results from accumulation of phospholipase A2 receptor (PLA2R) target antigens in the GBM and subsequent formation of antigen-antibody complexes (Beck et al., *N. Engl. J. Med.*, 361:11-21 (2009)). Thrombospondin type-1 domain-containing 7A (THS7DA) is reported to be another antigen that accounts for about 5% of the cases of primary membranous nephropathy (Tomas et al., *N. Engl. J. Med.*, 24:2277-2287 (2014)). Secondary membranous nephropathy is often associated with autoimmune diseases such as lupus, mixed connective tissue disorder, and Sjogren's syndrome. The target antigen in the remaining 25% primary membranous nephropathy and all of secondary membranous nephropathy is unknown.

SUMMARY

This document provides methods and materials involved in identifying and treating mammals (e.g., humans) having membranous nephropathy (e.g., membranous nephropathy with an elevated level of an EXT1 and/or EXT2 polypeptide in the GBM). For example, this document provides methods and materials for identifying a mammal (e.g., a human) having membranous nephropathy having an elevated level of an EXT1 polypeptide and/or an elevated level of an EXT2 polypeptide in the GBM that can serve as a target antigen in membranous nephropathy. This document also provides methods and materials for identifying a mammal (e.g., a human) having membranous nephropathy that includes the presence of autoantibodies having binding specificity for an EXT1 polypeptide and/or an EXT2 polypeptide. As described herein, mammals (e.g., humans) having membranous nephropathy can be identified as having an elevated level of an EXT1 and/or an EXT2 polypeptide in the GBM. In such cases, the mammal can be classified as having membranous nephropathy that includes an elevated level of an EXT1 and/or an EXT2 polypeptide in the GBM. As also described herein, mammals (e.g., humans) having membranous nephropathy can be identified as having autoantibodies having binding specificity for an EXT1 polypeptide and/or an EXT2 polypeptide. In such cases, the mammal can be classified as having membranous nephropathy that includes the presence of autoantibodies having binding specificity for an EXT1 polypeptide and/or an EXT2 polypeptide. Identifying mammals (e.g., humans) as having membranous nephropathy that includes an elevated level of an EXT1 and/or an EXT2 polypeptide in the GBM and/or that includes the presence of autoantibodies having binding specificity for an EXT1 polypeptide and/or an EXT2 polypeptide can allow clinicians and patients to proceed with appropriate membranous nephropathy treatment options.

This document also provides methods and materials for treating membranous nephropathy. For example, a mammal (e.g., a human) having membranous nephropathy that was identified as having an elevated level of an EXT1 and/or an EXT2 polypeptide in the GBM, as having autoantibodies having binding specificity for an EXT1 polypeptide and/or an EXT2 polypeptide, or as having both an elevated level of an EXT1 and/or an EXT2 polypeptide in the GBM and autoantibodies having binding specificity for an EXT1 polypeptide and/or an EXT2 polypeptide can be administered one or more immunosuppressive agents (e.g., corticosteroids, cyclosporine, or a B-cell reduction or depletion agent such as Rituximab) to reduce inflammation and/or B-cell autoantibody production. As described herein, mammals (e.g., humans) having membranous nephropathy and identified as having an elevated level of an EXT1 and/or an EXT2 polypeptide in the GBM and/or as having autoantibodies having binding specificity for an EXT1 polypeptide and/or an EXT2 polypeptide have a form of membranous nephropathy that is caused by the presence of antigen-autoantibody complexes where the antigen is an EXT1 and/or EXT2 polypeptide. In such cases, the mammal (e.g., human) can be effectively treated using one or more immunosuppressive agents (e.g., corticosteroids, cyclosporine, or a B-cell reduction or depletion agent such as Rituximab) to reduce inflammation and/or B-cell autoantibody production. Having the ability to administer one or more immunosuppressive agents to mammals (e.g., humans) (a) having membranous nephropathy and (b) identified as having an elevated level of an EXT1 and/or an EXT2 polypeptide in the GBM and/or as having autoantibodies having binding specificity for an EXT1 polypeptide and/or an EXT2 polypeptide can allow clinicians and patients to treat membranous nephropathy effectively.

As also described herein, most, if not all, membranous nephropathy cases in humans are caused by autoantibodies having specificity to a polypeptide that accumulates in the GBM. Those polypeptides include EXT1, EXT2, PLA2R, and THS7DA. In general, the use of immunosuppressive agents such as B-cell reduction or depletion agents (e.g., Rituximab) in cases such as membranous nephropathy currently requires an identification of autoantibodies (e.g., anti-PLA2R autoantibodies or anti-THS7DA autoantibodies) before a powerful B-cell reduction or depletion agent such as Rituximab is administered to a human to treat membranous nephropathy. Based, at least in part, on the results presented herein, however, such an identification is no longer needed prior to using an immunosuppressive agent to treat membranous nephropathy. For example, a mammal (e.g., a human) having membranous nephropathy (e.g., membranous nephropathy with an elevated level of an EXT1, an EXT2, a PLA2R, and/or a THS7DA polypeptide) can be administered one or more immunosuppressive agents (e.g., corticosteroids, cyclosporine, or a B-cell reduction or depletion agent such as Rituximab) to treat membranous nephropathy without having been tested for an elevated level of any polypeptide in the GBM and without having been tested for the presence of any autoantibody. In some cases, a mammal (e.g., a human) having membranous nephropathy can be administered one or more immunosuppressive agents (e.g., corticosteroids, cyclosporine, or a B-cell reduction or depletion agent such as Rituximab) to treat membranous nephropathy without having been tested for an elevated level of (a) an EXT1 polypeptide, (b) an EXT2 polypeptide, (c) a PLA2R polypeptide, and (d) a THS7DA polypeptide and without having been tested for the presence of (a) an autoantibody having specificity for an EXT1 polypeptide, (b) an autoantibody having specificity for an EXT2 polypeptide. (c) an autoantibody having specificity for a PLA2R polypeptide, and (d) an autoantibody having specificity for a THS7DA polypeptide. Having the ability to treat membranous nephropathy without prior testing for elevated levels of particular polypeptides in the GBM and without prior testing for the presence of particular autoantibodies can allow clinicians and patients to treat membranous nephropathy safely without the added testing delay or expense.

In some cases, identification of the target antigen and autoantibodies can be involved in the diagnosis and/or management of a mammal (e.g., a human) with membranous nephropathy. For example, a mammal (e.g., a human) having membranous nephropathy (e.g., membranous nephropathy with GBM accumulation of an EXT1, EXT2, PLA2R, and/or THS7DA polypeptide and the presence of autoantibodies to one or more target antigens) can be administered one or more immunosuppressive agents (e.g., corticosteroids, cyclosporine, or a B-cell reduction or depletion agent such as Rituximab) to treat membranous nephropathy. In some cases, the response to the immunosuppressive treatment can be monitored for a decrease or complete elimination of the autoantibodies to one or more of a PLA2R, THS7DA, EXT1, or EXT2 polypeptide. In some cases, the response to treatment can be monitored by examining a kidney biopsy for a decrease or elimination of one or more target antigens (e.g., a PLA2R, THS7DA, EXT1, or EXT2 polypeptide). In some cases, a mammal (e.g., a human) having membranous nephropathy can be administered one or more immunosuppressive agents (e.g., corticosteroids, cyclosporine, or a B-cell reduction or depletion agent such as Rituximab) to treat membranous nephropathy based on the presence of an autoantibody to one or more of a PLA2R, THS7DA, EXT1, or EXT2 polypeptide in the absence of evaluating a kidney biopsy for an elevated level of a PLA2R, THS7DA, EXT1, or EXT2 polypeptide. Although kidney biopsies showing an accumulation of PLA2R, THS7DA, EXT1, and/or EXT2 polypeptides in GBM may be considered a gold standard for diagnosis of membranous nephropathy, the presence of autoantibodies to a PLA2R, THS7DA, EXT1, or EXT2 polypeptide can be used to identify specific types of membranous nephropathy (e.g., membranous nephropathy associated with accumulation of PLA2R, THS7DA, EXT1, or EXT2 polypeptides) without the need for a kidney biopsy.

In general, one aspect of this document features a method for identifying a mammal as having membranous nephropathy comprising an elevated level of a polypeptide within kidney tissue of the mammal, wherein the polypeptide is an exostosin 1 (EXT1) polypeptide or an exostosin 2 (EXT2) polypeptide. The method comprises (or consists essentially of or consists of) (a) determining the presence or absence of autoantibodies within the mammal, wherein the autoantibodies are specific for the polypeptide, (b) classifying the mammal as having the membranous nephropathy if the autoantibodies are present within the mammal, and (c) classifying the mammal as not having the membranous nephropathy if the autoantibodies are absent within the mammal. The mammal can be a human. The polypeptide can be the EXT1 polypeptide. The polypeptide can be the EXT2 polypeptide. The membranous nephropathy can lack an elevated level of a PLA2R polypeptide within the kidney tissue. The membranous nephropathy can lack an elevated level of a THS7DA polypeptide within the kidney tissue. The method can comprise detecting the presence of the autoantibodies and classifying the mammal as having the membranous nephropathy. The method can comprise detecting the absence of the autoantibodies and classifying the mammal as not having the membranous nephropathy.

In another aspect, this document features a method for identifying a mammal as having kidney tissue comprising an elevated level of a polypeptide, wherein the polypeptide is an exostosin 1 (EXT1) polypeptide or an exostosin 2 (EXT2) polypeptide. The method comprises (or consists essentially of or consists of) (a) determining the presence or absence of the kidney tissue within a sample obtained from the mammal, (b) classifying the mammal as having the kidney tissue if the presence is determined, and (c) classifying the mammal as not having the kidney tissue if the absence is determined. The mammal can be a human. The polypeptide can be the EXT1 polypeptide. The polypeptide can be the EXT2 polypeptide. The kidney tissue can lack an elevated level of a PLA2R polypeptide. The kidney tissue can lack an elevated level of a THS7DA polypeptide. The method can comprise detecting the presence and classifying the mammal as having the kidney tissue. The method can comprise detecting the absence and classifying the mammal as not having the kidney tissue.

In another aspect, this document features a method for identifying a mammal having membranous nephropathy as having autoantibodies specific for a polypeptide, wherein the polypeptide is an exostosin 1 (EXT1) polypeptide or an exostosin 2 (EXT2) polypeptide. The method comprises (or consists essentially of or consists of) (a) determining the presence or absence of the autoantibodies within the mammal, (b) classifying the mammal as having the autoantibodies if the autoantibodies are present within the mammal, and (c) classifying the mammal as not having the autoantibodies if the autoantibodies are absent within the mammal. The mammal can be a human. The polypeptide can be the EXT1 polypeptide. The polypeptide can be the EXT2 polypeptide.

Kidney tissue of the mammal can lack an elevated level of a PLA2R polypeptide. Kidney tissue of the mammal can lack an elevated level of a THS7DA polypeptide. The method can comprise detecting the presence and classifying the mammal as having the autoantibodies. The method can comprise detecting the absence and classifying the mammal as not having the autoantibodies.

In another aspect, this document features a method for treating a mammal having membranous nephropathy. The method comprises (or consists essentially of or consists of) (a) identifying a mammal as having (i) autoantibodies specific for a polypeptide or (ii) kidney tissue comprising an elevated level of the polypeptide, wherein the polypeptide is an exostosin 1 (EXT1) polypeptide or an exostosin 2 (EXT2) polypeptide, and (b) administering an immunosuppressant to the mammal. The mammal can be a human. The mammal can be identified as having the autoantibodies. The mammal can be identified as having the kidney tissue. The polypeptide can be the EXT1 polypeptide. The polypeptide can be the EXT2 polypeptide. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The level of autoantibodies present within the mammal can be reduced by at least 50 percent following the administering step.

In another aspect, this document features a method for treating a mammal having membranous nephropathy. The method comprises (or consists essentially of or consists of) administering an immunosuppressant to a mammal identified as having (i) autoantibodies specific for a polypeptide or (ii) kidney tissue comprising an elevated level of the polypeptide, wherein the polypeptide is an exostosin 1 (EXT1) polypeptide or an exostosin 2 (EXT2) polypeptide. The mammal can be a human. The mammal can be a mammal that was identified as having the autoantibodies. The mammal can be a mammal that was identified as having the kidney tissue. The polypeptide can be the EXT1 polypeptide. The polypeptide can be the EXT2 polypeptide. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The level of autoantibodies present within the mammal can be reduced by at least 50 percent following the administering step.

In another aspect, this document features a method for treating a mammal having membranous nephropathy and kidney tissue comprising an elevated level of a polypeptide, wherein the polypeptide is an exostosin 1 (EXT1) polypeptide or an exostosin 2 (EXT2) polypeptide. The method comprises (or consists essentially of or consists of) administering an immunosuppressant to the mammal. The mammal can be a human. The mammal can comprise autoantibodies specific for the polypeptide. The mammal can be a mammal was identified as having the kidney tissue. The polypeptide can be the EXT1 polypeptide. The polypeptide can be the EXT2 polypeptide. The kidney tissue can lack an elevated level of a PLA2R polypeptide. The kidney tissue can lack an elevated level of a THS7DA polypeptide. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The level of autoantibodies present within the mammal can be reduced by at least 50 percent following the administering step.

In another aspect, this document features a method for treating membranous nephropathy. The method comprises (or consists essentially of or consists of) administering an immunosuppressant to the mammal without detecting the presence, within the mammal, of autoantibodies specific for any polypeptide of a group of polypeptides and without detecting the presence of kidney tissue of the mammal comprising an elevated level of any polypeptide of the group, wherein the group consists of an EXT1 polypeptide, an EXT2 polypeptide, a PLA2R polypeptide, and a THS7DA polypeptide. The mammal can be a human. The mammal can comprise autoantibodies specific for the EXT1 polypeptide. The mammal can comprise autoantibodies specific for the EXT2 polypeptide. The mammal can comprise autoantibodies specific for the PLA2R polypeptide. The mammal can comprise autoantibodies specific for the THS7DA polypeptide. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The level of autoantibodies present within the mammal can be reduced by at least 50 percent following the administering step.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a sequence listing of a nucleic acid sequence (SEQ ID NO: 1) encoding a human EXT1 polypeptide and an amino acid sequence (SEQ ID NO:2) of a human EXT1 polypeptide.

FIG. 2 is a sequence listing of a nucleic acid sequence (SEQ ID NO:3) encoding a human EXT2 polypeptide and an amino acid sequence (SEQ ID NO:4) of a human EXT2 polypeptide.

FIG. 6. EXT1 and EXT2 staining by immunofluorescence microscopy of a case of MN that was initially weakly positive for EXT1/EXT2 and subsequently turned strongly positive at the time of development of clinical lupus. The inserts show the EXT1 and EXT2 deposits by confocal microscopy. The year of the biopsy and the clinical and histologic diagnoses are indicated above each picture.

FIG. 14. Representative mass spectrometry findings of control cases. Low spectral counts of PLA2R and no detectable spectral counts of EXT1 or EXT2 are present in the control cases. The last two columns are from two cases of PLA2R-negative membranous nephropathy that were also negative for EXT1 and EXT2. Proteins inherent to the GBM such as laminin, nestin, and nidogen also are shown.

DETAILED DESCRIPTION

Figure 3:
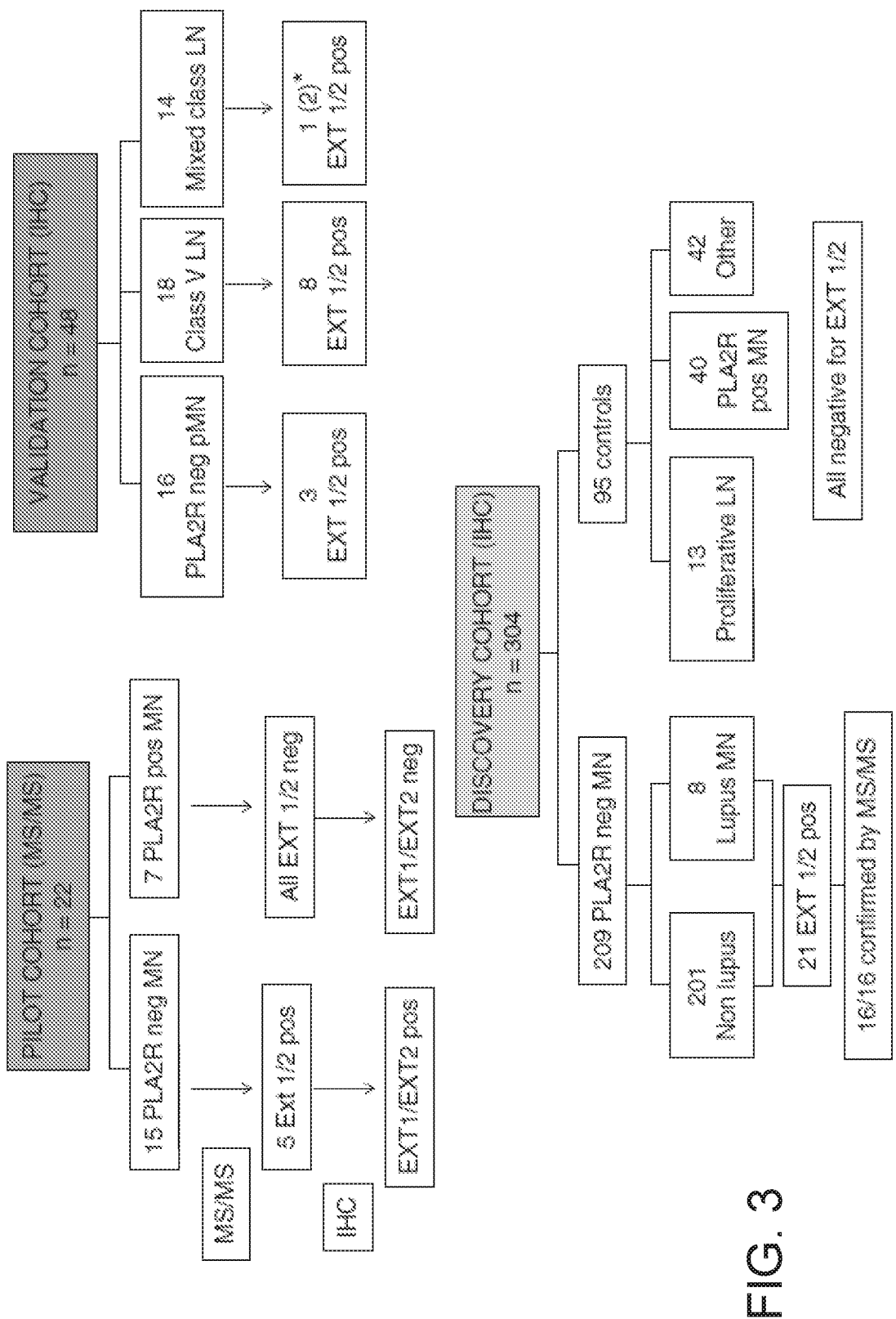
FIG. 3. Flowchart of the pilot, discovery, and validation cohorts. Initial pilot studies were done by mass spectrometry studies using 15 PLA2Rnegative MN and seven PLA2R-positive MN cases. After detection of EXT1/EXT2 in five cases confirmed by IHC, a large number (n=209) of PLA2R-negative MN cases and controls (n=95) were studied for expression of EXT1/EXT2 by IHC. Controls included 13 cases of proliferative lupus nephritis (LN) without a membranous component and 40 cases of PLA2R-positive MN. In addition, 48 cases of MN in a validation cohort that included PLA2R-negative primary MN (pMN), membranous (class 5) LN, and mixed class LN with a membranous component were studied. *One case (patient #16) started with pure MN with signs of autoimmunity and then shifted to mixed class. Neg, negative: pos, positive.

This document provides methods and materials for identifying and/or treating mammals (e.g., humans) having membranous nephropathy (e.g., membranous nephropathy with an elevated level of an EXT1 and/or EXT2 polypeptide in the GBM). For example, this document provides methods and materials for identifying a mammal (e.g., a human) having membranous nephropathy as having (a) autoantibodies specific for an EXT1 polypeptide and/or an EXT2 polypeptide and/or (b) a GBM having an elevated level of an EXT1 polypeptide and/or an elevated level of an EXT2 polypeptide.

Any appropriate mammal having membranous nephropathy can be identified as having (a) autoantibodies specific for an EXT1 polypeptide and/or an EXT2 polypeptide and/or (b) kidney tissue (e.g., GBM) having an elevated level of an EXT1 polypeptide and/or an elevated level of an EXT2 polypeptide. For example, humans and other primates such as monkeys having membranous nephropathy can be identified as having (a) autoantibodies specific for an EXT1 polypeptide and/or an EXT2 polypeptide and/or (b) kidney tissue such as GBM having an elevated level of an EXT1 polypeptide and/or an elevated level of an EXT2 polypeptide. In some cases, dogs, cats, horses, cows, pigs, sheep, mice, or rats having membranous nephropathy can be identified as having (a) autoantibodies specific for an EXT1 polypeptide and/or an EXT2 polypeptide and/or (b) kidney tissue such as GBM having an elevated level of an EXT1 polypeptide and/or an elevated level of an EXT2 polypeptide as described herein.

Any appropriate method can be used to determine if a mammal (e.g., a human) has autoantibodies specific for an EXT1 polypeptide and/or an EXT2 polypeptide. For example, immunological assays using an EXT1 polypeptide (or a fragment thereof capable of binding to an anti-EXT1 antibody) can be used to determine if a sample contains autoantibodies specific for an EXT1 polypeptide, and immunological assays using an EXT2 polypeptide (or a fragment thereof capable of binding to an anti-EXT2 antibody) can be used to determine if a sample contains autoantibodies specific for an EXT2 polypeptide. In some cases, an immobilized EXT1 (or EXT2 polypeptide) or an immobilized fragment thereof can be used to capture an anti-EXT1 autoantibody (or anti-EXT2 autoantibody) if present within a sample being tested, and an anti-Ig antibody (e.g., an anti-human IgG antibody when testing for human autoantibodies) can be used to determine whether or not autoantibodies were captured. In some cases, an anti-Ig antibody can be labeled (e.g., fluorescently or enzymatically labeled) to aid in detection. Any appropriate sample can be used to determine if a mammal (e.g., a human) has autoantibodies specific for an EXT1 polypeptide and/or an EXT2 polypeptide. For example, blood sample, serum samples, or urine samples obtained from a mammal being tested can be used to determine if a mammal (e.g., a human) has autoantibodies specific for an EXT1 polypeptide and/or an EXT2 polypeptide.

Any appropriate method can be used to determine if a mammal (e.g., a human) has kidney tissue (e.g., GBM) having an elevated level of an EXT1 polypeptide and/or an EXT2 polypeptide. For example, immunological techniques such as immunohistochemistry (IHC) techniques, immunofluorescence (IF) techniques, or Western blot techniques can be used to determine if a mammal (e.g., a human) has kidney tissue (e.g., GBM) having an elevated level of an EXT1 polypeptide and/or an EXT2 polypeptide. In some cases, a kidney tissue sample obtained from a mammal to be tested can be stained using an anti-EXT1 antibody to determine if the mammal has kidney tissue (e.g., GBM) having an elevated level of EXT1 polypeptides. In some cases, a kidney tissue sample obtained from a mammal to be tested can be stained using an anti-EXT2 antibody to determine if the mammal has kidney tissue (e.g., GBM) having an elevated level of EXT2 polypeptides. Any appropriate sample can be used to determine if a mammal (e.g., a human) has kidney tissue (e.g., GBM) having an elevated level of an EXT1 polypeptide and/or an EXT2 polypeptide. For example, kidney tissue biopsies can be obtained from a mammal (e.g., a human) being tested and used to determine if a mammal (e.g., a human) has kidney tissue (e.g., GBM) having an elevated level of an EXT1 polypeptide and/or an EXT2 polypeptide.

The term "elevated level" as used herein with respect to an EXT1 polypeptide level refers to a level of EXT1 polypeptide present within kidney tissue (e.g., GBM) that is greater (e.g., at least 10, 25, 35, 45, 50, 55, 65, 75, 80, 90, or 100 percent greater) than the median level of EXT1 polypeptides present within normal kidney tissue (e.g., a normal GBM) of comparable mammals not having membranous nephropathy.

The term "elevated level" as used herein with respect to an EXT2 polypeptide level refers to a level of EXT2 polypeptide present within kidney tissue (e.g., GBM) that is greater (e.g., at least 10, 25, 35, 45, 50, 55, 65, 75, 80, 90, or 100 percent greater) than the median level of EXT2 polypeptides present within normal kidney tissue (e.g., a normal GBM) of comparable mammals not having membranous nephropathy.

A human EXT1 polypeptide can have the amino acid sequence set forth in FIG. 1. A human EXT2 polypeptide can have the amino acid sequence set forth in FIG. 2.

Once a mammal (e.g., a human) having membranous nephropathy is identified as having autoantibodies specific for an EXT1 polypeptide and/or an EXT2 polypeptide as described herein, the mammal can be classified as having membranous nephropathy that includes the presence of those autoantibodies (e.g., membranous nephropathy that includes the presence of anti-EXT1 autoantibodies or membranous nephropathy that includes the presence of anti-EXT2 autoantibodies). In some cases, a mammal (e.g., a human) having membranous nephropathy that is identified as having autoantibodies specific for an EXT1 polypeptide as described herein can be classified as having membranous nephropathy that includes kidney tissue having an elevated level of EXT1 polypeptides. In some cases, a mammal (e.g., a human) having membranous nephropathy that is identified as having autoantibodies specific for an EXT2 polypeptide as described herein can be classified as having membranous nephropathy that includes kidney tissue having an elevated level of EXT2 polypeptides.

Once a mammal (e.g., a human) having membranous nephropathy is identified as having kidney tissue (e.g., GBM) having an elevated level of an EXT1 polypeptide and/or an EXT2 polypeptide as described herein, the mammal can be classified as having membranous nephropathy that includes the presence of that kidney tissue (e.g., membranous nephropathy that includes the presence of kidney tissue such as GBM having an elevated level of EXT1 polypeptides or membranous nephropathy that includes the presence of kidney tissue such as GBM having an elevated level of EXT2 polypeptides). In some cases, a mammal (e.g., a human) having membranous nephropathy that is identified as having kidney tissue (e.g., GBM) having an elevated level of an EXT1 polypeptide as described herein can be classified as having membranous nephropathy that includes autoantibodies specific for an EXT1 polypeptide. In some cases, a mammal (e.g., a human) having membranous nephropathy that is identified as having kidney tissue (e.g., GBM) having an elevated level of an EXT2 polypeptide as described herein can be classified as having membranous nephropathy that includes autoantibodies specific for an EXT2 polypeptide.

As described herein, this document also provides methods and materials for treating a mammal having membranous nephropathy. For example, a mammal (e.g., a human) having membranous nephropathy that is identified as having (a) autoantibodies specific for an EXT1 polypeptide and/or an EXT2 polypeptide and/or (b) kidney tissue (e.g., GBM) having an elevated level of an EXT1 polypeptide and/or an elevated level of an EXT2 polypeptide as described herein can be treated with one or more immunosuppressants. In some cases, a mammal (e.g., a human) having membranous nephropathy that is identified as having (a) autoantibodies specific for an EXT1 polypeptide and/or an EXT2 polypeptide and/or (b) kidney tissue (e.g., GBM) having an elevated level of an EXT1 polypeptide and/or an elevated level of an EXT2 polypeptide as described herein can be administered, or instructed to self-administer, one or more immunosuppressants to treat membranous nephropathy.

In some cases, a mammal (e.g., a human) having membranous nephropathy can be administered one or more immunosuppressants (e.g., anti-CD20 antibodies such as rituximab) to treat membranous nephropathy without attempting to determine if the mammal has autoantibodies specific for the following four polypeptides: an EXT1 polypeptide, an EXT2 polypeptide, a PLA2R polypeptide, and a THS7DA polypeptide. In some cases, a mammal (e.g., a human) having membranous nephropathy can be administered one or more immunosuppressants (e.g., anti-CD20 antibodies such as rituximab) to treat membranous nephropathy without attempting to determine if the mammal has kidney tissue (e.g., GBM) having an elevated level of any of the following four polypeptides: an EXT1 polypeptide, an EXT2 polypeptide, a PLA2R polypeptide, and a THS7DA polypeptide. In some cases, a mammal (e.g., a human) having membranous nephropathy can be administered one or more immunosuppressants (e.g., anti-CD20 antibodies such as rituximab) to treat membranous nephropathy without attempting to determine if the mammal has autoantibodies specific for those four polypeptides and without attempting to determine if the mammal has kidney tissue (e.g., GBM) having an elevated level of any of those four polypeptides. In some cases, a mammal (e.g., a human) having membranous nephropathy that is administered one or more immunosuppressants (e.g., anti-CD20 antibodies such as rituximab) to treat membranous nephropathy without attempting to determine the presence of such autoantibodies and such kidney tissue (e.g., GBM) can have autoantibodies specific for an EXT1 polypeptide, can have autoantibodies specific for an EXT2 polypeptide, can have autoantibodies specific for a PLA2R polypeptide, or can have autoantibodies specific for a THS7DA polypeptide.

Any appropriate immunosuppressant can be administered to a mammal (e.g., a mammal that was identified as having (a) autoantibodies specific for an EXT1 polypeptide and/or an EXT2 polypeptide and/or (b) kidney tissue (e.g., GBM) having an elevated level of an EXT1 polypeptide and/or an elevated level of an EXT2 polypeptide as described herein) to treat membranous nephropathy. In some cases, an immunosuppressant used as described herein to treat membranous nephropathy can reduce inflammation and/or reduce B-cell autoantibody production within a mammal. Examples of immunosuppressants that can be used as described herein to treat membranous nephropathy include, without limitation, mycophenolate mofetil (e.g., Cellcept): steroids such as prednisone: B-cell inhibitors such as anti-CD20 antibodies (e.g., rituximab): calcineurin inhibitors such as cyclosporine and tacrolimus; and alkylating agents/chemotherapeutic drugs such as cyclophosphamide.

In some cases, two or more (e.g., two, three, four, five, six, or more) immunosuppressants can be administered to a mammal having membranous nephropathy (e.g., a human having membranous nephropathy and autoantibodies specific for an EXT1 polypeptide and/or an EXT2 polypeptide). For example, two immunosuppressants (e.g., prednisone and Cellcept) can be administered to a human having membranous nephropathy.

In some cases, one or more immunosuppressants can be administered to a mammal once or multiple times over a period of time ranging from days to months. In some cases, one or more immunosuppressive drugs can be given to achieve remission of membranous nephropathy, and then given during follow up periods to prevent relapse of the membranous nephropathy. In some cases, one or more immunosuppressants can be formulated into a pharmaceutically acceptable composition for administration to a mammal (e.g., a human) having membranous nephropathy to reduce inflammation and/or to reduce B-cell autoantibody production within that mammal. For example, a therapeutically effective amount of an immunosuppressant can be formulated together with one or more pharmaceutically acceptable carriers (additives) and/or diluents. A pharmaceutical composition can be formulated for administration in solid or liquid form including, without limitation, in the form of sterile solutions, suspensions, sustained-release formulations, tablets, capsules, pills, powders, or granules.

Pharmaceutically acceptable carriers, fillers, and vehicles that can be used in a pharmaceutical composition described herein can include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more immunosuppressants can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration can include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and can be stored in a freeze dried (lyophilized) condition requiring the addition of the sterile liquid carrier, for example, water for injections, immediately prior to use. Extemporaneous injection solutions and suspensions can be prepared from sterile powders, granules, and tablets.

In some cases, a pharmaceutically acceptable composition including one or more immunosuppressants can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the nephropathy, the route of administration, the age and general health condition of the subject, excipient usage, the possibility of co-usage with other therapeutic treatments, and the judgment of the treating physician.

An effective amount of a composition containing one or more immunosuppressants can be any amount that reduces inflammation or B-cell autoantibody production (e.g., B-cell antibody production inhibition or reduction in the number of B-cells) within a mammal having membranous nephropathy without producing significant toxicity to the mammal. For example, an effective amount of rituximab to treat membranous nephropathy as described herein can be from about 500 mg to about 1.5 g (e.g., from about 500 mg to about 1.25 g, from about 500 mg to about 1.0 g, from about 500 mg to about 750 mg, from about 750 mg to about 1.5 g, from about 1 g to about 1.5 g, or from about 1.25 g to about 1.5 g) administered IV about two weeks apart. In some cases, an effective amount of rituximab to treat membranous nephropathy as described herein can be from about 200 mg/m$^2$ to about 500 mg/m$^2$ (e.g., from about 200 mg/m$^2$ to about 450 mg/m$^2$, from about 200 mg/m$^2$ to about 400 mg/m$^2$, from about 200 mg/m$^2$ to about 375 mg/m$^2$, from about 250 mg/m$^2$ to about 500 mg/m$^2$, from about 300 mg/m$^2$ to about 500 mg/m$^2$, from about 350 mg/m$^2$ to about 500 mg/m$^2$, or from about 350 mg/m$^2$ to about 400 mg/m$^2$) administered weekly for about four weeks. If a particular mammal fails to respond to a particular amount, then the amount of an immunosuppressant can be increased by, for example, two fold. After receiving this higher amount, the mammal can be monitored for both responsiveness to the treatment and toxicity symptoms, and adjustments made accordingly. For example, levels of anti-EXT1 and/or EXT2 autoantibodies present within the mammal (e.g., within the blood of the mammal) can be monitored by an appropriate method (e.g., ELISA). In some cases, the effective amount of a composition containing one or more immunosuppressants can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition can require an increase or decrease in the actual effective amount administered.

The frequency of administration of one or more immunosuppressants can be any amount that reduces inflammation or B-cell autoantibody production (e.g., B-cell antibody production inhibition or reduction in the number of B-cells) within a mammal having membranous nephropathy without producing significant toxicity to the mammal. For example, the frequency of administration of an immunosuppressant can be from about once a day to about once a month (e.g., from about once a week to about once every other week). The frequency of administration of one or more immunosuppressants can remain constant or can be variable during the duration of treatment. A course of treatment with a composition containing one or more immunosuppressants can include rest periods. For example, a composition containing one or more immunosuppressants can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition may require an increase or decrease in administration frequency.

An effective duration for administering a composition containing one or more immunosuppressants can be any duration that reduces inflammation or B-cell autoantibody production (e.g., B-cell antibody production inhibition or reduction in the number of B-cells) within a mammal having membranous nephropathy without producing significant toxicity to the mammal. In some cases, the effective duration can vary from several days to several months. In general, the effective duration for administering a composition containing one or more immunosuppressants to treat membranous nephropathy can range in duration from about one month to about five years (e.g., from about two months to about five years, from about three months to about five years, from about six months to about five years, from about eight months to about five years, from about one year to about five years, from about one month to about four years, from about one month to about three years, from about one month to about two years, from about six months to about four years, from about six months to about three years, or from about six months to about two years). In some cases, the effective duration for administering a composition containing one or more immunosuppressants to treat membranous nephropathy can be for as long as the mammal is alive. Multiple factors can influence the actual effective duration used for a particular treatment. For example, an effective duration can vary with the frequency of administration, effective amount, use of multiple treatment agents, route of administration, and severity of the condition being treated.

In some cases, a course of treatment and/or the severity of one or more symptoms related to membranous nephropathy can be monitored. Any appropriate method can be used to determine whether or not membranous nephropathy is being treated. For example, immunological techniques (e.g., ELISA) can be performed to determine if the level of autoantibodies (e.g., anti-EXT1 autoantibodies, anti-EXT2 autoantibodies, anti-PLA2R autoantibodies, or anti-THS7DA autoantibodies) present within a mammal being treated as described herein is reduced following the administration of one or more immunosuppressants. Remission and relapse of the disease can be monitored by testing for one or more markers for membranous nephropathy. In some cases, remission can be ascertained by detecting the disappearance or reduction of autoantibodies to THS7DA, PLA2R, EXT1, or EXT2 in the sera. In some cases, relapse of membranous nephropathy can be ascertained by a reappearance or elevation of autoantibodies to THS7DA, PLA2R, EXT1, or EXT2 in the sera.

The invention will be further described in the following examples, which do not limit the scope of the invention described in the claims.

EXAMPLES

Example 1—Exostosin 1/Exostosin 2-Associated Membranous Nephropathy Patients Seven cases of PLA2R-associated Membranous Nephropathy (MN) and 15 cases of PLA2R-negative MN on the kidney biopsy were initially selected. Exostosin 1 (EXT1) and exostosin 2 (EXT2) were detected in five PLA2R-negative MN cases by laser microdissection and mass spectrometry. These results were confirmed by immunohistochemistry (IHC). Subsequently, an additional 209 PLA2R-negative MN cases were analyzed by IHC for EXT1 and EXT2 staining. For controls, 95 cases were used. These controls included: 10 cases of day zero protocol transplant kidney biopsies that were normal on kidney biopsy examination, 40 cases of PLA2R-associated MN, 8 cases of minimal change disease, 12 cases of focal segmental glomerulosclerosis (6 primary and 6 secondary), 5 cases of IgA nephropathy, 7 cases of diabetic nephropathy, and 13 cases of proliferative lupus nephritis without a membranous component. The proliferative lupus nephritis included 2, 2, and 9 cases of class II, III, and class IV lupus nephritis, respectively. Subsequently, expression of EXT1/EXT2 in cases that were positive for EXT1/EXT2 by IHC was confirmed by mass spectrometry studies (FIG. 3).

Light microscopy, immunofluorescence microscopy including PLA2R studies, and electron microscopy was performed in each case of MN. The clinical information was obtained from the accompanying charts.

Validation Cohort

Forty-eight unstained kidney biopsy specimen slides of FFPE tissue were analyzed by IHC for EXT1 and EXT2 was performed. The diagnosis of the biopsy samples was not known at the time of receiving the slides. Subsequently, after the staining, the breakdown of the MN was as follows: 18 cases belonged to class 5 membranous lupus nephritis, 14 cases were class 3/4 lupus nephritis with a component of lupus class 5 MN, and 16 were primary (non-lupus) cases of MN that were negative for both PLA2R and THS7DA (FIG. 3).

Protein Identification by Laser Capture Microdissection, Trypsin Digestion, and nanoLC-Orbitrap Tandem Mass Spectrometry For each case, 10-µ thick formalin-fixed paraffin sections (FFPE) were obtained and mounted on a special PEN membrane laser microdissection slide. Using a Zeiss Palm Microbean microscope, the glomeruli were microdissected to reach approximately 25-50,000 µm$^2$ per case. Resulting FFPE fragments were digested with trypsin and collected for mass spectrometry analysis. The trypsin digested peptides were identified by nano-flow liquid chromatography electrospray tandem mass spectrometry (nanoLC-ESI-MS/MS) using a Thermo Scientific Q-Exactive Mass Spectrometer (Thermo Fisher Scientific, Bremen, Germany) coupled to a Thermo Ultimate 3000 RSLCnano HPLC system. All MS/MS samples were analyzed using Mascot and X! Tandem set up to search a Swissprot human database. Scaffold (version 4.8.3, Proteome Software Inc., Portland, OR) was used to validate MS/MS based peptide and protein identifications. Peptide identifications were accepted at greater than 95.0% probability by the Scaffold Local FDR algorithm and protein identifications required a 2 peptide minimum and a 95% probability using Protein Prophet (Nesvizhskii et al., Anal. Chem., 75:4646-58 (2003)).

Further details for the methods are provided below.

Laser Microdissection and Mass Spectrometry

Formalin fixed paraffin embedded (FFPE) renal biopsy materials were sent to the Mayo Clinic renal biopsy laboratory for diagnosis of membranous nephropathy. For each case, 10 µm thick paraffin sections were obtained and mounted on PEN membrane laser microdissection slides. The sections were deparaffinized using xylene and alcohol. Using a Zeiss Palm Microbean microscope and Robopalm software, multiple glomeruli were microdissected to reach approximately 250-500,000 µm$^2$ per case, and catapulted into 35 µL of digest buffer (100 mM Tris, pH 8.5/0.002% Zwittergent Z3-16) in the cap of a 0.5 mL tube. The tube was removed from the collection plate and spun at 14000g×2 minutes. The samples were frozen until all samples were collected. Upon thawing, samples were heated to 98° C., then proteins were reduced and alkylated by sequential addition of TCEP (Tris(2-carboxyethyl) phosphine hydrochloride) and iodoacetamide to 10 mM for 30 minutes each. Trypsin (0.05 µg) was added to each tube, and proteins were digested overnight at 37° C. for 16-18 hours. After digestion, the samples were acidified with trichloroacetic acid and dried down and resolubilized with A solvent for mass spectrometry.

The trypsin digested peptides were identified by nano-flow liquid chromatography electrospray tandem mass spectrometry (nanoLC-ESI-MS/MS) using a Thermo Scientific Q-Exactive Mass Spectrometer (Thermo Fisher Scientific, Bremen, Germany) coupled to a Thermo Ultimate 3000 RSLCnano HPLC system. The peptide mixture was loaded onto a 250 nL OPTI-PAK trap (Optimize Technologies, Oregon City, OR) custom packed with Michrom Magic C 8, 5 µm solid phase (Michrom Bioresources, Auburn, CA). Chromatography is performed using 0.2% formic acid in both the A solvent (98% water/2% acetonitrile) and B solvent (80% acetonitrile/10% isopropanol/10% water), and a 5% B to 40% B gradient over 90 minutes at 400 nL/minute through a PicoFrit (New Objective, Woburn, MA) 100 µm×35 cm column handpacked with Agilent Poroshell 120 EC C18 packing. The Q-Exactive mass spectrometer experiment was a data dependent set up with the MS1 survey scan from 340-1500 m/z at resolution 70,000 (at 200 m/z), followed by HCD MS/MS scans on the top 15 ions having a charge state of +2, +3, or +4, at resolution 17,500. The ions selected for MS/MS were placed on an exclusion list for 30 seconds. The MS1 AGC target was set to 1e6, and the MS2 target is set to 1e5 with max ion inject times of 50 ms for both.

Database Searching

Tandem mass spectra were extracted by msconvert version 3.0.9134. Charge state deconvolution and deisotoping were not performed. All MS/MS samples were analyzed using Mascot (Matrix Science, London, UK: version 2.4.0) and X! Tandem (The GPM, thegpm.org: version X! Tandem Sledgehammer (2013.09.01.1)). Mascot and X! Tandem were set up to search a Swissprot human database with reverse decoy (40570 entries) assuming the digestion enzyme strict trypsin and with a fragment ion mass tolerance of 0.020 Da and a parent ion tolerance of 10.0 PPM. Glu→pyro-Glu of the n-terminus, ammonia-loss of the n-terminus, gln→pyro-Glu of the n-terminus, and oxidation of methionine were specified in X! Tandem as variable modifications, and carbamidomethyl of cysteine was specified as a fixed modification. Oxidation of methionine and carbamidomethyl of cysteine were specified in Mascot as variable modifications and fixed modifications, respectively.

Criteria for Protein Identification

Scaffold (version Scaffold_4.8.3, Proteome Software Inc., Portland, OR) was used to validate MS/MS based peptide and protein identifications. Peptide identifications were accepted if they were established at greater than 95.0% probability by the Scaffold Local FDR algorithm. Protein identifications were accepted if they were established at greater than 95.0% probability and contained at least two identified peptides. Protein probabilities were assigned by the Protein Prophet algorithm. In general, over 1200-1500 proteins were identified in each sample. Proteins that contained similar peptides and were not differentiated based on MS/MS analysis alone were grouped to satisfy the principles of parsimony. Proteins sharing significant peptide evidence were grouped into clusters. Protein comparisons were made with ratios of Scaffold normalized total spectral counts. The 'Spectra value indicated the total number of mass spectrum collected on the mass spectrometer and was matched to the protein using the proteomics software. A higher number of mass spectra was indicative of greater abundance and typically yielded greater amino acid sequence coverage. A higher mass spectra value also indicated a higher confidence in the protein identification.

Immunohistochemical Staining for Exostosin 1 (EXT1), Exostosin 1 (EXT2), and Exostosin-Like 2 (EXTL2)

Tissue sectioning and immunohistochemical (IHC) staining was performed using the Leica Bond RX stainer (Leica). FFPE tissues were sectioned at 5 microns, and IHC staining was performed on-line. Slides for the EXT1 stain were retrieved for 20 minutes using Epitope Retrieval 2 (EDTA: Leica) and incubated in Protein Block (Dako) for 5 minutes. The EXT1 primary antibody (rabbit polyclonal, Thermo Scientific #PA5-60699) and EXT2 antibody (rabbit polyclonal: Abcam) were diluted to 1:100 in Background Reducing Diluent (Dako) and incubated for 15 minutes. Slides for the EXTL2 stain were retrieved for 20 minutes using Epitope Retrieval 1 (Citrate: Leica) and incubated in Protein Block (Dako) for 5 minutes. The EXTL2 primary antibody (rabbit polyclonal, Origene #TA590761) was diluted to 1:1400 in Background Reducing Diluent (Dako) and incubated for 15 minutes. The detection system used was Polymer Refine Detection System (Leica). This system included the hydrogen peroxidase block, post primary and polymer reagent, DAB, and Hematoxylin. Immunostaining visualization was achieved by incubating slides 10 minutes in DAB and DAB buffer (1:19 mixture) from the Bond Polymer Refine Detection System. To this point, slides were rinsed between steps with 1× Bond Wash Buffer (Leica). Slides were counterstained for five minutes using Schmidt hematoxylin (not provided with the Refine kit) and molecular biology grade water (1:1 mixture), followed by several rinses in 1×Bond wash buffer and distilled water. Once the immunochemistry process was completed, slides were removed from the stainer and rinsed in tap water for five minutes. Slides were dehydrated in increasing concentrations of ethyl alcohol and cleared in three changes of xylene prior to permanent cover slipping in xylene-based medium.

Western Blotting

The protein samples were diluted 1:1 with non-reducing Laemmli sample buffer (Hercules CA, Bio-Rad). 400 ng each of Recombinant Human Exostosin 1/2 Heterodimer, Recombinant Human Exostosin 1 (Minneapolis MN, R&D Systems), and Recombinant Human PLA2R1 (Rockville MD, OriGene Technologies) were boiled for 5 minutes. Samples were loaded into Criterion 4-15% Tris-HCl gels (Hercules CA, Bio-Rad) and electrophoresed in Tris-glycine-SDS running buffer. Proteins were transferred to nitrocellulose membranes, and then membranes were blocked in TBS containing 0.2% non-fat milk. Membranes were probed with human serum overnight at 4° C., at a dilution of 1:100 and then incubated with peroxidase-AffiniPure donkey anti-human IgG (H+L) antibody for 30 minutes at room temperature at a 1:60,000 dilution in TBS containing 0.1% Tween® 20 (Polyoxyethylene (20) sorbitan monolaurate) and 0.2% non-fat milk. Membranes also were probed with rabbit polyclonal antibodies against human EXT1 and human PLA2R overnight at 4° C. at a dilution of 1:500 and 1:1000, respectively, and then incubated with goat anti-rabbit HRP conjugated secondary antibody for 30 minutes at room temperature at a 1:20,000 dilution in TBS containing 0.1% Tween® 20 (Polyoxyethylene (20) sorbitan monolaurate) and 0.2% non-fat milk. Detection was completed with Pierce ECL Western blotting Substrate kit (Rockford IL, Thermo Scientific), and film was developed using a Kodak X-OMat processor.

Results

Clinical and Kidney Biopsy Findings of EXT1/EXT2-Associated MN 26 cases of EXT1/EXT2-associated MN were identified based on IHC. There were 21 (80.8%) female and 5 (19.2%) male patients with ratio of 4.2:1. The mean age at presentation was 35.7 (SD±13.4). The mean serum creatinine and proteinuria at presentation was 1.0 mg/dL (SD±0.9) and 5.9 grams/24 hours (SD±4.8), respectively. Seventeen (70.8%, n=24) exhibited abnormal laboratory values for either anti-nuclear antibodies (ANA), double stranded DNA (dsDNA) antibodies, anti-Smith antibodies, anti-Sjögren syndrome related antigen A or B (SSA or SSB), or anti-ribonucleoprotein (RNP) antibodies. Nine (34.6%) patients exhibited a clinical diagnosis of systemic lupus erythematosus (SLE). None of the patients had hepatitis, although one patient had a history of breast cancer, and one had lung cancer. The summary is given in Table 1. The clinical findings suggest that EXT1/EXT2-associated membranous nephropathy represents the secondary form of membranous nephropathy due to autoimmune diseases such as lupus, mixed connective tissue disorder, etc.

TABLE 1

Clinical and Laboratory data of EXT1/EXT2-associated membranous nephropathy cases.

| Case number | Age/Sex/Ethnicity | Rash/Arthritis/other | Serum Cr (mg/dL) | Proteinuria (g/24 hours) | C3/C4 | ANA/dsDNA Other | Lupus | Hepatitis/ Malignancy |
|---|---|---|---|---|---|---|---|---|
| 1 | 41/M/White | −/−/− | 1.1 | 12.0 | N/N | −/− | No | −/− |
| 2 | 32/F/U | −/− | 0.7 | 5.0 | N/N | +/+ | Yes | −/− |
| 3 | 60/M Hispanic | −/−/− | 1.9 | 20.0 | N/N | −/− | No | −/− |
| 4 | 20/F/Native American | −/−/− | 0.5 | 8.0 | N/N | −/− | No | −/− |
| 5 | 59/F/White | −/+/sicca | 0.6 | 5.7 | N/low | +/− SSA+, SSB+ | No | −/Breast cancer |
| 6 | 29/F/White | −/−/− | 0.8 | 6.0 | N/N | +/− | No | −/− |
| 7 | 19/F/Indian-Hispanic | −/+/− | 0.6 | 2.0 | N/N | +/− | No | −/− |
| 8 | 30/M/Black | −/−/− | 0.7 | 13.0 | N/N | −/− | No | −/− |
| 9 | 55/F/U | −/+/− | 0.7 | 6.0 | N/N | −/− | No | −/SCC lung |
| 10 | 39/F/Indian | −/−/− | 0.5 | 3.0 | ND | +/− SSA+, SSB+ | No | −/− |
| 11 | 30/F/White | −/−/− | 0.5 | 8.4 | N/N | +/− | No | −/− |
| 12 | 32/F/Black | −/−/− | 3.2 | 15.9 | L/N | +/− | No | −/− |
| 13 | 51/F/White | −/+/− | 0.7 | 3.0 | N/N | +/+ SSA+ | No** | −/− |
| 14 | 21/F/Hispanic | −/−/lymphadenopathy | 1.7 | 11 | N/N | −/− | No | −/− |
| 15 | 34/F/Black | −/+/− | 0.7 | 5.1 | N/N | +/− SSA+, SSB+ | No** | −/− |
| 16 | 31/F/Black | −/+/allergies | 0.7 | 2.2 | N/N | −/− | No | −/− |
| 17 | 17/M/White | +/+/myositis | 0.9 | NR | N/N | +/+/+anti Smith, +RNP* | SLE/MCTD overlap | −/− |
| 18 | 25/F/U | +/+/ | 0.8 | NA | N/L | +/+/+SSA+ Anti Smith | Yes | −/− |
| 19 | 32/F/White | −/+/fibromyalgia | 0.6 | 11 | ND | +/+ | Yes | |
| 20. | 67/F/Black | − | 1.1 | 7.8 | ND | −/− | No | −/− |
| 21 | 32/F/Hispanic | −/−/pericardial effusion | 0.4 | 3 | L/L | −/− | No (treated as lupus) | −/− |
| 22 | 38/M | −/+ | 4.6 | 5 | N/N | +/+ | Yes | −/− |
| 23 | 20/F | −/+/− | 0.7 | 3 | ND | +/+ | Yes | |
| 24 | 36/F/Asian | +/−/− | 0.9 | 6 | N/L | +/+ | Yes | |
| 25. | 43/F/Black | −/+/− | 0.7 | 2 | L/L | +/+ | Yes | |
| 26 | 34/F | +/+/pleurisy | 0.9 | 2.2 | N/N | +/+/+anti Smith | Yes | |

ANA, anti-nuclear antibody; dsDNA, anti-double-stranded DNA antibody; M, male; N, normal; F, female; L, low; SCC, squamous cell carcinoma; NR, nephrotic range, five males 20 females; NA, not available; ND, no data/data not available.
* Anti smith/RNP antibody, **Mixed connective tissue order, The kidney biopsy for all cases of EXT1/EXT2-associated MN revealed the characteristic findings of thickened GBM on light microscopy, bright IgG and C3 staining along the capillary wall on immunofluorescence microscopy, and subepithelial deposits on electron microscopy. Overall, an average of 22 (SD±14.4) glomeruli were present of which 2.3 (SD±3.9) were globally sclerosed. Immunofluorescence microscopy revealed bright staining for IgG (2-3+/3) and bright C3 (2-3+/3) for all cases. 22 (84.6%) of 26 cases also exhibited staining for IgA (1-3+/3) or IgM (1-3+/3) or both. 19 (73.0%) of 26 cases exhibited staining for C1q that ranged from 1+/3+ to 3+/3+. All cases showed staining for κ (2-3+/3) and λ (2-3+/3) light chains. Immunofluorescence study for PLA2R was negative in all cases. Electron microscopy revealed subepithelial deposits in all cases, subendothelial deposits in 9 cases (34.6%) and mesangial deposits in 25 cases (96.1%) of the 26 cases. Tubuloreticular inclusions were present in 21 cases (80.7%) of the 26 cases. The pathology findings are shown in Table 2. The pathology findings suggest that EXT1/EXT2-associated membranous nephropathy represents the secondary form of membranous nephropathy due to autoimmune diseases such as lupus, mixed connective tissue disorder, etc.

TABLE 2

Kidney biopsy findings of EXT1/EXT2-associated membranous nephropathy.

| Case | Glomeruli/ sclerosed | Mesangial or endocapillary hypercellularity | Interstitial Inflammation/ IFTA | Arteries | Immunofluorescence microscopy | Electron microscopy deposits SE/SU/ME | Tubuloreticular inclusion |
|---|---|---|---|---|---|---|---|
| 1. | 10/0 | Not present | 0/0 | Moderate sclerosis | IgG(3+) C1q(1+) C3(3+) | +/−/+ | + |
| 2. | 22/0 | Not present, 2 small crescents | 0/0 | Normal | IgG(3+) IgA(3+) IgM(1+) C1q(2+) C3(3+) | +/−/+ | + |
| 3. | 8/2 | Not present | 0/0 | Normal | IgG(2+) IgM(1+) C3(1+) | +/−/− | − |
| 4. | 38/0 | Not present | 0/0 | Normal | IgG(3+) IgM(1+) C3(2+) | +/−/+ | + |
| 5. | 19/1 | Not present | 0/0 | Normal | IgG(3+) IgA(1+) IgM(1+) C1q(1+) C3(3+) | +/+/+ | − |
| 6. | 7/0 | Not present | 0/0 | Normal | IgG(3+) IgA (2+), C1q (1+) C3 (2+) | +/+/+ | + |
| 7. | 64/0 | Not present | 0/0 | Normal | IgG(3+) C3 (1+) | +/+/+ | + |
| 8. | 23/1 | Not present | 0/10 | Normal | IgG(3+) IgA(2+) IgM(1+) C1q(2+) C3(3+) | +/+/+ | + |
| 9. | 26/6 | Not present | 0/0 | Normal | IgG(3+) IgM(1+) C3(2+) | +/−/+ | − |
| 10. | 48/4 | Not present | 0/10 | Normal | IgG(3+) IgA(2+) IgM(1+) C1q(1+) C3(2+) | +/−/+ | + |

TABLE 2-continued

Kidney biopsy findings of EXT1/EXT2-associated membranous nephropathy.

| Case | Glomeruli/sclerosed | Mesangial or endocapillary hypercellularity | Interstitial Inflammation/IFTA | Arteries | Immunofluorescence microscopy | Electron microscopy deposits SE/SU/ME | Tubuloreticular inclusion |
|---|---|---|---|---|---|---|---|
| 11. | 29/5 | Not present | 0/0 | Normal | IgG(2+) IgM(1+) C3(3+) | +/−/+ | − |
| 12. | 54/18 | Not present | 10/30 | Mild sclerosis | IgG(3+) IgM(1+) C1q(1+) C3(3+) | +/−/* | + |
| 13. | 18/1 | Not present | 0/0 | Normal | IgG(3+) IgA(2+) IgM(1+) C1q(2+) C3(3+) | +/−/+ | + |
| 14. | 12/0 | Not present, 3 small crescents | 0/20 | Normal | IgG(3+) IgM(1+) C1q(2+) C3(3+) | +/−/+* | + |
| 15. | 12/2 | Not present | 25/25 | Normal | IgG(3+) IgM(1+) C1q(1+) C3(3+) | +/−/+* | + |
| 16. | 23/1 | Not present | 0/0 | Normal | IgG(3+) C3 (3+) | +/−/+ | + |
| 17. | 17/0 | Not present | 0/0 | Normal | IgG(3+) IgA(2+) C1q(1+) C3(3+) | +/−/+ | + |
| 18. | 4/0 | Not present | 0/0 | Normal | IgG(3+) IgM(2+) C1q(1+) C3(3+) | +/+/+ | + |
| 19. | 14/0 | Not present | 0/0 | Normal | IgG(2+) C3(2+) | +/−/− | − |
| 20. | 18/2 | Not present | 0/0 | Normal | IgG(3+) IgA (2+) IgM(1+) C1q(2+) C3(3+) | +/−/+ | + |
| 21. | 20/1 | Not present | 0/0 | Normal | IgG(3+) IgA (1+) IgM(1+) C1q(2+) C3(3+) | +/−/+ | + |
| 22. | 17/9 | Not present | 0/80 | Severe sclerosis | IgG(3+) IgM(2+) C1q (1+) C3(3+) | +/+/+ | + |
| 23. | 14/0 | Present | 10/30 | Normal | IgG(3+) IgA (3+) IgM(3+) C1q(2+) C3(3+) | +/+/+ | + |
| 24. | 19/2 | Not present | 0/0 | Normal | IgG(3+) IgA (3+) IgM(3+) C1q(2+) C3(3+) | +/+/+* | + |
| 25. | 27/4 | Present | 0/10 | Moderate | IgG(3+) IgM(1+) C1q(2+) C3(3+) | +/+/+ | + |
| 26. | 16/1 | Not present | 0/25 | Normal | IgG(3+) IgM(1+) C1q(2+) C3(2+) | +/−/+ | + |

IFTA, interstitial fibrosis and tubular atrophy; SE, subepithelial; SU, subendothelial; ME, mesangial.
*a*Tubular basement membrane deposits.

Immunohistochemical Staining for EXT1 and EXT2

Figure 4A:
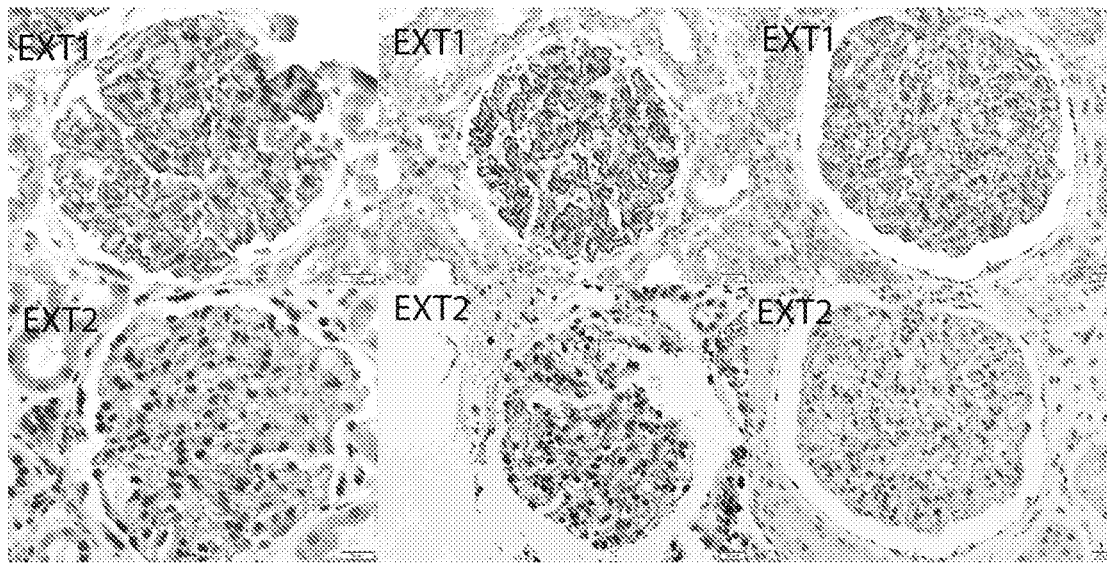
FIG. 4. Immunohistochemical staining for EXT1 and EXT2 in EXT1/EXT2-associated membranous nephropathy, PLA2R-associated membranous nephropathy, and lupus nephritis. A. EXT1/EXT2 associated membranous nephropathy: Bright granular staining for EXT1 and EXT2 along the glomerular basement membranes in three cases of EXT1/EXT2 associated membranous nephropathy. B. PLA2R-associated membranous nephropathy: Negative staining for EXT1 and EXT2 in three cases of PLA2R-associated MN. Each column represents one case. C. Lupus nephritis: Bright positive staining for EXT1 and EXT2 in a case of membranous lupus nephritis (column 1) and negative staining for EXT1 and EXT2 in a case of class II lupus nephritis (column 2) and class IV lupus nephritis (class IV). D. Validation cohort: Bright positive staining for EXT1 and EXT2 in two cases of membranous class 5 lupus nephritis and negative staining in one case of membranous class 5 lupus nephritis.
Figure 4B:
Figure 4C:
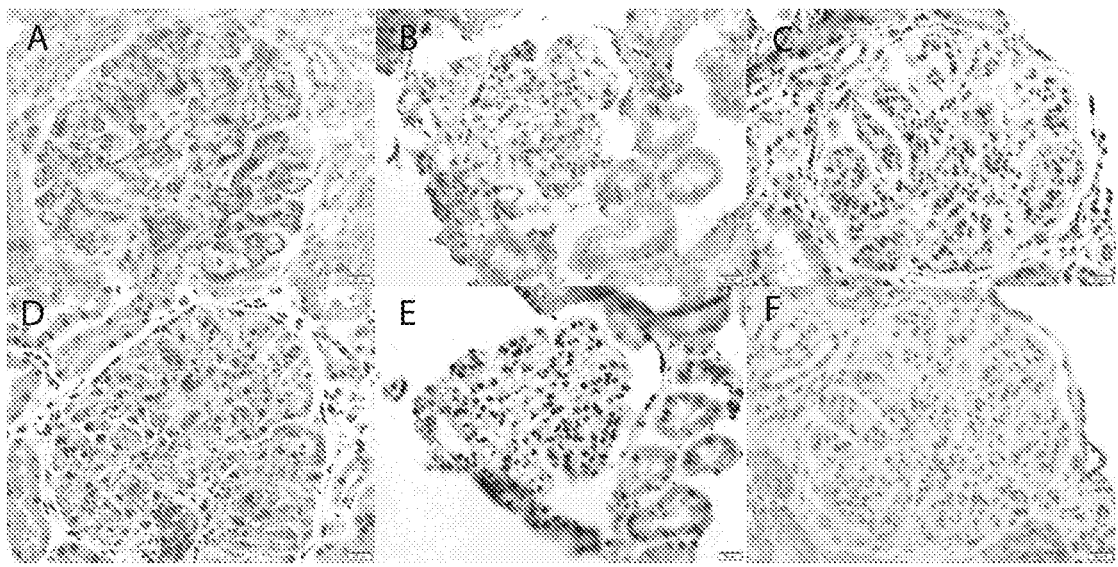
Figure 4D:
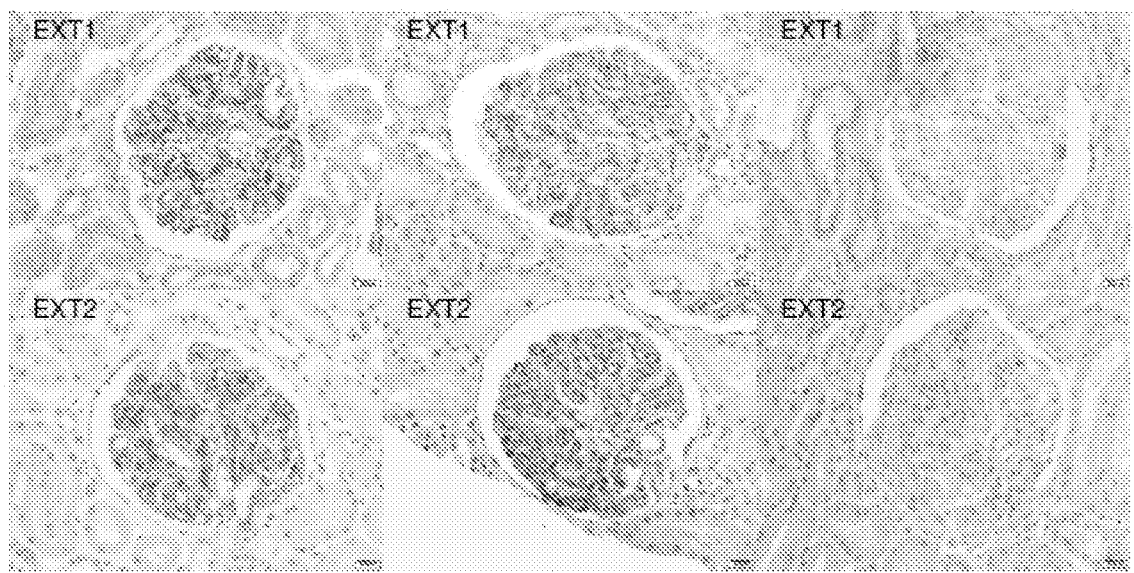

IHC staining for EXT1 and EXT2 was performed in 224 cases of PLA2R-negative MN. 26 (11.6%) cases were positive for EXT1 and EXT2, while the remaining 198 (88.4%) were negative. All 26 positive cases exhibited bright (2-3+/3+) granular staining for EXT1 and EXT2 along the glomerular basement membranes (GBM). There was no staining along the Bowman's capsule, tubular basement membranes, or in vessel walls. EXT1 and EXT2 staining in three cases is shown in FIG. 4A. The positive granular staining mirrored the granular IgG along the GBM seen in each case. All 95 control cases were negative for both EXT1 and EXT2. Representative negative staining for EXT1 and EXT2 in three cases of PLA2R-associated MN is shown in FIG. 4B. FIG. 4C shows positive staining EXT1 and EXT2 in a case of membranous lupus nephritis and negative staining in two cases of proliferative lupus nephritis. Representative EXT1 and EXT2 staining in EXT1/EXT2-associated MN and control cases are shown in FIGS. 8-11 and 13.

Figure 12:
FIG. 12. EXTL2 staining in three cases of EXT1/EXT2-associated membranous nephropathy. Two cases of EXT1/EXT2-associated membranous nephropathy are negative for EXTL2, and one shows minimal (1+) granular staining for EXTL2. Case 5 exhibited very bright EXT1/EXT2 staining.

Exostosin like-1 (EXTL1), exostosin like-2 (EXTL2), and exostosin like-3 (EXTL3) are proteins similar to EXT1 and EXT2. EXTL2 is ubiquitously expressed. To determine whether the IHC staining for EXT1 and EXT2 was specific and if there was cross reactivity between the EXT and EXTL proteins, three EXT1 and EXT2 positive cases were stained for EXTL2. Two cases exhibited no staining for EXTL2, and one exhibited minimal (trace) staining (FIG. 12). Seven cases of PLA2R-associated MN and six cases of day 0 protocol biopsy were stained for EXTL2 and were negative.

Mass Spectrometry Findings

Detection of PLA2R in PLA2R-Associated MN

Figure 5A:
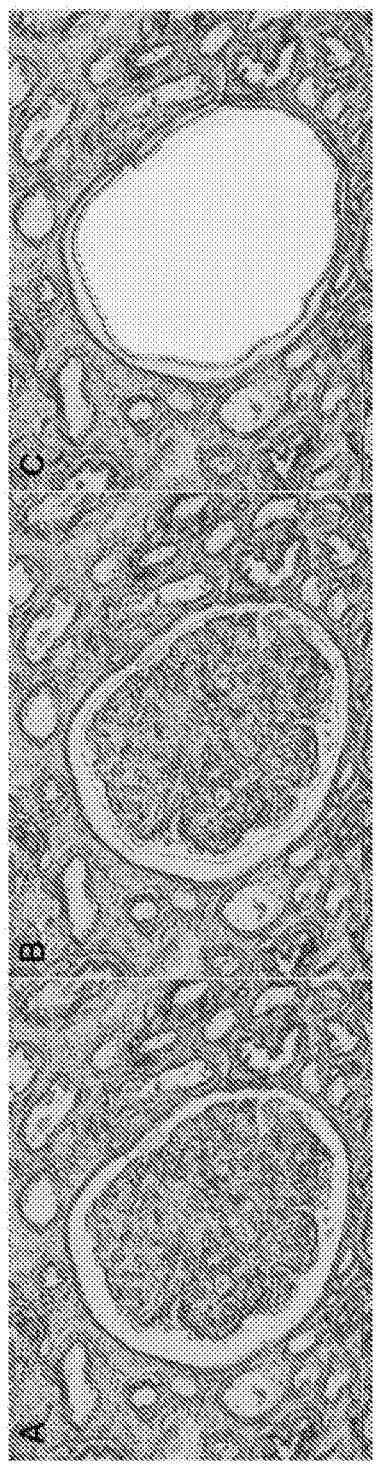
FIG. 5. Proteomic Identification of PLA2R in PLA2R-associated membranous nephropathy and Exostosin 1 and Exostosin 2 in EXT1/EXT2-associated membranous nephropathy. Glomeruli were microdissected and analyzed using mass spectrometry. A. Laser microdissection of glomeruli. One case of MN showing (A) unmarked glomerulus, (B) glomerulus marked for dissection, and (C) vacant space on the slide after microdissection. B. PLA2R-associated membranous nephropathy: Protein identification report from seven cases. Numbers in green boxes represent spectral counts of MS/MS matches to a respective protein. All seven cases exhibited large total spectral counts for PLA2R and immunoglobulins. For comparison, the average total spectral counts from six control cases are provided. EXT1 and EXT2 was not detected in both PLA2R-associated MN and control cases. C. Representative sequence coverage map of PLA2R from one case (SEQ ID NO:5). Amino acids highlighted in bold letters over yellow background are the amino acids detected. Note the extensive coverage. Green highlighted boxes indicated amino acids with artefactual chemical modification induced by mass spectrometry such as oxidation of methionine. D. EXT1/EXT2-associated membranous nephropathy: Protein identification from all 21 cases exhibited large total spectral counts for both EXT1 and EXT2. For comparison, the average total spectral counts in six control cases are provided. IgG1 was the dominant IgG present. E-F. Sequence coverage maps: Representative EXT1 and EXT2 sequence coverage map from a case of EXT1/EXT2-associated membranous nephropathy demonstrating the extensive amino coverage of both (E) EXT1 (SEQ ID NO:2) and (F) EXT2 (SEQ ID NO:4) by MS/MS.
Figures 5B, 5C:
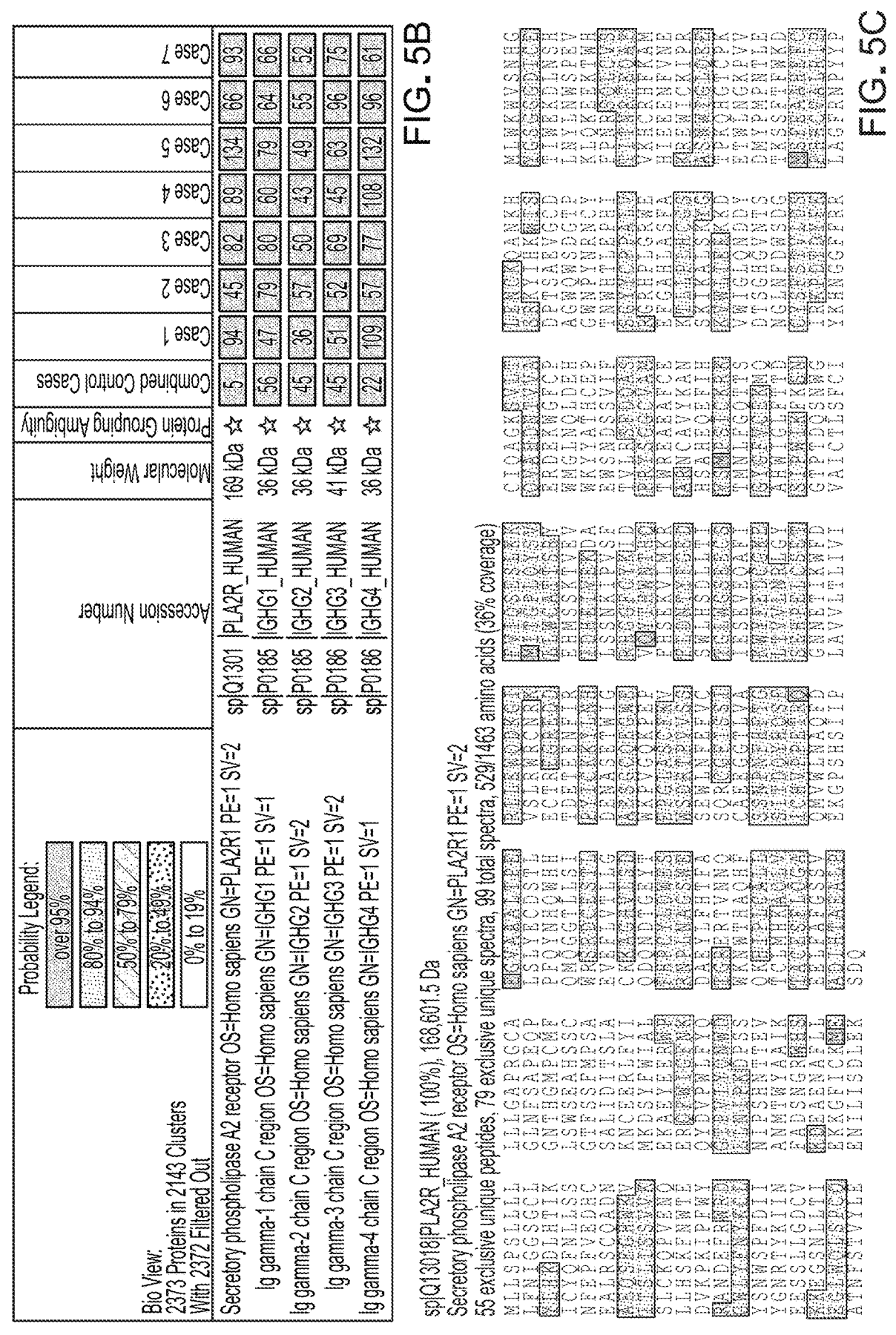

All seven cases exhibited large total spectral counts for PLA2R (FIGS. 5B and 5C). The average PLA2R total spectra count was 86.1 (S.D+27.5, median 89, range 45-134). In comparison, the average PLA2R spectral count in control cases and EXT1/EXT2-associated MN was only 7.1 (S.D+5.2, median 8, range 0-19).

With regard to immunoglobulins (Ig), IgG4 was the most abundant Ig (average spectral count 91.4, S.D+27.6, median 96, range 47-132), followed by IgG1 (average 67.9, S.D+12.3, median 66, range 47-80), IgG3 (average 64.4, S.D+17.5, range 45-96), and IgG2 (average 48.9, S.D+7.2, range 36-57).

Detection of EXT1 and EXT2 in PLA2R-Negative Biopsies

Figure 5D:
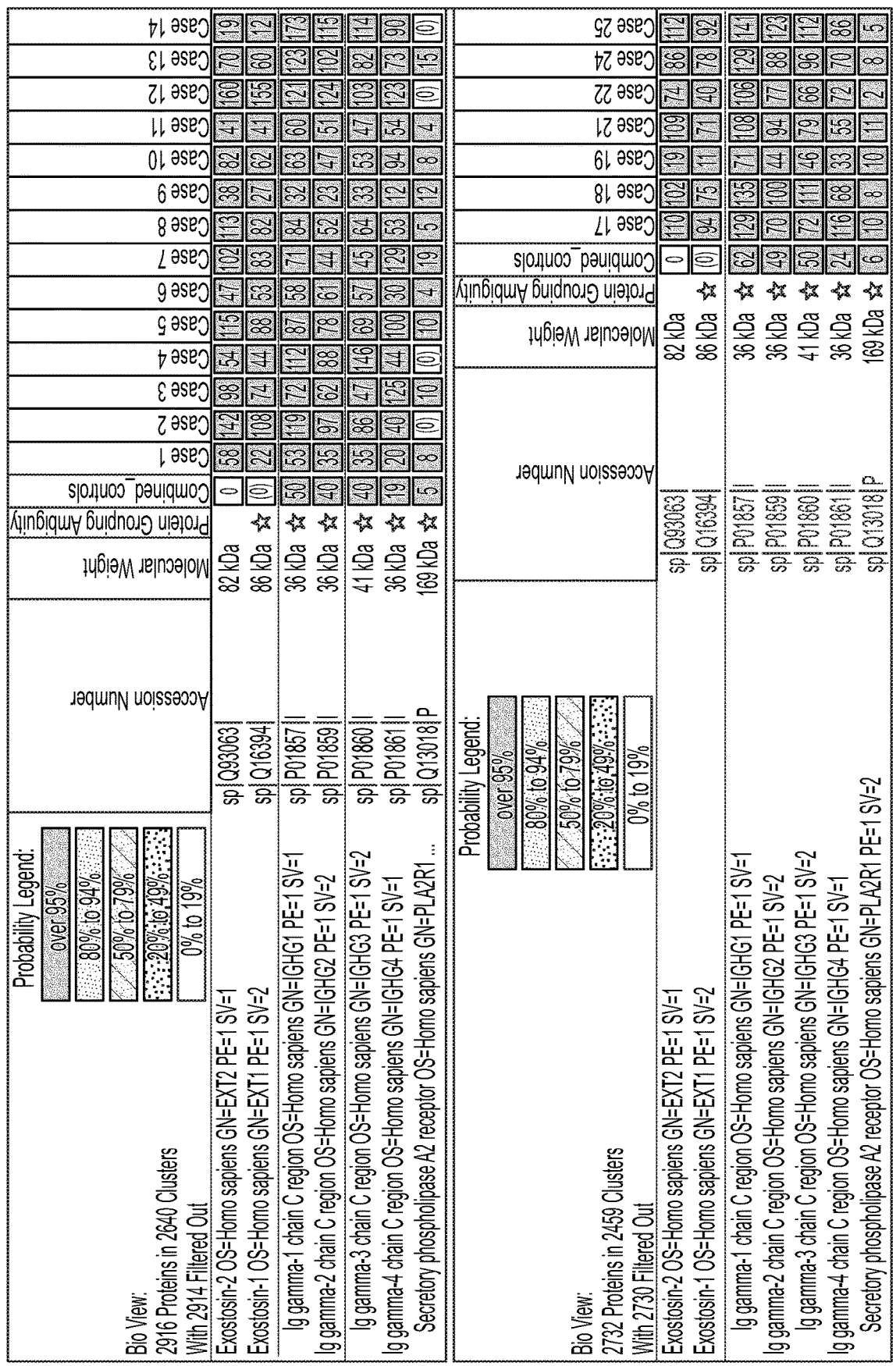
Figures 5E, 5F:
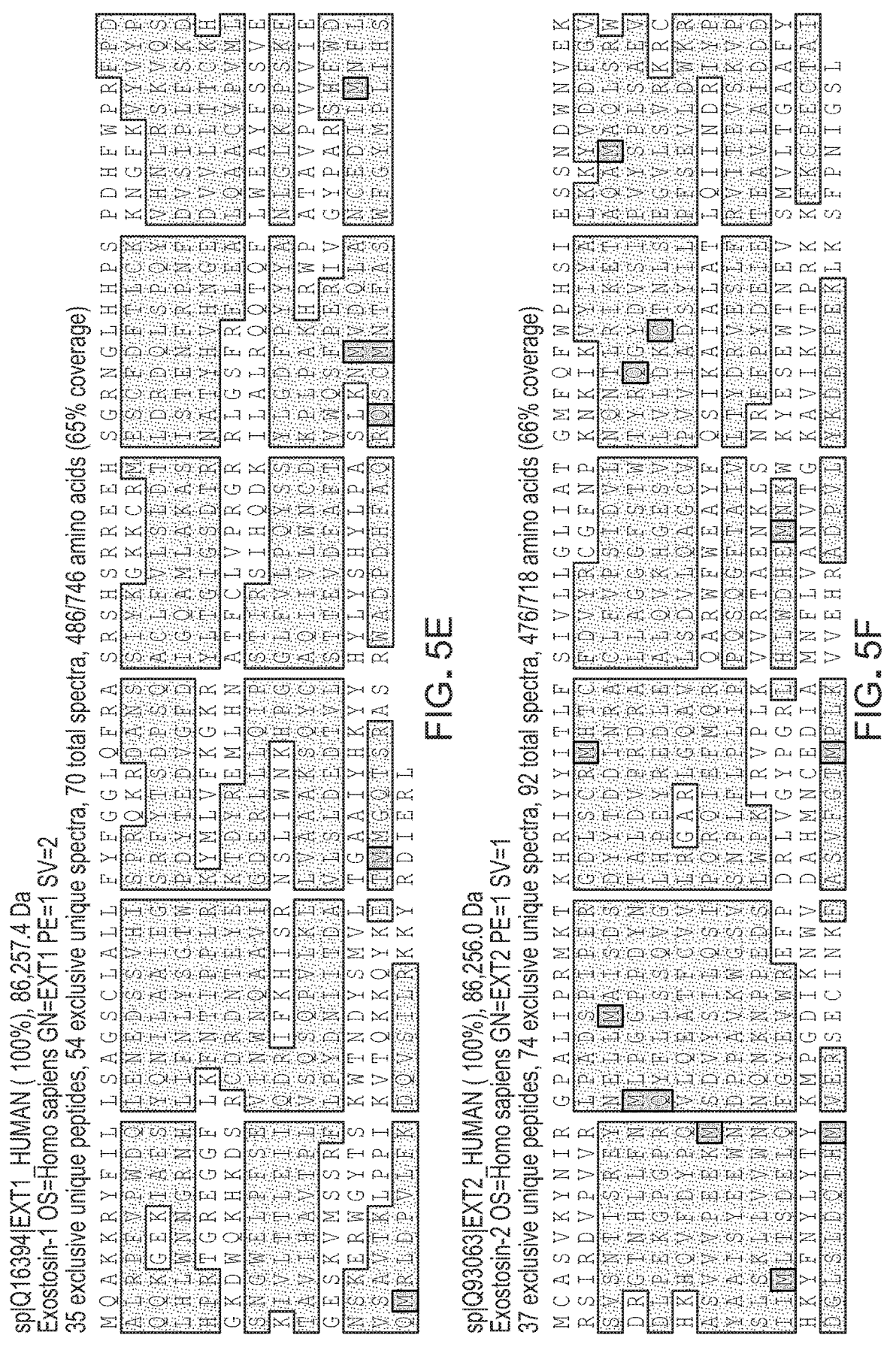
Figure 13:
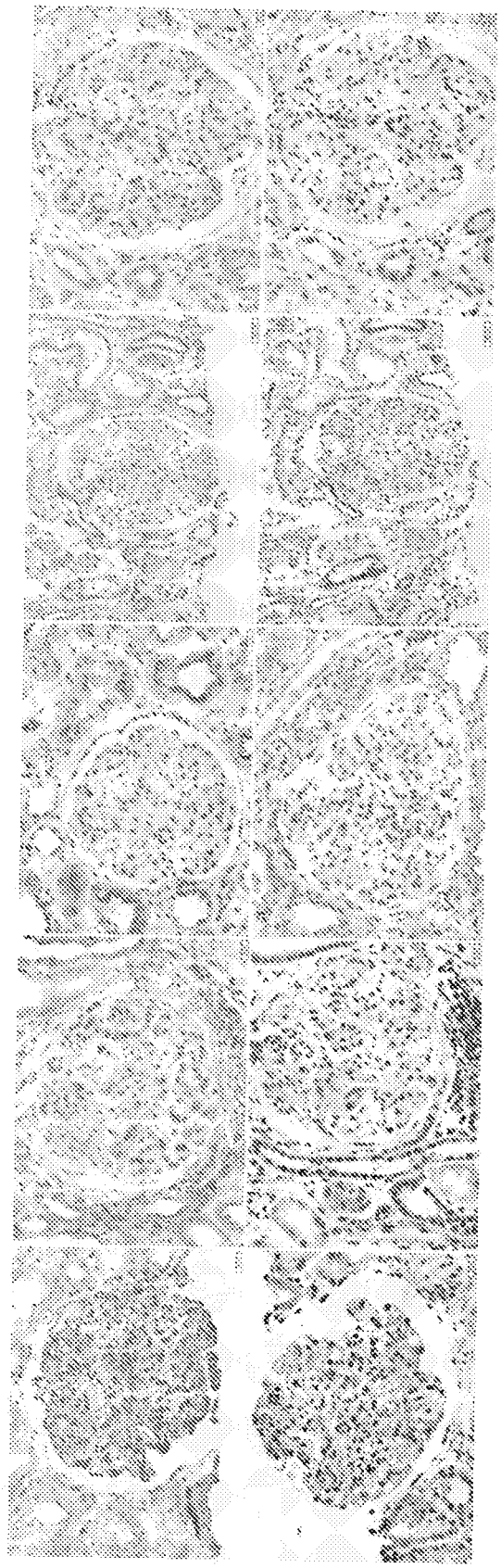
FIG. 13. EXT1/EXT2 staining in control cases compared to EXT1/EXT2-associated membranous nephropathy. Bright granular staining for EXT1/EXT2 along the GBM in a case of EXT1/EXT2-associated membranous nephropathy (column 1), and negative staining in control cases (column 2—IgA nephropathy, column 3—minimal change disease, column 4—FSGS, and column 5—diabetic glomerulosclerosis) (top row EXT1, bottom row EXT2).

Mass spectrometry studies were performed in 21 of 26 cases of EXT1/EXT2-associated MN cases detected on IHC. High total spectral counts of both EXT1 and EXT2 were detected in all 21 cases (FIGS. 5D and 5E). The average total spectral count for EXT1 was 65.3 (S.D+34.6, median 71, range 11-155), and the average total spectral count for EXT2 was 83.4 (range 19-160-176). In general, total spectral counts of EXT2 were slightly higher than EXT1. MS/MS did not detect EXT-like (EXTL) proteins in any of the EXT1/EXT2-associated MN. Also, MS/MS showed only baseline spectral counts of PLA2R in EXT1/EXT2-associated MN. Both the average EXT1 and EXT2 total spectral numbers in EXT1/EXT2-associated MN were comparable to total spectral counts of PLA2R in PLA2R-associated cases. All control cases including PLA2R-associated MN cases were negative for EXT1 or EXT2 spectra (FIG. 13). MS/MS spectral matches to sequences from EXT1 and EXT2 are shown in FIG. 14.

With regard to immunoglobulins (Ig), all four classes of Ig were detected in EXT1/EXT2-associated MN. IgG1 was the most abundant Ig (average 97.5, S.D+35.9, median 106, range 32-173)), followed by IgG2 (average 75, S.D+29.5, median 77, range 23-124)), IgG3 (average 74.4, S.D+30.3, median 69, range 33-146)), and IgG4 (average 70.8, S.D+35.2, median 8, range 12-129)). The average spectral counts of IgG1 were much higher than IgG4 in EXT1/EXT2-associated MN (p<0.01), and also when compared to the total spectral counts of IgG1 in the PLA2R associated MN (p=0.04).

Validation Cohort

Eight of 18 (44%) cases of lupus class 5 membranous nephritis were positive for EXT1 and EXT2 staining along the GBM, whereas only one of the 14 cases of mixed class 5 and class 3/4 lupus nephritis was positive for EXT1 and EXT2 along the GBM. Three (19%) of 16 cases of PLA2R- and THS7DA negative and non-lupus MN cases were positive for EXT1 and EXT2 staining along the GBM. These three cases had features of autoimmune disease on chart review. Patients #14 and #16 are of particular interest because they both later developed a full-blown lupus. In patient #14, the initial diagnosis was MN stage 1-2 with an immunofluorescence pattern of primary MN. Six years later, she developed full-blown clinical lupus, but the lesions and immunofluorescence pattern were unchanged. Patient #16 also had a presentation and an immunofluorescence pattern of primary MN, but she developed a year later very active clinical lupus disease with a mixed pattern of class 3 plus 5. She was referred 10 years later for nephrotic syndrome with asymptomatic lupus and class 5 MN on biopsy (FIG. 6). In the two patients mentioned above, EXT1/EXT2 staining remained positive throughout evolution and histologic classes. Representative EXT1 and EXT2 staining of positive cases is shown in FIG. 6D.

Western and Native Blotting

Figure 7A:
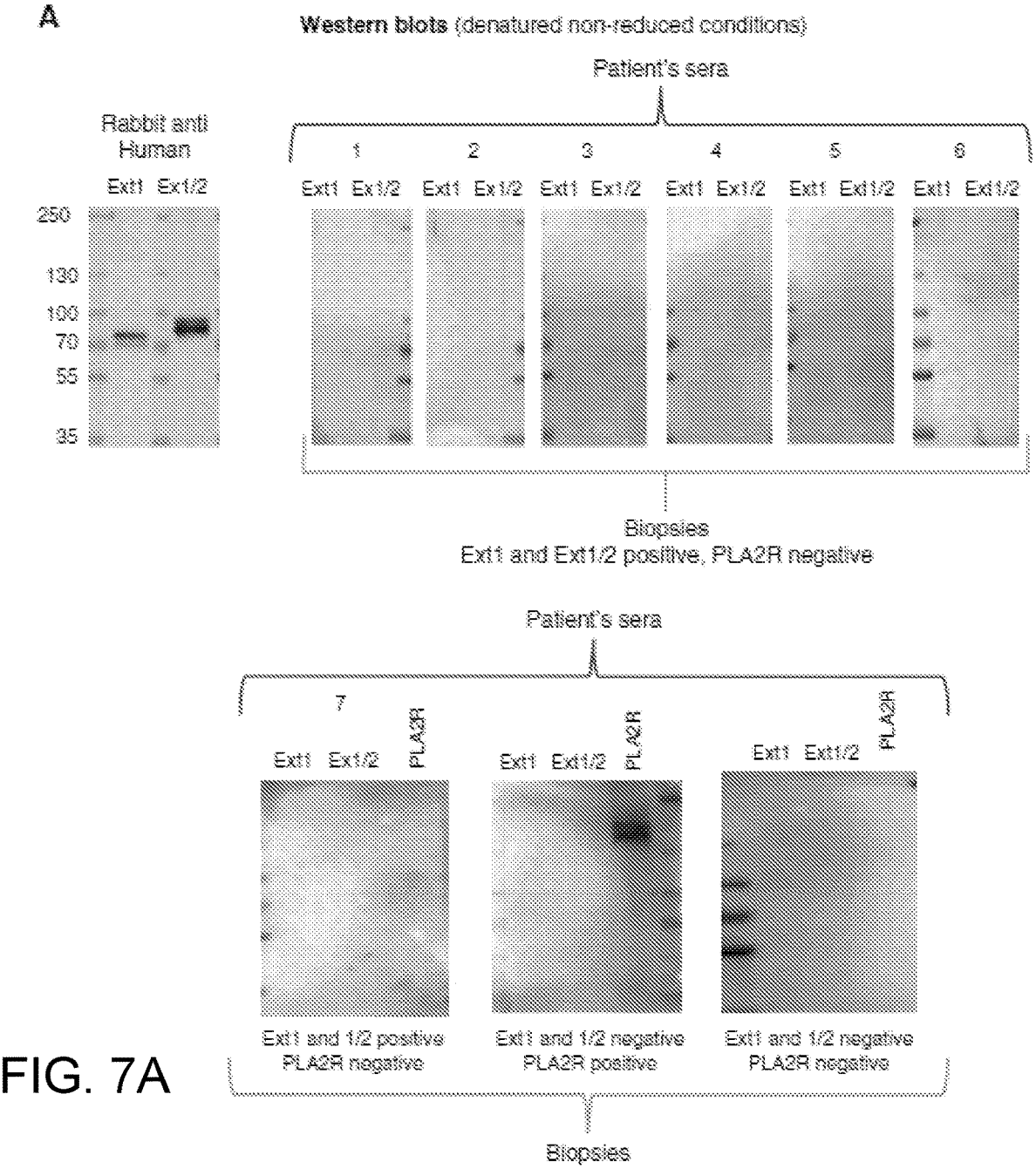
FIG. 7. Western and native blotting analyses of sera from patients with EXT1/EXT2 glomerular deposits and a patient with PLA2R-related MN. A. Western blotting (denatured, nonreduced conditions) revealed a 82 kd-band when the serum of the patient was incubated with the heterodimer EXT1/EXT2 protein and EXT1 protein, but no band was detected when the serum was incubated with PLA2R protein. The upper panel shows lack of reactivity with recombinant EXT1 and heterodimer EXT1/EXT2 of six sera from patients with EXT1- and EXT2-positive biopsies, contrasting with strong reactivity of the rabbit anti-human EXT1 and EXT2. Shown are five of six available sera from the validation cohort: the last serum on the right is one available from the discovery cohort. The sixth available serum from the validation cohort is shown in the lower panel (left). The lower panel shows reactivity of sera from three patients with or without EXT1 and EXT1/2 deposits or PLA2R deposits in the kidney biopsy specimens. For this western blot, EXT1, EXT1/2, and PLA2R recombinant antigens were run in three different, consecutive lanes before transfer, and the blots were then incubated with each of the patient sera. Strong reactivity with PLA2R of the serum from PLA2R-related MN and lack of reactivity with EXT1 and EXT1/2 of the three sera were noted. B.Slot blots (nondenaturing, nonreduced conditions) revealed no bands when the serum of the patient was incubated with the heterodimer EXT1/EXT2 protein and EXT1 protein. Slot blotting analysis confirms lack of reactivity in nondenaturing conditions with recombinant EXT1 and EXT1/2 protein of seven sera from patients with EXT1- and EXT2-positive biopsy specimens.

Circulating antibodies to EXT1 and the heterodimer EXT1/EXT2 in seven EXT1/EXT2-positive patients were searched for with available sera (one from the discovery and six from the validation cohorts), and in one control patient with glomerular PLA2R deposits. Western blotting was performed in SDS gels under non-reducing and reducing conditions to detect autoantibodies to EXT1 or EXT2 or the heterodimer of EXT1/EXT2 in an index case of EXT1/EXT2-associated MN. Despite strong reactivity of the recombinant protein with a control rabbit anti-human EXT1 and EXT2 serum, no reactivity was detected with the seven tested sera, as well as with one serum from a patient with PLA2R-related MN (FIG. 7A, top panel). In contrast, the serum from this patient strongly reacted with a 185-kd band when it was incubated with PLA2R antigen, and no band was detected when the serum was incubated with heterodimer EXT1/EXT2 or EXT1 alone (FIG. 7A, bottom panel).

Figure 7B:
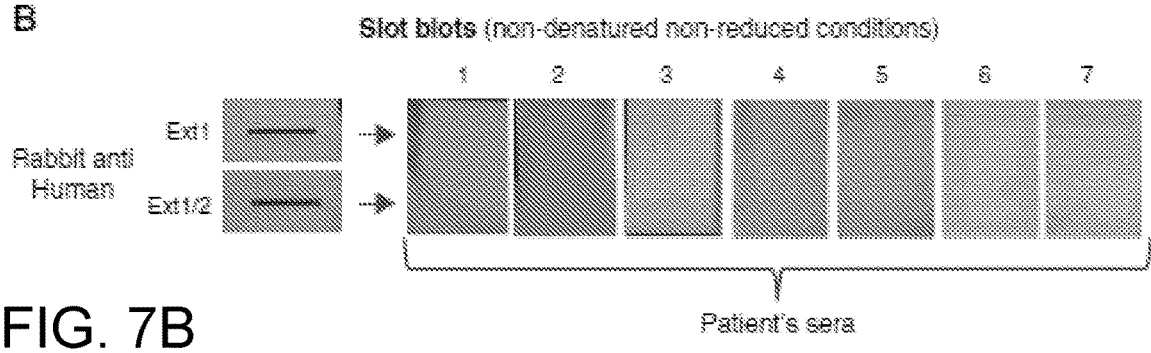
Figure 8:
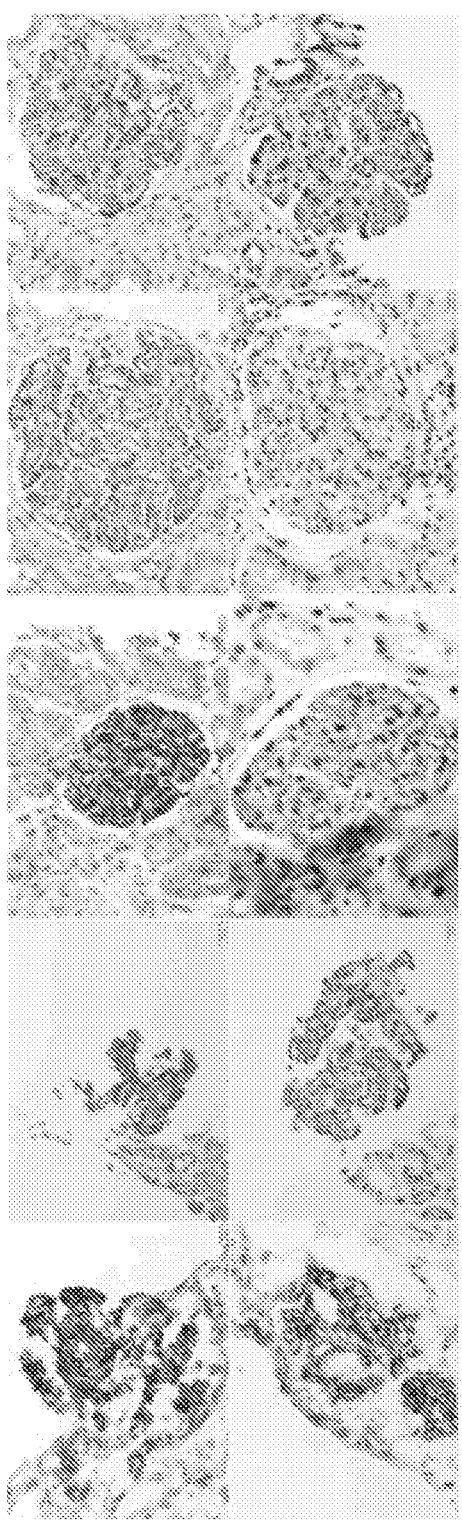
FIG. 8. EXT1/EXT2-associated membranous nephropathy. Bright granular staining for EXT1 and EXT2 along the GBM in five more cases of EXT1/EXT2 associated membranous nephropathy. The first column is case 1, column 2 is case 2, column 3 is case 5, column 4 is case 6, and column 5 is case 8 (top row EXT1, bottom row EXT2).
Figure 9:
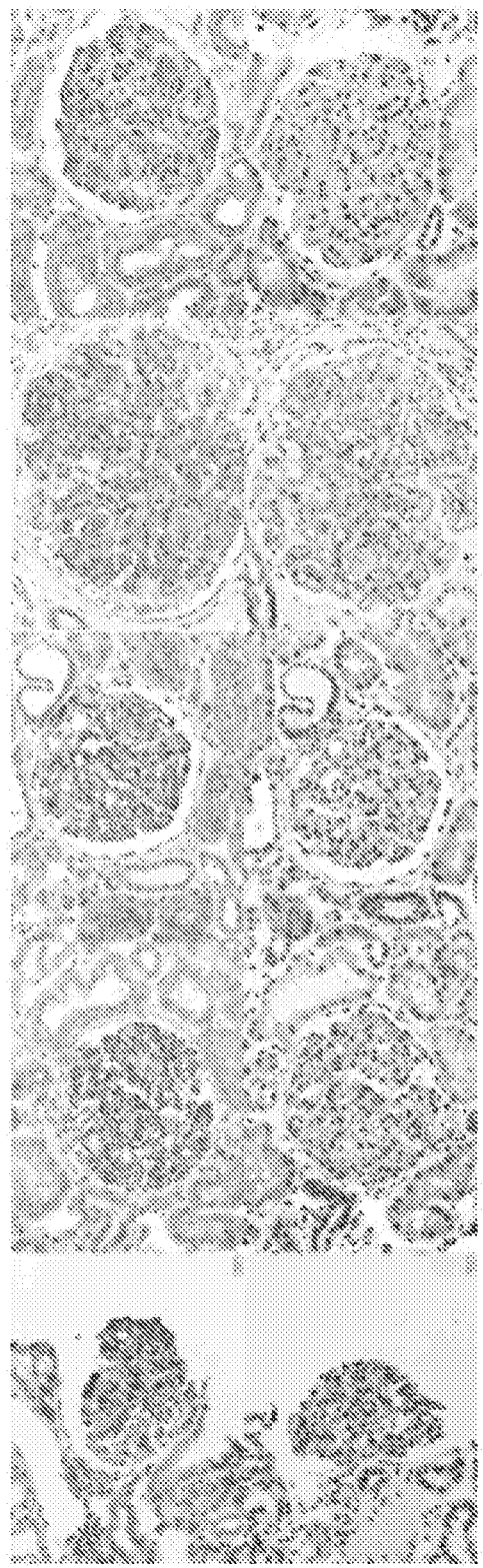
FIG. 9. EXT1/EXT2-associated membranous nephropathy. Bright granular staining for EXT1 and EXT2 along the GBM in five additional cases of EXT1/EXT2 associated membranous nephropathy. The first column is case 9, column 2 is case 10, column 3 is case 11, column 4 is case 12, and column 5 is case 13 (top row EXT1, bottom row EXT2).
Figure 10:
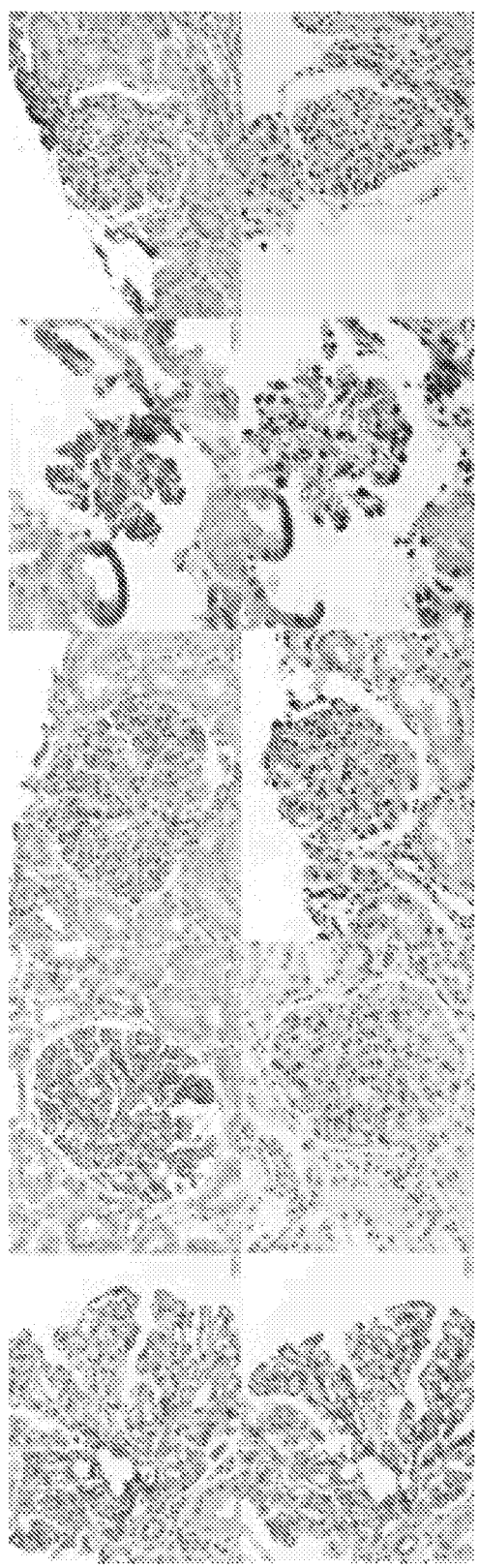
FIG. 10. EXT1/EXT2-associated membranous nephropathy. Bright granular staining for EXT1 and EXT2 along the GBM in five additional cases of EXT1/EXT2 associated membranous nephropathy. The first column is case 15, column 2 is case 16, column 3 is case 17, column 4 is case 18, and column 5 is case 19 (top row EXT1, bottom row EXT2).
Figure 11:
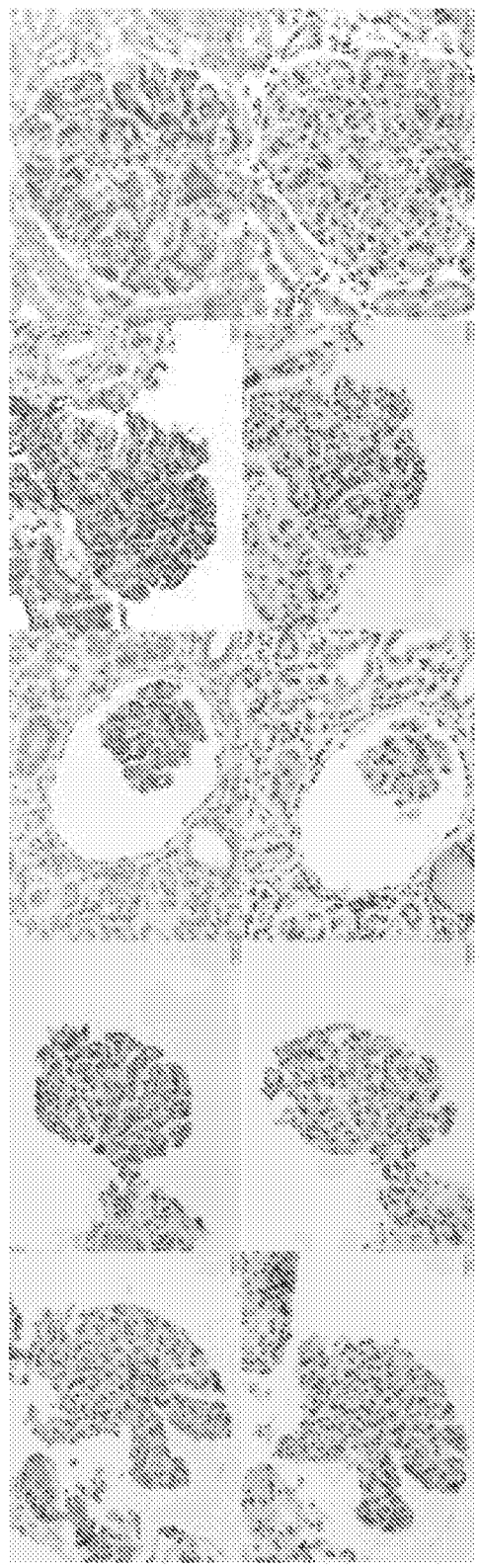
FIG. 11. EXT1/EXT2-associated membranous nephropathy. Bright granular staining for EXT1 and EXT2 along the GBM in five additional cases of EXT1/EXT2 associated membranous nephropathy. The first column is case 20, column 2 is case 21, column 3 is case 22, column 4 is case 23, and column 5 is case 26 (top row EXT1, bottom row EXT2).

To investigate the presence of epitopes sensitive to denaturation by SDS, a native blotting method was used. However, none of the seven tested sera showed reactivity with recombinant EXT1 and EXT1/2 by this method (FIG. 7B), suggesting that, under these experimental conditions, circulating anti-EXT1/EXT2 antibodies were unable to be detected.

Example 2-Prevalence of Exostosin 1/Exostosin 2 Associated Membranous Lupus Nephritis This Example evaluates the finding of an elevated level of an EXT1 and/or EXT2 polypeptide in a secondary form of membranous nephropathy due to autoimmune diseases such as lupus in a large cohort of patients with membranous lupus nephritis.

Methods 374 cases of biopsy-proven lupus membranous nephritis (LMN) were studied. Immunohistochemical studies (IHC) using antibodies against EXT1/EXT2 were performed on paraffin-embedded sections. Laser microdissection and mass spectrometry were performed on a subset of these cases.

Results

Of the 374 LMN cases, 122 (32.6%), were EXT1/EXT2-positive and 252 (67.4%) were EXT1/EXT2 negative by IHC. Among the 122 cases, 86.9% were female. At presentation, the median serum creatinine and proteinuria were 0.8 mg/dL (range: 0.4-14.7) and 4 g/day (range: 0.4-13.5). Kidney biopsies revealed an average of 16.6 glomeruli (SD: +10.0) with an average of 9.6% glomerulosclerosis (SD: +15.2). Interstitial fibrosis and tubular atrophy was minimal (<10%) in 89 (72.9%), mild (11-25%) in 21 (17.2%), moderate (26-50%) in 8 (6.6%), and severe (>51%) in 4 (3.3%) cases, respectively. Further, 30 (24.6%) patients had proliferative features (Class III/IV). Mass spectrometry was performed on 8 cases, which showed high spectral counts for EXT 1 (average: 88.6, SD: +37.2) and EXT 2 (average: 66.1, SD: +34.6) thus confirming the IHC findings. Among the 252 EXT1/EXT2 negative cases, 81 (32.1%) patients showed proliferative features. MS was performed in 7 of these 253 cases and was negative for EXT1/EXT2.

These results demonstrate that samples from patients having LMN contain an elevated level of an EXT1 and/or EXT2 polypeptide.

Example 3—Exemplary Embodiments

Embodiment 1. A method for identifying a mammal as having membranous nephropathy comprising an elevated level of a polypeptide within kidney tissue of said mammal, wherein said polypeptide is an exostosin 1 (EXT1) polypeptide or an exostosin 2 (EXT2) polypeptide, wherein said method comprises: (a) determining the presence or absence of autoantibodies within said mammal, wherein said autoantibodies are specific for said polypeptide, (b) classifying said mammal as having said membranous nephropathy if said autoantibodies are present within said mammal, and (c) classifying said mammal as not having said membranous nephropathy if said autoantibodies are absent within said mammal.

Embodiment 2. The method of Embodiment 1, wherein said mammal is a human.

Embodiment 3. The method of any one of Embodiments 1-2, wherein said polypeptide is said EXT1 polypeptide.

Embodiment 4. The method of any one of Embodiments 1-2, wherein said polypeptide is said EXT2 polypeptide.

Embodiment 5. The method of any one of Embodiments 1-4, wherein said membranous nephropathy lacks an elevated level of a PLA2R polypeptide within said kidney tissue.

Embodiment 6. The method of any one of Embodiments 1-5, wherein said membranous nephropathy lacks an elevated level of a THS7DA polypeptide within said kidney tissue.

Embodiment 7. The method of any one of Embodiments 1-6, wherein said method comprises detecting the presence of said autoantibodies and classifying said mammal as having said membranous nephropathy.

Embodiment 8. The method of any one of Embodiments 1-6, wherein said method comprises detecting the absence of said autoantibodies and classifying said mammal as not having said membranous nephropathy.

Embodiment 9. A method for identifying a mammal as having kidney tissue comprising an elevated level of a polypeptide, wherein said polypeptide is an exostosin 1 (EXT1) polypeptide or an exostosin 2 (EXT2) polypeptide, wherein said method comprises: (a) determining the presence or absence of said kidney tissue within a sample obtained from said mammal, (b) classifying said mammal as having said kidney tissue if said presence is determined, and (c) classifying said mammal as not having said kidney tissue if said absence is determined.

Embodiment 10. The method of Embodiment 9, wherein said mammal is a human.

Embodiment 11. The method of any one of Embodiments 9-10, wherein said polypeptide is said EXT1 polypeptide.

Embodiment 12. The method of any one of Embodiments 9-10, wherein said polypeptide is said EXT2 polypeptide.

Embodiment 13. The method of any one of Embodiments 9-12, wherein said kidney tissue lacks an elevated level of a PLA2R polypeptide.

Embodiment 14. The method of any one of Embodiments 9-13, wherein said kidney tissue lacks an elevated level of a THS7DA polypeptide.

Embodiment 15. The method of any one of Embodiments 9-14, wherein said method comprises detecting said presence and classifying said mammal as having said kidney tissue.

Embodiment 16. The method of any one of Embodiments 9-14, wherein said method comprises detecting said absence and classifying said mammal as not having said kidney tissue.

Embodiment 17. A method for identifying a mammal having membranous nephropathy as having autoantibodies specific for a polypeptide, wherein said polypeptide is an exostosin 1 (EXT1) polypeptide or an exostosin 2 (EXT2) polypeptide, wherein said method comprises: (a) determining the presence or absence of said autoantibodies within said mammal, (b) classifying said mammal as having said autoantibodies if said autoantibodies are present within said mammal, and (c) classifying said mammal as not having said autoantibodies if said autoantibodies are absent within said mammal.

Embodiment 18. The method of Embodiment 17, wherein said mammal is a human.

Embodiment 19. The method of any one of Embodiments 17-18, wherein said polypeptide is said EXT1 polypeptide.

Embodiment 20. The method of any one of Embodiments 17-18, wherein said polypeptide is said EXT2 polypeptide.

Embodiment 21. The method of any one of Embodiments 17-20, wherein kidney tissue of said mammal lacks an elevated level of a PLA2R polypeptide.

Embodiment 22. The method of any one of Embodiments 17-21, wherein kidney tissue of said mammal lacks an elevated level of a THS7DA polypeptide.

Embodiment 23. The method of any one of Embodiments 17-22, wherein said method comprises detecting said presence and classifying said mammal as having said autoantibodies.

Embodiment 24. The method of any one of Embodiments 17-22, wherein said method comprises detecting said absence and classifying said mammal as not having said autoantibodies.

Embodiment 25. A method for treating a mammal having membranous nephropathy, wherein said method comprises: (a) identifying a mammal as having (i) autoantibodies specific for a polypeptide or (ii) kidney tissue comprising an elevated level of said polypeptide, wherein said polypeptide is an exostosin 1 (EXT1) polypeptide or an exostosin 2 (EXT2) polypeptide, and (b) administering an immunosuppressant to said mammal.

Embodiment 26. The method of Embodiment 25, wherein said mammal is a human.

Embodiment 27. The method of any one of Embodiments 25-26, wherein said mammal is identified as having said autoantibodies.

Embodiment 28. The method of any one of Embodiments 25-27, wherein said mammal is identified as having said kidney tissue.

Embodiment 29. The method of any one of Embodiments 25-28, wherein said polypeptide is said EXT1 polypeptide.

Embodiment 30. The method of any one of Embodiments 25-28, wherein said polypeptide is said EXT2 polypeptide.

Embodiment 31. The method of any one of Embodiments 25-30, wherein said immunosuppressant is a B-cell inhibitor.

Embodiment 32. The method of claim 31, wherein said B-cell inhibitor is rituximab.

Embodiment 33. The method of any one of Embodiments 25-30, wherein said immunosuppressant is a calcineurin inhibitor.

Embodiment 34. The method of Embodiment 33, wherein said calcineurin inhibitor is cyclosporine or tacrolimus.

Embodiment 35. The method of any one of Embodiments 25-30, wherein said immunosuppressant is an mTOR inhibitor.

Embodiment 36. The method of Embodiment 35, wherein said mTOR inhibitor is sirolimus or everolimus.

Embodiment 37. The method of any one of Embodiments 25-30, wherein said immunosuppressant is a DNA damage inducer.

Embodiment 38. The method of Embodiment 37, wherein said DNA damage inducer is chlorambucil.

Embodiment 39. The method of any one of Embodiments 25-38, wherein the level of autoantibodies present within said mammal is reduced by at least 5 percent following said administering step.

Embodiment 40. The method of any one of Embodiments 25-38, wherein the level of autoantibodies present within said mammal is reduced by at least 25 percent following said administering step.

Embodiment 41. The method of any one of Embodiments 25-38, wherein the level of autoantibodies present within said mammal is reduced by at least 50 percent following said administering step.

Embodiment 42. A method for treating a mammal having membranous nephropathy, wherein said method comprises administering an immunosuppressant to a mammal identified as having (i) autoantibodies specific for a polypeptide or (ii) kidney tissue comprising an elevated level of said polypeptide, wherein said polypeptide is an exostosin 1 (EXT1) polypeptide or an exostosin 2 (EXT2) polypeptide.

Embodiment 43. The method of Embodiment 42, wherein said mammal is a human.

Embodiment 44. The method of any one of Embodiments 42-43, wherein said mammal was identified as having said autoantibodies.

Embodiment 45. The method of any one of Embodiments 42-44, wherein said mammal was identified as having said kidney tissue.

Embodiment 46. The method of any one of Embodiments 42-45, wherein said polypeptide is said EXT1 polypeptide.

Embodiment 47. The method of any one of Embodiments 42-45, wherein said polypeptide is said EXT2 polypeptide.

Embodiment 48. The method of any one of Embodiments 42-47, wherein said immunosuppressant is a B-cell inhibitor.

Embodiment 49. The method of Embodiment 48, wherein said B-cell inhibitor is rituximab.

Embodiment 50. The method of any one of Embodiments 42-47, wherein said immunosuppressant is a calcineurin inhibitor.

Embodiment 51. The method of Embodiment 50, wherein said calcineurin inhibitor is cyclosporine or tacrolimus.

Embodiment 52. The method of any one of Embodiments 42-47, wherein said immunosuppressant is an mTOR inhibitor.

Embodiment 53. The method of Embodiment 52, wherein said mTOR inhibitor is sirolimus or everolimus.

Embodiment 54. The method of any one of Embodiments 42-47, wherein said immunosuppressant is a DNA damage inducer.

Embodiment 55. The method of Embodiment 54, wherein said DNA damage inducer is chlorambucil.

Embodiment 56. The method of any one of Embodiments 42-55, wherein the level of autoantibodies present within said mammal is reduced by at least 5 percent following said administering step.

Embodiment 57. The method of any one of Embodiments 42-55, wherein the level of autoantibodies present within said mammal is reduced by at least 25 percent following said administering step.

Embodiment 58. The method of any one of Embodiments 42-55, wherein the level of autoantibodies present within said mammal is reduced by at least 50 percent following said administering step.

Embodiment 59. A method for treating a mammal having membranous nephropathy and kidney tissue comprising an elevated level of a polypeptide, wherein said polypeptide is an exostosin 1 (EXT1) polypeptide or an exostosin 2 (EXT2) polypeptide, wherein said method comprises administering an immunosuppressant to said mammal.

Embodiment 60. The method of Embodiment 59, wherein said mammal is a human.

Embodiment 61. The method of any one of Embodiments 59-60, wherein said mammal comprises autoantibodies specific for said polypeptide.

Embodiment 62. The method of any one of Embodiments 59-61, wherein said mammal was identified as having said kidney tissue.

Embodiment 63. The method of any one of Embodiments 59-62, wherein said polypeptide is said EXT1 polypeptide.

Embodiment 64. The method of any one of Embodiments 59-62, wherein said polypeptide is said EXT2 polypeptide.

Embodiment 65. The method of any one of Embodiments 59-64, wherein said kidney tissue lacks an elevated level of a PLA2R polypeptide.

Embodiment 66. The method of any one of Embodiments 59-65, wherein said kidney tissue lacks an elevated level of a THS7DA polypeptide.

Embodiment 67. The method of any one of Embodiments 59-66, wherein said immunosuppressant is a B-cell inhibitor.

Embodiment 68. The method of Embodiment 67, wherein said B-cell inhibitor is rituximab.

Embodiment 69. The method of any one of Embodiments 59-66, wherein said immunosuppressant is a calcineurin inhibitor.

Embodiment 70. The method of Embodiment 69, wherein said calcineurin inhibitor is cyclosporine or tacrolimus.

Embodiment 71. The method of any one of Embodiments 59-66, wherein said immunosuppressant is an mTOR inhibitor.

Embodiment 72. The method of Embodiment 71, wherein said mTOR inhibitor is sirolimus or everolimus.

Embodiment 73. The method of any one of Embodiments 59-66, wherein said immunosuppressant is a DNA damage inducer.

Embodiment 74. The method of Embodiment 73, wherein said DNA damage inducer is chlorambucil.

Embodiment 75. The method of any one of Embodiments 59-74, wherein the level of autoantibodies present within said mammal is reduced by at least 5 percent following said administering step.

Embodiment 76. The method of any one of Embodiments 59-74, wherein the level of autoantibodies present within said mammal is reduced by at least 25 percent following said administering step.

Embodiment 77. The method of any one of Embodiments 59-74, wherein the level of autoantibodies present within said mammal is reduced by at least 50 percent following said administering step.

Embodiment 78. A method for treating membranous nephropathy, wherein said method comprises administering an immunosuppressant to said mammal without detecting the presence, within said mammal, of autoantibodies specific for any polypeptide of a group of polypeptides and without detecting the presence of kidney tissue of said mammal comprising an elevated level of any polypeptide of said group, wherein said group consists of an EXT1 polypeptide, an EXT2 polypeptide, a PLA2R polypeptide, and a THS7DA polypeptide.

Embodiment 79. The method of claim 78, wherein said mammal is a human.

Embodiment 80. The method of any one of Embodiments 78-79, wherein said mammal comprises autoantibodies specific for said EXT1 polypeptide.

Embodiment 81. The method of any one of Embodiments 78-79, wherein said mammal comprises autoantibodies specific for said EXT2 polypeptide.

Embodiment 82. The method of any one of Embodiments 78-79, wherein said mammal comprises autoantibodies specific for said PLA2R polypeptide.

Embodiment 83. The method of any one of Embodiments 78-79, wherein said mammal comprises autoantibodies specific for said THS7DA polypeptide.

Embodiment 84. The method of any one of Embodiments 78-83, wherein said immunosuppressant is a B-cell inhibitor.

Embodiment 85. The method of Embodiment 84, wherein said B-cell inhibitor is rituximab.

Embodiment 86. The method of any one of Embodiments 78-83, wherein said immunosuppressant is a calcineurin inhibitor.

Embodiment 87. The method of Embodiment 86, wherein said calcineurin inhibitor is cyclosporine or tacrolimus.

Embodiment 88. The method of any one of Embodiments 78-83, wherein said immunosuppressant is an mTOR inhibitor.

Embodiment 89. The method of Embodiment 88, wherein said mTOR inhibitor is sirolimus or everolimus.

Embodiment 90. The method of any one of Embodiments 78-83, wherein said immunosuppressant is a DNA damage inducer.

Embodiment 91. The method of Embodiment 90, wherein said DNA damage inducer is chlorambucil.

Embodiment 92. The method of any one of Embodiments 78-91, wherein the level of autoantibodies present within said mammal is reduced by at least 5 percent following said administering step.

Embodiment 93. The method of any one of Embodiments 78-91, wherein the level of autoantibodies present within said mammal is reduced by at least 25 percent following said administering step.

Embodiment 94. The method of any one of Embodiments 78-91, wherein the level of autoantibodies present within said mammal is reduced by at least 50 percent following said administering step.

OTHER EMBODIMENTS

It is to be understood that while the invention has been described in conjunction with the detailed description thereof, the foregoing description is intended to illustrate

What is claimed is:

1. A method for treating a mammal having membranous nephropathy, wherein said method comprises administering an immunosuppressant to a mammal identified as having (i) autoantibodies specific for a polypeptide or (ii) kidney tissue comprising an elevated level of said polypeptide as compared to a level of said polypeptide in normal kidney tissue, wherein said polypeptide is an exostosin 1 (EXT1) polypeptide or an exostosin 2 (EXT2) polypeptide.

2. The method of claim 1, wherein said mammal is a human.

3. The method of claim 1, wherein said mammal was identified as having said autoantibodies.

4. The method of claim 1, wherein said mammal was identified as having said kidney tissue.

5. The method of claim 1, wherein said polypeptide is said EXT1 polypeptide.

6. The method of claim 1, wherein said polypeptide is said EXT2 polypeptide.

7. The method of claim 1, wherein the level of autoantibodies present within said mammal is reduced by at least 5 percent following said administering step.

8. The method of claim 1, wherein the level of autoantibodies present within said mammal is reduced by at least 25 percent following said administering step.

9. The method of claim 1, wherein the level of autoantibodies present within said mammal is reduced by at least 50 percent following said administering step.

10. The method of claim 1, wherein said immunosuppressant is a B-cell inhibitor.

11. The method of claim 10, wherein said B-cell inhibitor is rituximab.

12. The method of claim 1, wherein said immunosuppressant is a calcineurin inhibitor.

13. The method of claim 12, wherein said calcineurin inhibitor is cyclosporine or tacrolimus.

14. The method of claim 1, wherein said immunosuppressant is an mTOR inhibitor.

15. The method of claim 14, wherein said mTOR inhibitor is sirolimus or everolimus.

16. The method of claim 1, wherein said immunosuppressant is a DNA damage inducer.

17. The method of claim 16, wherein said DNA damage inducer is chlorambucil.

* * * * *